(12) United States Patent
Wells et al.

(10) Patent No.: US 8,498,699 B2
(45) Date of Patent: Jul. 30, 2013

(54) METHOD AND NERVE STIMULATOR USING SIMULTANEOUS ELECTRICAL AND OPTICAL SIGNALS

(75) Inventors: Jonathon D. Wells, Seattle, WA (US); Mark P. Bendett, Kirkland, WA (US); James S. Webb, Seattle, WA (US); Charles A. Lemaire, Apple Valley, MN (US); Austin R. Duke, Nashville, TN (US); E. Duco Jansen, Nashville, TN (US); Peter E. Konrad, Nashville, TN (US); Anita Mahadevan-Jansen, Nashville, TN (US)

(73) Assignees: Lockheed Martin Company, Bethesda, MD (US); Vanderbilt University, Nashville, TN (US)

( * ) Notice: Subject to any disclaimer, the term of this patent is extended or adjusted under 35 U.S.C. 154(b) by 9 days.

(21) Appl. No.: 13/013,816

(22) Filed: Jan. 26, 2011

(65) Prior Publication Data

US 2011/0172725 A1 Jul. 14, 2011

Related U.S. Application Data

(63) Continuation-in-part of application No. 12/573,848, filed on Oct. 5, 2009, now Pat. No. 8,160,696.

(60) Provisional application No. 61/102,811, filed on Oct. 3, 2008, provisional application No. 61/298,543, filed on Jan. 26, 2010.

(51) Int. Cl.
*A61N 1/00* (2006.01)
(52) U.S. Cl.
USPC .................................. 607/3; 607/88

(58) Field of Classification Search
USPC ..................... 607/3, 88–95, 53–57
See application file for complete search history.

(56) References Cited

U.S. PATENT DOCUMENTS 4,064,872 A 12/1977 Caplan
4,215,694 A 8/1980 Isakov et al.
(Continued)

FOREIGN PATENT DOCUMENTS

WO WO 0025112 5/2000

OTHER PUBLICATIONS

Allegre, et al., "Stimulation in the rat of a nerve fiber bundle by a short UV pulse from an excimer laser", "NeuroScience Letters", 1994, pp. 261-264, vol. 180.

(Continued)

*Primary Examiner* — Scott Getzow
(74) *Attorney, Agent, or Firm* — Charles A. Lemaire; Jonathan M. Rixen; Lemaire Patent Law Firm, P.L.L.C.

(57) ABSTRACT

An apparatus and method for stimulating animal tissue (for example to trigger a nerve action potential (NAP) signal in a human patient) by application of both electrical and optical signals for treatment and diagnosis purposes. The application of an electrical signal before or simultaneously to the application of a NAP-triggering optical signal allows the use of a lower amount of optical power or energy than would otherwise be needed if an optical signal alone was used for the same purpose and effectiveness. The application of the electrical signal may precondition the nerve tissue such that a lower-power optical signal can be used to trigger the desired NAP, which otherwise would take a higher-power optical signal were the electric signal not applied. Some embodiments include an implanted nerve interface having a plurality of closely spaced electrodes placed transversely and/or longitudinally to the nerve and a plurality of optical emitters.

23 Claims, 19 Drawing Sheets

U.S. PATENT DOCUMENTS

| | | | |
|---|---|---|---|
| 4,232,678 A | 11/1980 | Skovajsa | |
| 4,296,995 A | 10/1981 | Bickel | |
| 4,558,703 A | 12/1985 | Mark | |
| 4,566,935 A | 1/1986 | Hornbeck | |
| 4,596,992 A | 6/1986 | Hornbeck | |
| 4,671,285 A | 6/1987 | Walker | |
| 4,681,791 A | 7/1987 | Shibahashi et al. | |
| 4,724,835 A | 2/1988 | Liss et al. | |
| 4,768,516 A | 9/1988 | Stoddart et al. | |
| 4,813,418 A | 3/1989 | Harris | |
| 4,840,485 A | 6/1989 | Gratton | |
| 4,928,695 A | 5/1990 | Goldman et al. | |
| 4,930,504 A | 6/1990 | Diamantopoulos et al. | |
| 4,972,331 A | 11/1990 | Chance | |
| 4,989,605 A | 2/1991 | Rossen | |
| 5,062,428 A | 11/1991 | Chance | |
| 5,088,493 A | 2/1992 | Giannini et al. | |
| 5,122,974 A | 6/1992 | Chance | |
| 5,139,025 A | 8/1992 | Lewis et al. | |
| 5,150,704 A | 9/1992 | Tatebayashi et al. | |
| 5,151,909 A | 9/1992 | Davenport et al. | |
| 5,152,278 A | 10/1992 | Clayman | |
| 5,187,672 A | 2/1993 | Chance et al. | |
| 5,192,278 A | 3/1993 | Hayes et al. | |
| 5,212,386 A | 5/1993 | Gratton et al. | |
| 5,213,093 A | 5/1993 | Swindle | |
| 5,213,105 A | 5/1993 | Gratton et al. | |
| 5,257,202 A | 10/1993 | Feddersen et al. | |
| 5,259,382 A | 11/1993 | Kronberg | |
| 5,261,822 A | 11/1993 | Hall et al. | |
| 5,323,010 A | 6/1994 | Gratton et al. | |
| 5,327,902 A | 7/1994 | Lemmen | |
| 5,353,799 A | 10/1994 | Chance | |
| 5,386,827 A | 2/1995 | Chance et al. | |
| 5,402,778 A | 4/1995 | Chance | |
| 5,419,312 A | 5/1995 | Arenberg et al. | |
| 5,430,175 A | 7/1995 | Hess et al. | |
| 5,445,146 A | 8/1995 | Bellinger | |
| 5,464,960 A | 11/1995 | Hall et al. | |
| 5,480,482 A | 1/1996 | Novinson | |
| 5,484,432 A | 1/1996 | Sand | |
| 5,548,604 A | 8/1996 | Toepel | |
| 5,553,614 A | 9/1996 | Chance | |
| 5,564,417 A | 10/1996 | Chance | |
| 5,608,519 A | 3/1997 | Gourley et al. | |
| 5,664,574 A | 9/1997 | Chance | |
| 5,704,899 A | 1/1998 | Milo | |
| 5,754,578 A | 5/1998 | Jayaraman | |
| 5,755,752 A | 5/1998 | Segal | |
| 5,792,051 A | 8/1998 | Chance | |
| 5,796,889 A | 8/1998 | Xu et al. | |
| 5,799,030 A | 8/1998 | Brenner | |
| 5,851,223 A | 12/1998 | Liss et al. | |
| 5,899,865 A | 5/1999 | Chance | |
| 5,913,884 A | 6/1999 | Trauner et al. | |
| 6,033,431 A | 3/2000 | Segal | |
| 6,048,359 A | 4/2000 | Biel | |
| 6,066,127 A | 5/2000 | Abe | |
| 6,074,411 A | 6/2000 | Lai et al. | |
| 6,104,957 A | 8/2000 | Alo et al. | |
| 6,110,195 A | 8/2000 | Xie et al. | |
| 6,152,882 A | 11/2000 | Prutchi | |
| 6,171,239 B1 | 1/2001 | Humphrey | |
| 6,184,542 B1 | 2/2001 | Alphonse | |
| 6,224,969 B1 | 5/2001 | Steenbergen et al. | |
| 6,246,892 B1 | 6/2001 | Chance | |
| 6,257,759 B1 | 7/2001 | Witonsky et al. | |
| 6,258,082 B1 | 7/2001 | Lin | |
| 6,263,221 B1 | 7/2001 | Chance et al. | |
| 6,267,779 B1 | 7/2001 | Gerdes | |
| 6,272,367 B1 | 8/2001 | Chance | |
| 6,284,078 B1 | 9/2001 | Witonsky et al. | |
| 6,294,109 B1 | 9/2001 | Ratna et al. | |
| 6,301,279 B1 | 10/2001 | Garbuzov et al. | |
| 6,310,083 B1 | 10/2001 | Kao et al. | |
| 6,312,451 B1 | 11/2001 | Streeter | |
| 6,314,324 B1 | 11/2001 | Lattner et al. | |
| 6,324,429 B1 | 11/2001 | Shire et al. | |
| 6,330,388 B1 | 12/2001 | Bendett et al. | |
| 6,339,606 B1 | 1/2002 | Alphonse | |
| 6,353,226 B1 | 3/2002 | Khalil et al. | |
| 6,358,272 B1 | 3/2002 | Wilden | |
| 6,363,188 B1 | 3/2002 | Alphonse | |
| 6,417,524 B1 | 7/2002 | Alphonse | |
| 6,421,474 B2 | 7/2002 | Jewell et al. | |
| 6,444,313 B1 | 9/2002 | Ono et al. | |
| 6,456,866 B1 | 9/2002 | Tyler et al. | |
| 6,459,715 B1 | 10/2002 | Khalfin et al. | |
| 6,475,800 B1 | 11/2002 | Hazen et al. | |
| 6,488,704 B1 | 12/2002 | Connelly et al. | |
| 6,493,476 B2 | 12/2002 | Bendett | |
| 6,505,075 B1 | 1/2003 | Weiner | |
| 6,542,530 B1 | 4/2003 | Shieh et al. | |
| 6,542,772 B1 | 4/2003 | Chance | |
| 6,546,291 B2 | 4/2003 | Merfeld et al. | |
| 6,556,611 B1 | 4/2003 | Khalfin et al. | |
| 6,564,076 B1 | 5/2003 | Chance | |
| 6,585,411 B2 | 7/2003 | Hammarth et al. | |
| 6,592,611 B1 | 7/2003 | Zawada | |
| 6,630,673 B2 | 10/2003 | Khalil et al. | |
| 6,636,678 B1 | 10/2003 | Bendett et al. | |
| 6,639,930 B2 | 10/2003 | Griffel et al. | |
| 6,669,379 B2 | 12/2003 | Janosik et al. | |
| 6,669,765 B2 | 12/2003 | Senga et al. | |
| 6,688,783 B2 | 2/2004 | Janosik et al. | |
| 6,690,873 B2 | 2/2004 | Bendett et al. | |
| 6,735,474 B1 | 5/2004 | Loeb et al. | |
| 6,735,475 B1 | 5/2004 | Whitehurst et al. | |
| 6,744,548 B2 | 6/2004 | Abeles | |
| 6,748,275 B2 | 6/2004 | Lattner et al. | |
| 6,823,109 B2 | 11/2004 | Sasaki et al. | |
| RE38,670 E | 12/2004 | Asah et al. | |
| 6,836,685 B1 | 12/2004 | Fitz | |
| 6,871,084 B1 | 3/2005 | Kingsley et al. | |
| 6,902,528 B1 | 6/2005 | Garibaldi et al. | |
| 6,909,826 B2 | 6/2005 | Cai et al. | |
| 6,921,413 B2 | 7/2005 | Mahadevan-Jansen et al. | |
| 6,956,650 B2 | 10/2005 | Boas et al. | |
| 6,980,579 B2 | 12/2005 | Jewell | |
| 6,989,023 B2 | 1/2006 | Black | |
| 7,003,353 B1 | 2/2006 | Parkhouse | |
| 7,004,645 B2 | 2/2006 | Lemoff et al. | |
| 7,006,749 B2 | 2/2006 | Illich et al. | |
| 7,031,363 B2 | 4/2006 | Biard et al. | |
| 7,040,805 B1 | 5/2006 | Ou et al. | |
| 7,068,878 B2 | 6/2006 | Crossman-Bosworth et al. | |
| 7,069,083 B2 | 6/2006 | Finch | |
| 7,079,900 B2 | 7/2006 | Greenburg et al. | |
| 7,085,300 B2 | 8/2006 | Werner et al. | |
| 7,095,770 B2 | 8/2006 | Johnson | |
| 7,116,886 B2 | 10/2006 | Colgan et al. | |
| 7,139,603 B2 | 11/2006 | Chance | |
| 7,156,866 B1 | 1/2007 | Riggs et al. | |
| 7,177,081 B2 | 2/2007 | Tomita et al. | |
| 7,194,063 B2 | 3/2007 | Dilmanian et al. | |
| 7,225,028 B2 | 5/2007 | Della Santina et al. | |
| 7,231,256 B2 | 6/2007 | Wahlstrand et al. | |
| 7,244,253 B2 | 7/2007 | Neev | |
| 7,302,296 B1 | 11/2007 | Hoffer | |
| 7,311,722 B2 | 12/2007 | Larsen | |
| 7,324,852 B2 | 1/2008 | Barolat et al. | |
| 7,329,251 B2 | 2/2008 | Yamada et al. | |
| 7,337,004 B2 | 2/2008 | Classen et al. | |
| 7,391,561 B2 | 6/2008 | Di Teodoro et al. | |
| 7,402,167 B2 | 7/2008 | Nemenov | |
| 7,647,112 B2 | 1/2010 | Tracey et al. | |
| 7,654,750 B2 | 2/2010 | Brenner et al. | |
| 7,736,382 B2 | 6/2010 | Webb et al. | |
| 7,776,631 B2 | 8/2010 | Miles | |
| 7,787,170 B2 | 8/2010 | Patel et al. | |
| 7,792,588 B2 | 9/2010 | Harding | |
| 7,797,029 B2 | 9/2010 | Gibson et al. | |
| 7,801,601 B2 * | 9/2010 | Maschino et al. | 607/2 |
| 7,873,085 B2 | 1/2011 | Babushkin et al. | |
| 7,883,536 B1 | 2/2011 | Bendett et al. | |
| 7,914,842 B1 | 3/2011 | Greenberg et al. | |
| 7,951,181 B2 | 5/2011 | Mahadevan-Jansen et al. | |

| | | |
|---|---|---|
| 8,012,189 B1 | 9/2011 | Webb et al. |
| 2001/0021287 A1 | 9/2001 | Jewell et al. |
| 2002/0002391 A1 | 1/2002 | Gerdes |
| 2002/0123781 A1 | 9/2002 | Shanks et al. |
| 2002/0147400 A1 | 10/2002 | Chance |
| 2003/0083724 A1 | 5/2003 | Jog et al. |
| 2003/0165171 A1 | 9/2003 | Jewell |
| 2003/0236458 A1 | 12/2003 | Hochman |
| 2004/0073101 A1 | 4/2004 | Chance |
| 2004/0116985 A1 | 6/2004 | Black |
| 2004/0225339 A1 | 11/2004 | Yaroslavsky et al. |
| 2004/0243111 A1 | 12/2004 | Bendett et al. |
| 2004/0243112 A1 | 12/2004 | Bendett et al. |
| 2005/0065531 A1 | 3/2005 | Cohen |
| 2005/0096720 A1 | 5/2005 | Sharma et al. |
| 2005/0099824 A1 | 5/2005 | Dowling et al. |
| 2005/0142344 A1 | 6/2005 | Toepel |
| 2005/0143789 A1 | 6/2005 | Whitehurst et al. |
| 2005/0169597 A1 | 8/2005 | Colgan et al. |
| 2005/0216072 A1 | 9/2005 | Mahadevan-Jansen et al. |
| 2005/0228256 A1 | 10/2005 | Labadie et al. |
| 2006/0095105 A1 | 5/2006 | Jog et al. |
| 2006/0129210 A1 | 6/2006 | Cantin et al. |
| 2006/0161218 A1 | 7/2006 | Danilov |
| 2006/0161227 A1 | 7/2006 | Walsh et al. |
| 2006/0167564 A1 | 7/2006 | Flaherty et al. |
| 2006/0276861 A1 | 12/2006 | Lin |
| 2007/0036493 A1 | 2/2007 | Brenner et al. |
| 2007/0053996 A1 | 3/2007 | Boyden et al. |
| 2007/0054319 A1 | 3/2007 | Boyden et al. |
| 2007/0060983 A1 | 3/2007 | Merfeld |
| 2007/0060984 A1 | 3/2007 | Webb et al. |
| 2007/0179557 A1 | 8/2007 | Maschino et al. |
| 2007/0191906 A1 | 8/2007 | Iyer et al. |
| 2007/0260297 A1 | 11/2007 | Chariff |
| 2007/0261127 A1 | 11/2007 | Boyden et al. |
| 2008/0009748 A1 | 1/2008 | Gratton et al. |
| 2008/0077198 A1 | 3/2008 | Webb et al. |
| 2008/0077200 A1 | 3/2008 | Bendett et al. |
| 2008/0086206 A1 | 4/2008 | Nasiatka et al. |
| 2008/0140149 A1* | 6/2008 | John et al. ................ 607/45 |
| 2008/0161697 A1 | 7/2008 | Chance |
| 2008/0183247 A1 | 7/2008 | Harding |
| 2009/0030327 A1 | 1/2009 | Chance |
| 2009/0076115 A1 | 3/2009 | Wharton et al. |
| 2009/0163982 A1 | 6/2009 | DeCharms |
| 2009/0177255 A1 | 7/2009 | Merfeld |
| 2009/0210039 A1 | 8/2009 | Boyden et al. |
| 2010/0145418 A1 | 6/2010 | Zhang et al. |
| 2010/0162109 A1 | 6/2010 | Chatterjee et al. |
| 2010/0174329 A1* | 7/2010 | Dadd et al. ................ 607/3 |
| 2010/0184818 A1 | 7/2010 | Wharton et al. |
| 2010/0292758 A1 | 11/2010 | Lee et al. |

OTHER PUBLICATIONS

Arridge, et al., "The theoretical basis for the determination of optical pathlengths in tissue: temporal and frequency analysis", "Phys. Med. Biol.", 1992, pp. 1531-1560, vol. 37.

Augustine, George J., "Combining patch-clamp and optical methods in brain slices", "Journal of Neuroscience Methods", 1994, pp. 163-169, vol. 54.

Banghart, Matthew, et al., "Light-activated ion channels for remote control of neuronal firing", "Nature Neuroscience", Nov. 21, 2004, pp. 1381-1386, vol. 7, No. 12.

Boyden, Edward S., et al., "Millisecond-timescale, genetically targeted optical control of neural activity", "Nature Neuroscience", Sep. 2005, pp. 1263-1268, vol. 8, No. 9.

Bureau, Ingrid, et al., "Precise Development of Functional and Anatomical Columns in the Neocortex", "Neuron", Jun. 10, 2004, pp. 789-801, vol. 42.

Chambers, James J., et al., "Light-Induced Depolarization of Neurons Using a Modified Shaker K+ Channel and a Molecular Photoswitch", "Journal of Neurophysiology", Jul 26, 2006, pp. 2792-2796, vol. 96.

Chance, et al., "Comparison of time-resolved and -unresolved measurements of deoxyhemoglobin in brain", "Proc. Nati. Acad. Sci. USA", Jul. 1988, pp. 4971-4975, vol. 85.

Deal, Walter J., et al., "Photoregulation of Biol. Activity by Photochromic Reagents, 3. Photoreg. of Bioelectricity by Acetylcholine Receptor INH", "Proc. Natl. Acad. Sci.", 1969, pp. 1230-1234, vol. 64, No. 4.

Desmurget, et al., "Movement Intention after Parietal Cortex Stimulation in Humans", "Science", May 8, 2009, pp. 811-813, vol. 324.

Dodt, H.-U., et al., "Circuitry of rat barrel cortex investigated by infrared-guided laser stimulation", "NeuroReport", Mar. 24, 2003, pp. 623-627, vol. 14, No. 4.

Dodt, H.-U., et al., "Precisely Localized LTD in the Neocortex Revealed by Infrared-Guided Laser Stimulation.", "Science", Oct. 1, 1999, pp. 110-113, vol. 286.

Eder, Matthias, et al. , "Neocortical Long-Term Potentiation and Long-Term Depression: Site of Expression Investigated by IR-Guided Laser Stim.", "Journal of Neuroscience", Sep. 1, 2002, pp. 7558-7568, vol. 22, No. 17.

Fork, Richard L., "Laser Stimulation of Nerve Cells in Aplysia", "Science, New Series", Mar. 5, 1971, pp. 907-908, vol. 171, No. 3974.

Haggard, "The Sources of Human Volition", "Science", May 8, 2009, pp. 731-733, vol. 324.

Izzo, et al., "Laser Stimulation of the Auditory Nerve", "Lasers in Surgery and Medicine", 2006, Publisher: Wiley-Liss, Inc.

Izzo, et al., "Selectivity of neural stimulation in the auditory system: a comparison of optic and electric stimuli", "Journal of Biomedical Optics", Mar./Apr. 2007, p. 021008 , vol. 12, No. 2.

Izzo, Agnella D., et al., "Optical Parameter Variability in Laser Nerve Stimulation: A Study of Pulse Duration, Repetition Rate, and Wavelength.", "IEEE Transactions on Biomedical Engineering", Jun. 2007, pp. 1108-1114, vol. 54, No. 6(1).

Maiorov, M., et al., "218 W quasi-CW operation of 1.83 um two-dimensional laser diode array", "Electronics Letters", Apr. 15, 1999, pp. 636-638, vol. 35, No. 8.

Nakagawa, Atsuhiro, et al., "Pulsed holmium:yttrium-aluminum-garnet laser-induced liquid jet as a novel dissection device in neuroendoscopic surgery", "J. Neurosurg.", Jul. 2004 , pp. 145-150, vol. 101.

Naples, et al., "A spiral nerve cuff electrode for peripheral nerve stimulation", "IEEE Trans Biomed Eng", Nov. 1988, pp. 905-916, vol. 35, No. 11.

Passos, D., et al., "Tissue phantom for optical diagnostics based on a suspension of microspheres with a fractal size distribution", "Journal of Biomedical Optics.", Nov.-Dec. 2005 , p. 064036, vol. 10, No. 6.

Princeton Lightwave (Company), "High Power Multimode Laser Arrays", "www.princetonlightwave.com/content/pli_high_power_multimode_laser_arrays.pdr", 2005.

Princeton Lightwave (Company), "High Power Water Cooled Laser Stack", "www.princetonlightwave.com", 2005.

Princeton Lightwave (Company), "High Power Water Cooled Laser Stack", "http://www.princetonlightwave.com/content/pli_high_power_multimode_laser_stacks.pdf", 2005 (downloaded 12-.

Princeton Lightwave (Company), "High Power Single Element Laser", "www.princetonlightwave.com/content/HP%20Single%20Element%20Laser%20version%202.pdf", 2005.

Rolfe, "In Vivo Near-Infrared Spectroscopy", "Annu. Rev. Biomed. Eng.", 2000, pp. 715-754 , vol. 2.

Schiefer, et al., "A Model of Selective Activation of the Femoral Nerve with a Flat Interface Nerve Electrode for a Lower Extremity Neuropr", "IEEE Trans Neural Syst Rehabil Eng", Apr. 2008, pp. 195-204, vol. 16, No. 2.

Schwartz, et al., "Auditory Brainstem Implants", "Neurotherapeutics: The Journal of the American Society for Experimental NeuroTherapeutics", Jan. 2008, pp. 128-136, vol. 5.

Tarler, et al., "Comparison of joint torque evoked with monopolar and tripolar-cuff electrodes", "IEEE Trans Neural Syst Rehabil Eng", 2003, pp. 227-235, vol. 11, No. 3.

Teudt, et al., "Optical Stimulation of the Facial Nerve: A New Monitoring Technique?", "The Laryngoscope", 2007, pp. 1641-1647, vol. 117, No. 9.

Vogel, Alfred, et al., "Mechanisms of pulsed laser ablation of biological tissues.", "Chemical Reviews", 2003, pp. 577-644, vol. 103, No. 2.

Wells, Jonathon, et al., "Application of Infrared Light for in vivo Neural Stimulation.", "Journal of Biomedical Optics ", Nov. 2005, pp. 064003-1 to 064003-12, vol. 10, No. 6.

Wells, Jonathon, et al., "Optical stimulation of neural tissue in vivo", "Optics Letters", Mar. 1, 2005, pp. 504-506, vol. 30, No. 5.

Wells, Jonathon D., et al., "Optically Mediated Nerve Stimulation: Identification of Injury Thresholds.", "Lasers in Surgery and Medicine", 2007, pp. 513-526, vol. 39.

Wells, Jonathon, et al., "Pulsed laser versus electrical energy for peripheral nerve stimulation", "Journal of Neuroscience Methods", 2007, pp. 326-337, vol. 163.

Yoo, et al., "Selective recording of the canine hypoglossal nerve using a multicontact flat interface nerve electrode", "IEEE Trans Biomed Eng", Aug. 2005, pp. 1461-1469, vol. 52, No. 8.

Zemelman, Boris V., et al., "Photochemical gating of heterologous ion channels: Remote control over genetically designated populations of neurons", "Proceedings of the National Academy of Sciences", Feb. 4, 2003, pp. 1352-1357, vol. 100, No. 3.

Zhang, Feng, et al., "Channelrhodopsin-2 and optical control of excitable cells", "Nature Methods", Sep. 21, 2006, pp. 785-792, vol. 3, No. 10.

Bernstein, Jacob G., et al., "Prosthetic systems for therapeutic optical activation and silencing of genetically-targeted neurons", "Proc Soc Photo Opt Instrum Eng.", May 5, 2008, vol. 6854: 68540H.

Han, Xue, et al., "Multiple-Color Optical Activation, Silencing, and Desynchronization of Neural Activity, with Single-Spike Temporal Resol", "PLoS ONE 2(3): e299. doi:10.1371/journal.pone.0000299", Mar. 2007, p. e299, No. 3, Publisher: www.plosone.org.

Huang, Ying-Ying, et al., "Biphasic Dose Response in Low Level Light Therapy", "Dose-Response", 2009, pp. 358-383, vol. 7.

* cited by examiner

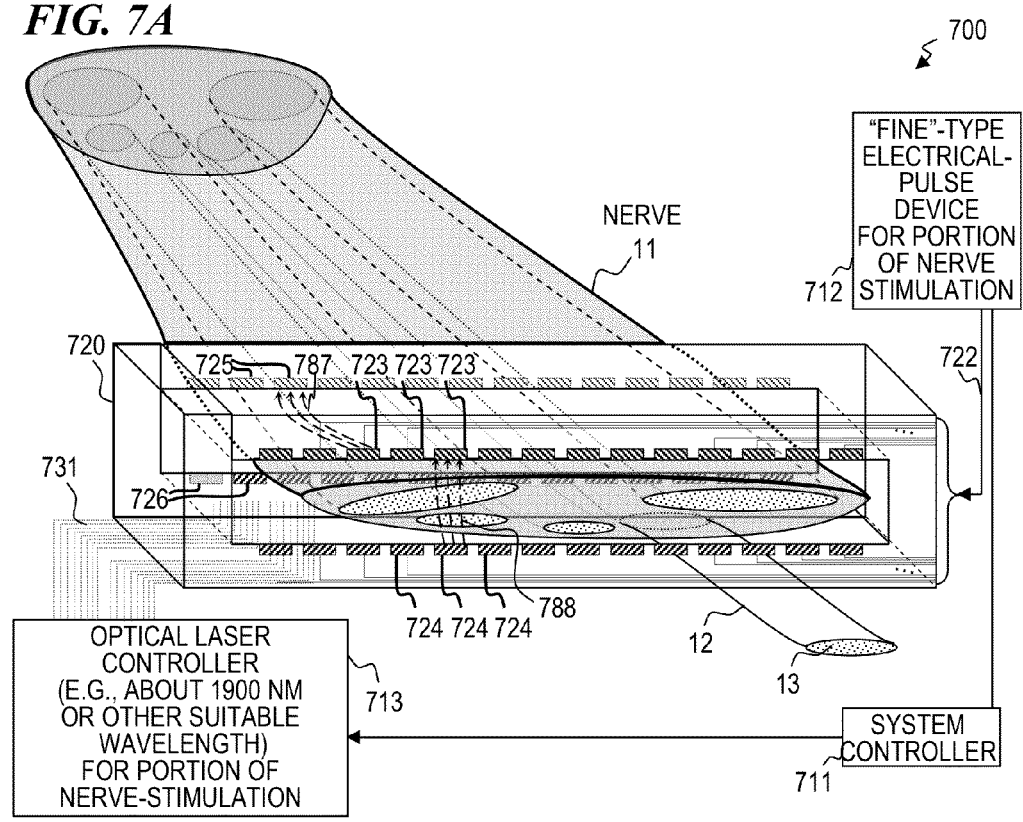
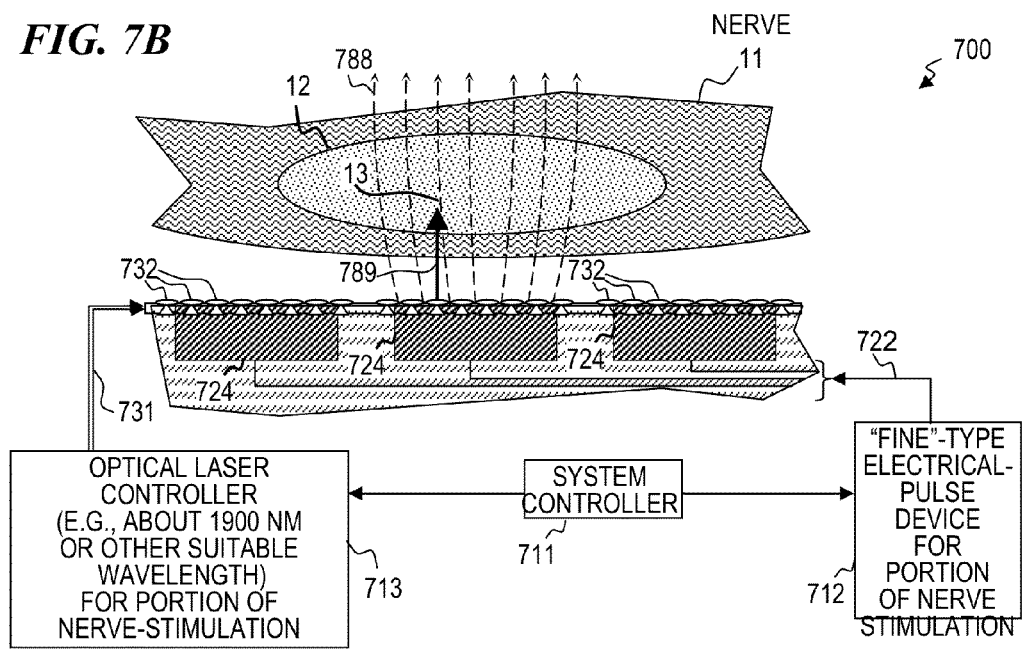

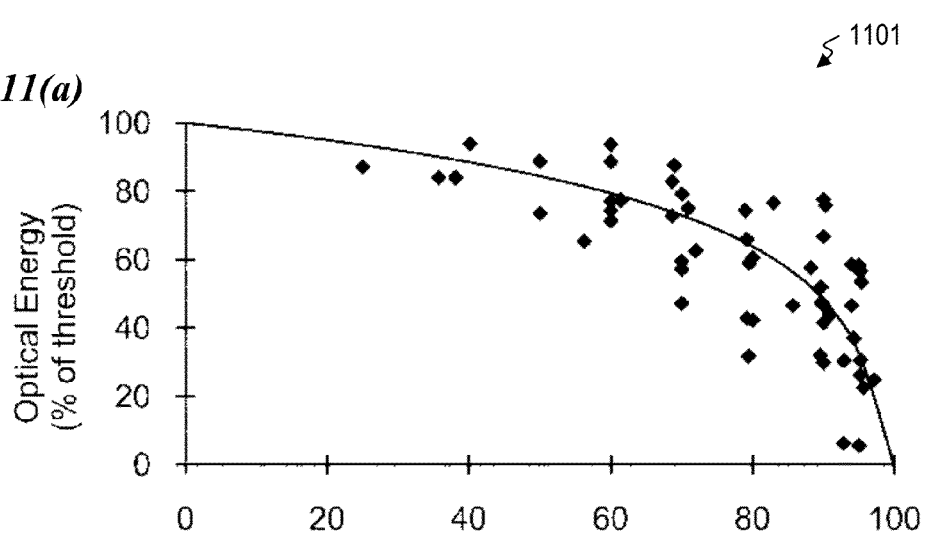
FIG. 11(a)
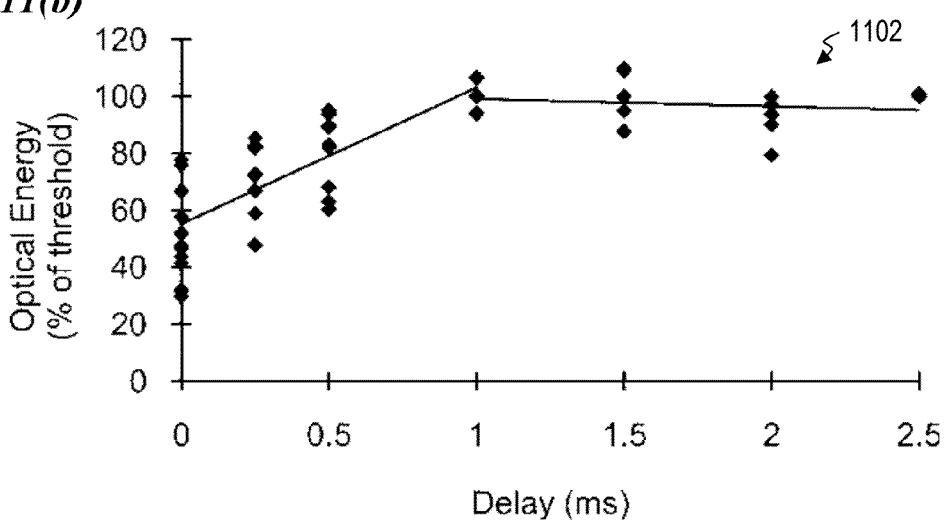
FIG. 11(b)
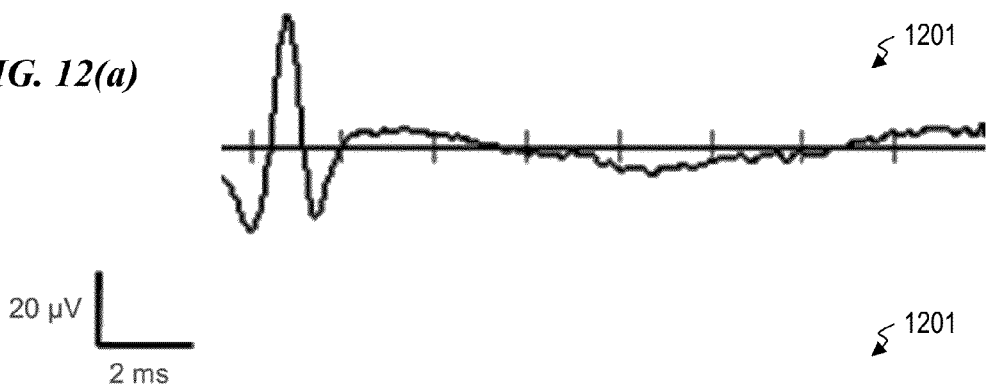
FIG. 12(a)
20 μV
2 ms
FIG. 12(b)

*FIG. 15(a)*
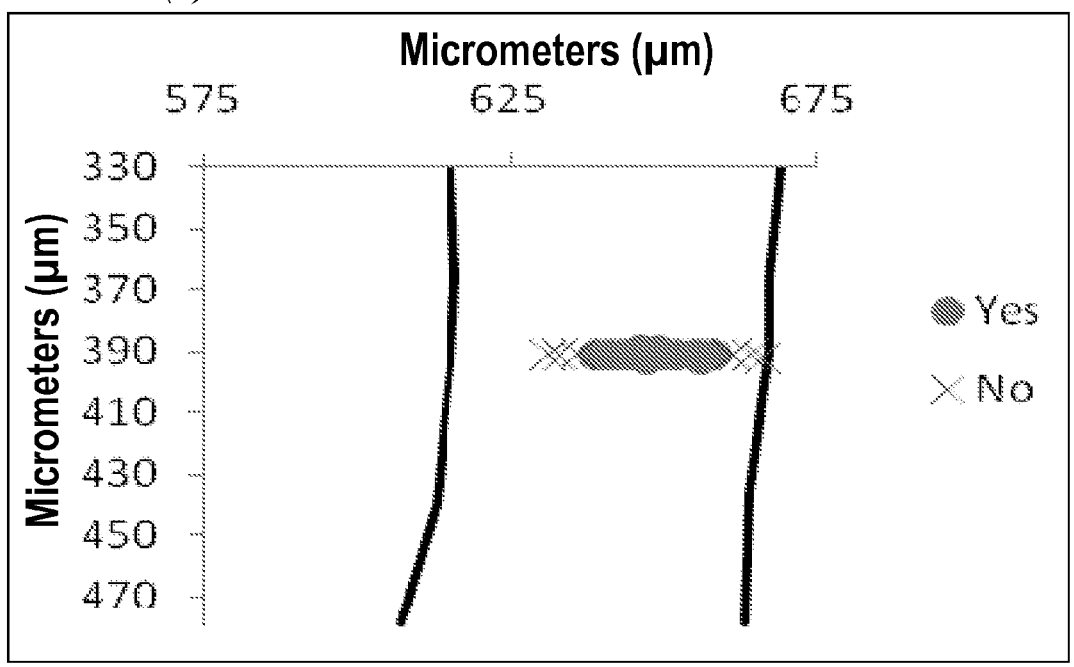
*FIG. 15(b)*
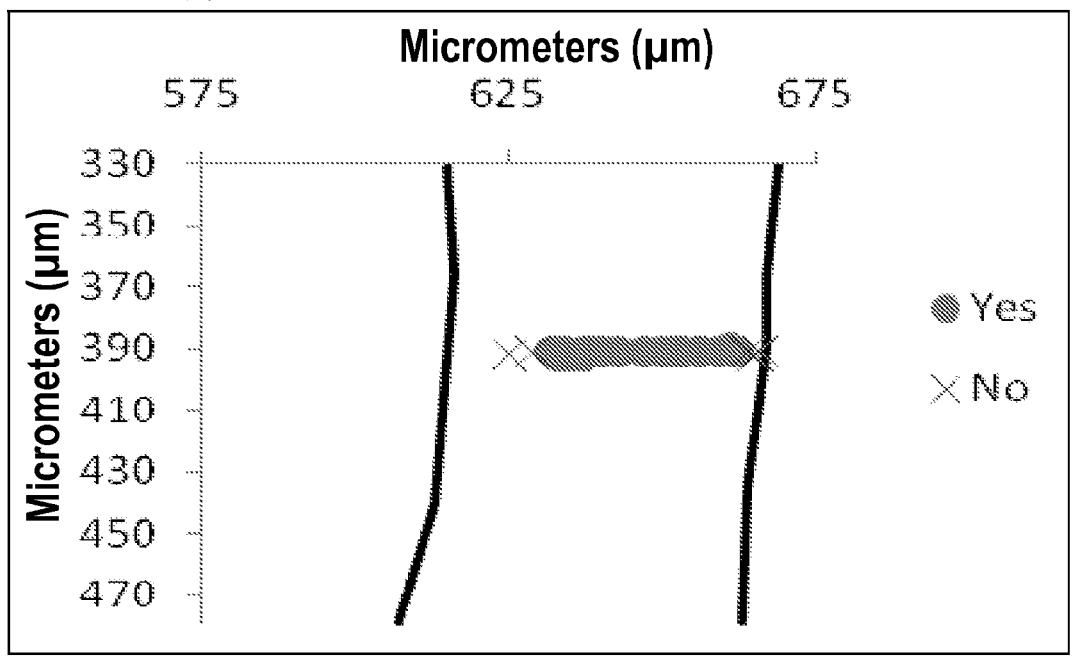
*FIG. 15(c)*
| Stimulus Strength | ROE Size (µm) | Animals, Nerves, Measurements |
|---|---|---|
| 1.78 J/cm² | 51.7 ± 18.0 | 3, 3, 13 |
| 4.71 J/cm² | 95.0 ± 13.9 | 4, 4, 17 |

*FIG. 19*

| | Increasing Radiant Exposure→→→ | | Decreasing Radiant Exposure→→→ | |
|---|---|---|---|---|
| Stimulation: | Starts | Stops | Starts | Stops |
| Avg. ± SD (J/cm²) | 1.50 ± 0.27 | 5.81 ± 0.89 | 5.51 ± 0.91 | 1.26 ± 0.35 |

METHOD AND NERVE STIMULATOR USING SIMULTANEOUS ELECTRICAL AND OPTICAL SIGNALS

CROSS-REFERENCE TO RELATED APPLICATIONS

This is a continuation-in-part under 37 C.F.R. §153(b)(2) of, and claims benefit under 35 U.S.C. §120 of, U.S. patent application Ser. No. 12/573,848 titled "Nerve Stimulator and Method Using Simultaneous Electrical and Optical Signals" filed Oct. 5, 2009 (which issued as U.S. Pat. No. 8,160,696 on Apr. 17, 2012), which claims benefit under 35 U.S.C. §119(e) to U.S. Provisional Patent Application No. 61/102,811 filed on Oct. 3, 2008, titled "Nerve Stimulator and Method Using Simultaneous Electrical and Optical Signals," each of which is herein incorporated in its entirety by reference.

This application claims priority benefit under 35 U.S.C. §119(e) to U.S. Provisional Patent Application No. 61/298,543, titled "Combined Optical and Electrical Stimulation of Neural Tissue in vivo," filed Jan. 26, 2010, by some of the inventors of the present invention.

This is related to U.S. patent application Ser. No. 12/018,185, titled "Hybrid Optical-Electrical Probes," filed Jan. 22, 2008, by some of the inventors of the present invention (which issued as U.S. Pat. No. 7,883,536 on Feb. 8, 2011), which is herein incorporated in its entirety by reference.

This invention is also related to prior:
U.S. Pat. No. 7,736,382 issued Jun. 15, 2010 to James S. Webb et al., titled "Apparatus and Method for Optical Stimulation of Nerves and Other Animal Tissue";
U.S. patent application Ser. No. 11/536,639 filed Sep. 28, 2006, titled "Miniature Apparatus and Method for Optical Stimulation of Nerves and Other Animal Tissue"; (which issued as U.S. Pat. No. 7,988,688 on Aug 2, 2011);
U.S. patent application Ser. No. 11/536,642 filed Sep. 28, 2006, titled "Apparatus and Method for Stimulation of Nerves and Automated Control of Surgical Instruments";
U.S. Provisional Patent Application No. 60/872,930 filed Dec. 4, 2006, titled "Apparatus and Method for Characterizing Optical Sources Used with Human and Animal Tissues";
U.S. patent application Ser. No. 11/948,912 filed Nov. 30, 2007, titled "Apparatus and Method for Characterizing Optical Sources Used with Human and Animal Tissues";
U.S. Provisional Patent Application No. 60/884,619 filed Jan. 11, 2007, titled "Vestibular Implant Using Infrared Nerve Stimulation"; and
U.S. patent application Ser. No. 11/971,874 filed Jan. 9, 2008, titled "Method and Vestibular Implant Using Optical Stimulation of Nerves"; (which issued as U.S. Pat. No. 8,012,189 on Sep. 6, 2011);
each of which is incorporated herein by reference in its entirety.

STATEMENT AS TO RIGHTS UNDER FEDERALLY-SPONSORED RESEARCH

This invention was made with Government support awarded by the United States National Institute of Health under Contract No. R01 NS052407-01 and Contract No. R44 NS051926-02 (EDJ). Accordingly, the U.S. Government has certain rights in this invention.

FIELD OF THE INVENTION

The invention relates generally to tissue electro-optics (interactions of electricity and light with human or non-human animal tissue), and more particularly to methods, and both implantable and non-invasive apparatus for stimulating animal tissue in vivo, for example, stimulating and triggering a nerve action potential in nerves (e.g., nerves or neurons of the peripheral or central nervous system in animals, and in particular, humans) utilizing both electrical-signal and optical-signal stimulation.

BACKGROUND OF THE INVENTION

As a convention used herein, a nerve will be defined as a collection of individual nerve fibers (i.e., axons) of individual nerve cells (neurons) that together form an integrated pathway within the nervous system. Subsets of the individual nerve fibers are each bundled into one of a plurality of fascicles that together form the nerve. Action potentials can occur in the axon portion of individual nerve cells. A series of individual nerve fibers that together form an integrated signal pathway starting at a sensory-receptor nerve ending and extending to the brain will be referred to as a sensory-nerve pathway, a series of individual nerve fibers that together form an integrated signal pathway starting at the brain and extending to a muscle cell will be referred to as a motor-nerve pathway. Within each fascicle of a nerve, there will typically be a plurality of sensory-nerve pathways and a plurality of motor-nerve pathways, wherein the number of sensory-nerve pathways will typically be about fifteen times as many as the number of motor-nerve pathways. As well, a series of individual nerve fibers may together form an integrated pathway starting at one of various internal organs and ending in the brain, with then other series of individual nerve fibers together forming an integrated pathway starting at the brain and extending to some internal end organ (such as the digestive tract, the heart, or blood vessels) as part of the autonomic nervous system; and a series of individual nerve fibers may together form an integrated pathway within the brain referred to as a tract. As used herein, a nerve bundle or fascicle refers to a collection of nerve fibers that subserve a like function (e.g., a fascicle may support a plurality of different motor-nerve pathways and thus motor-control signals needed for the muscles for a hand grasp, for example; similarly the same and/or a nearby fascicle may support a plurality of corresponding sensory-nerve pathways and thus sensory signals that provide the brain with feedback for the hand grasp).

FIG. 1A is a schematic diagram 101 of a nerve (adapted from www.mayoclinic.org/peripheral-nerve-tumors-benign/diagnosis.html). A nerve 11 contains fascicles (bundles) 12 of individual nerve fibers 13 of neurons. FIG. 1B is a schematic diagram 102 of the structure of a spinal nerve 11 that includes its surrounding epineurium 14, which includes connective tissue and blood vessels 15, one or more fascicles (fasciculus) 12, each of which is surrounded by perineurium 17. Within a fascicle 12 is a plurality of axons 13 each having a myelin sheath surrounded by endoneurium tissue 18 (credit to internet sources: en.wikipedia.org/wiki/Nerve_fascicle and trc.ucdavis.edu/mjguinan/apc100/modules/nervous/pns/nervel/nervel.html).

Typically a nerve action potential (NAP) or compound nerve action potential (CNAP), which is a summated potential of the action potentials in all the axons in a nerve, as a signal travels down a nerve, is sensed using an electrical sensor probe that detects the waveform of a voltage associated with the NAP. Accordingly, traditional methods used electrical stimulation to trigger a NAP signal in a nerve. One disadvantage of using electrical stimulation is that the electrical signal applied to stimulate one nerve fiber will generally stimulate a plurality of surrounding nerve fibers (even nerve fibers in other fascicles than the fascicle containing the nerve of interest) to also trigger NAP signals in those other nerve fibers: Present neuromodulation technology is based on the generation of electric fields around the neuron. The spatial differential voltage along the axons, commonly referred to as the driving function, results in a depolarization of the neural membrane. This depolarization results in action-potential generation, which is then transmitted to target organ where it produces a characteristic effect. The electric field is significantly influenced by the electrical impedance of the tissues.

Extraneural electrodes, such as the Flat Interface Nerve Electrode (FINE), have demonstrated fascicular selectivity (to within about 400 μm (400 microns)). The perineurium, which surrounds a plurality of nerve axons and defines the individual fascicle, typically has a high impedance. This causes the voltage distribution to be fairly uniform within at least a portion of a fascicle (while also being electrically isolated from neighboring fascicles), hence limiting the possibility of sub-fascicular selectivity when using electrical stimulation. While the spatial selectivity of these extraneural electrodes (such as the FINE) has been successfully shown to produce functional neural stimulation in clinical applications, neuromodulation applications such as hand-grasp, sensory-stimulation applications for artificial prostheses, and control of autonomic functions such as cardiac rate via Vagus-nerve stimulation, require, in some cases, selection of at most one fascicle and even greater sub-fascicular spatial selectivity (i.e., selection of a single axon or just a few axons but not all the axons in the single fascicle) than is typically possible using electrical stimulation alone, such that separate signals are delivered to different axons within one fascicle.

Prior Innovations To Increase Selectivity With Electrical Stimulation:

A number of innovative electrode designs have advanced spatial selectivity for stimulation of nerve fascicles. The spiral electrode, introduced in 1988 (Naples, G. G., J. T. Mortimer, et al. (1988), "A spiral nerve cuff electrode for peripheral nerve stimulation," IEEE Trans Biomed Eng 35(11): 905-16), has been shown in animal models to cause negligible changes in nerve morphology (Grill, W. M. and J. T. Mortimer (1998), "Stability of the input-output properties of chronically implanted multiple contact nerve cuff stimulating electrodes," IEEE Trans. Rehabil. Eng. 6(4): 364-73; Grill, W. M. and J. T. Mortimer (2000), "Neural and connective tissue response to long-term implantation of multiple contact nerve cuff electrodes," J Biomed Mater Res 50(2): 215-26) and was capable of selective stimulation (Sweeney, J. D., D. A. Ksienski, et al. (1990), "A nerve cuff technique for selective excitation of peripheral nerve trunk regions," IEEE Trans Biomed Eng 37(7): 706-15; Sweeney, J. D., N. R. Crawford, et al. (1995), "Neuromuscular stimulation selectivity of multiple-contact nerve cuff electrode arrays," Med. Biol. Eng. Comput. 33(3 Spec. No.): 418-25; Tarler, M. D. and J. T. Mortimer (2003), "Comparison of joint torque evoked with monopolar and tripolar-cuff electrodes," IEEE Trans Neural Syst Rehabil Eng 11(3): 227-35). Twenty-one spiral electrodes have been implanted in five human subjects for periods between three months and three years without any observable loss of neural function that would be indicative of chronic damage. These electrodes have demonstrated moderate selectivity sufficient for neuromodulation in the upper and lower extremities. More refined applications require greater selectivity than currently achieved with the spiral electrode.

The Flat Interface Nerve Electrode (FINE), introduced in 2002 (Tyler, D. J. and D. M. Durand (2002), "Functionally selective peripheral nerve stimulation with a flat interface nerve electrode," IEEE Trans Neural Syst Rehabil Eng 10(4): 294-303; also described in U.S. Pat. No. 6,456,866 issued to Tyler et al., discussed below), has been shown in animal models to attain a high level of fascicular stimulation and recording selectivity with negligible changes in nerve morphology (Tyler and Durand 2002 ibid.; Leventhal, D. K. and D. M. Durand (2004), "Chronic measurement of the stimulation selectivity of the flat interface nerve electrode," IEEE Trans Biomed Eng 51(9): 1649-58; Tyler, D. J. and D. M. Durand (2003), "Chronic response of the rat sciatic nerve to the flat interface nerve electrode," Ann Biomed Eng 31(6): 633-42; Yoo, P. B. and D. M. Durand (2005), "Selective recording of the canine hypoglossal nerve using a multicontact flat interface nerve electrode," IEEE Trans Biomed Eng 52(8): 1461-9). Studies involving computational modeling have shown that the FINE electrode can selectively activate individual muscles within the femoral nerve stimulation (Schiefer, M. A., R. J. Triolo, et al. (2008), "A Model of Selective Activation of the Femoral Nerve with a Flat Interface Nerve Electrode for a Lower Extremity Neuroprosthesis," IEEE Trans Neural Syst Rehabil Eng). The femoral nerve is composed of up to forty-three (43) fascicles in the dog or cat model, with several fascicles innervating each muscle. Electrical stimulation with the spiral and FINE electrode designs can be effective, but these electrode designs are limited in their ability to stimulate each of the forty-three (43) fascicles individually. Anatomic studies of the human upper extremity nerves show that these nerves have a large number of fascicles. Higher-precision spatial selectivity of individual nerve fascicles would enable more refined function to neuromodulation therapies, many of which still have ample opportunity for improved control of function.

To further increase fascicle and subfascicular selectivity, intrafascicular electrodes place stimulation electrodes within the individual nerve fascicles. Intraneural electrode arrays, such as the Utah Slanted Electrode Array (USEA) (see Branner, A. and R. A. Normann (2000), "A multielectrode array for intrafascicular recording and stimulation in sciatic nerve of cats," Brain Res Bull 51(4): 293-306) and polymer longitudinal intrafascicular electrode (polyLIFE) (see Malmstrom, J. A., T. G. McNaughton, et al. (1998), "Recording properties and biocompatibility of chronically implanted polymer-based intrafascicular electrodes," Ann Biomed Eng 26(6): 1055-64), penetrate through the perineurium to place contacts within the fascicles, in direct contact with axons. This has been demonstrated to be effective for selective stimulation, although there is evidence that this approach may cause damage to the nerve. Violation of the perineurium typically compromises the blood-nerve-barrier and other protective mechanisms of the perineurium. Owing to the simplicity and proven chronic experience of the circumneural approaches, an alternative method of stimulation that can improve the fascicular and subfascicular selectivity beyond the FINE would be a significant alternative to intrafascicular stimulation.

An emerging technology that significantly increases the spatial precision of nerve stimulation uses pulsed infrared light to reliably elicit neural action potentials in a non-contact manner (Wells, J. D., Kao, C., Jansen, E. D., Konrad, P., Mahadevan-Jansen, A., "Application of Infrared Light for in vivo Neural Stimulation," Journal of Biomedical Optics, 2005; Wells, J. D., Kao, C., Mariappan, K., Albea, J., Jansen, E. D., Konrad, P., Mahadevan-Jansen, A., "Optical Stimulation of Neural Tissue in vivo," Optics Letters, 2005. 30(5): p. 504-507, (collectively hereinafter "Wells et al. 2005")). Infrared nerve stimulation (IRNS) was a result of an amalgamation of the fields of biomedical optics and neuroscience at Vanderbilt University. A systematic wavelength study using Vanderbilt University's tunable free-electron laser (2-10 μm) revealed that while most infrared wavelengths are capable of IRNS, 2.1 μm and 4 μm demonstrate the highest safety ratio for stimulation (safety ratio=laser radiant exposure required for thermal damage/laser radiant exposure required for stimulation resulting in a visible muscle twitch when stimulating the rat sciatic nerve). It was shown that IRNS using optimized laser parameters has a set of fundamental advantages over electrical stimulation that include high spatial selectivity, the ability to generate action potentials free of electrical stimulus artifact, non-contact stimulus delivery (even through bone), and MRI compatibility (Wells et al. 2005). These benefits make IRNS particularly attractive for clinical applications requiring precise, localized stimulation, such as use with diagnostic tools, neuroprostheses, and neurocognitive therapeutic devices.

Small, spatially localized neuronal populations have been stimulated with laser energy, which differs from the larger neuron populations that are stimulated by contemporary neural interfaces that use electrical current (Wells et al. 2005; Wells, J. D., Kao, Konrad, P., Mahadevan-Jansen, A., and Jansen, E. D. (2006), "Biophysical mechanisms responsible for pulsed low-level laser excitation of neural tissue," Proc. SPIE 6084, 60840X (2006), DOI:10.1117/12.655239 (hereinafter "Wells et al. 2006"). Although important advances in spatial selectivity have been made in electrical stimulation (described above), the precision of electrical-stimulation techniques is fundamentally limited by the fact that electrical current spreads in a conductive medium (e.g., within a fascicle, since the tissue providing primary electrical insulation to prevent loss is the perineurium that surrounds the fascicle at its perimeter). A laser, on the other hand, offers a spatially restricted distribution of light that is predictable by the diffraction-limited spot size in the lateral direction, and a combination of the laser wavelength and the optical properties of the target tissue in the axial direction. This can have profound implications when applied to neuroprostheses. FIG. 2A and FIG. 2B illustrate the capability of optical stimulation to selectively activate specific fascicles within the main rat sciatic nerve to target specific muscle groups such as the gastrocnemius, while yielding no response from adjacent fibers that innervate the biceps femoris. Selective recruitment of nerve fibers is indicated by comparing the relative magnitudes of nerve and muscle potentials (FIG. 2A and FIG. 2B) elicited from optical and electrical stimulation. (Specifically, FIG. 2A and FIG. 2B show spatial targeting of IRNS. FIG. 2A shows threshold compound muscle action potential (CMAP) response from electrical stimulation of the main branch of the sciatic nerve proximal to the first branch point with 1.02 A/cm$^2$. FIG. 2B shows corresponding results from threshold optical stimulation (0.4 J/cm$^2$) of specific target nerve fibers that innervate the gastrocnemius, with no response from adjacent nerve fibers (quiet biceps femoris). The distance from the stimulation spot to recording electrodes was held constant for trials involving each modality (optical IRNS, electrical, or both) (as shown in these graphs, these signals were amplified with a gain=1000).) Results from these studies demonstrate subfascicular selectivity using infrared nerve stimulation (IRNS), thus providing motivation for applying this technique to neuroprostheses with the vision of greater selectivity and improved clinical outcomes in restoration of function.

Thus, recently, very specific optical-stimulation waveforms and wavelengths have been used to stimulate a nerve to trigger a NAP signal. Delivering such optical energy using optical fibers has the advantages of the very small structures of the optical fiber and the very small target areas to which the optical signal can be confined, which provides a medical practitioner the ability to stimulate one or only a few nerve fascicles within a nerve bundle without triggering NAPs in neighboring fascicles to which the medical practitioner does not wish to deliver triggering stimulation. Typically, a relatively high fluence of optical energy is required to trigger a NAP. In some embodiments, the present invention provides ability to stimulate spots that are much smaller than the fascicle and thus trigger NAPs on a subfascicular basis.

While research data suggest that infrared-nerve-stimulation (IRNS) technology has distinct advantages over other standard stimulation methods, there are a number of engineering challenges and obstacles that must be overcome before this technology matures to the point of clinical utility. A comprehensive set of survival studies to identify upper limits for safe laser intensities in the mammalian peripheral nerve have been undertaken. A low-frequency, short-duration stimulation protocol (2 pulses per second, 20 pulses) was applied to 50 nerves using a broad range of radiant exposures above stimulation threshold (0.4-1.4 J/cm$^2$) with the research-grade Capella R-1850 infrared nerve stimulator (available from Lockheed Martin Aculight Corporation, 22121 20th Avenue S.E., Bothell, Wash. 98021), which provides improved nerve selectivity, no electrical artifact, and non-contact operation. Upper limits for radiant exposure to stimulate the rat sciatic nerve without thermal injury were evaluated using histology both 3-5 days (n=34) and 14 days (n=16) following stimulation, for assessment of any delayed neuropathology (such as Wallerian degeneration) in the stimulated nerves. An expert pathologist specializing in laser-tissue interactions reported any sign of epineurial or axonal damage as a 1, while if there were no detected signs of damage, this was reported as a 0 (zero). Statistical analyses (obtained using a software program (Probit v2.1.2, Litton TASC, San Antonio, Tex., 1998) for analyzing yes/no data on a log scale was applied to the data collected from survival experiments. Results from histological analysis (yes=damage, no=no damage) were input into the software program such that the output yielded the probability of damage as a function of laser radiant exposure. The 50% probability of damage was also determined in these computations) are summarized in graph 300 in FIG. 3, where the probability of damage is graphed as a function of radiant exposure for 3-to-5-day, and two-week survival experiments. (Specifically, FIG. 3 shows probability of damage as a function of laser radiant exposure compared to the stimulation threshold. Results from statistical analysis show the probability of histological nerve damage versus the laser radiant exposure from data collected from 3-to-5-day survival studies (crosses, n=34) and 14-day survival studies (triangles, n=16). The results from studies to determine the range of threshold radiant exposures needed for stimulation are shown for comparison with 95% confidence intervals. This graph illustrates that a safe margin exists between the maximum laser radiant exposures required to stimulate and the minimum radiant exposures necessary for damage (P(damage)=0%). These results quantify the upper limits for brief, low-repetition-rate optical stimulation of the rat sciatic nerve.)

The stimulation threshold (e.g., in some embodiments, this is the level of stimulation that achieves a 0.5 probability for stimulation—a response occurring upon 50% of stimulation occasions) in the rat sciatic nerve was shown to be 0.41+/−0.07 J/cm$^2$ over a large number of trials (n=32). The radiant exposure with a 0.5 probability of thermal damage (damage occurring on 50% of occasions after a 2-Hz-and-20-pulses protocol as described in the previous paragraph) is 0.90 J/cm$^2$ in the 3-5-day survival studies and 0.95 J/cm$^2$ from two-week survivors. In some experiments, a fluence of less than 0.70

J/cm² resulted in no thermal damage. While these data suggest that a small, but clearly defined "safe zone" exists when using a low-frequency, short-duration stimulation protocol, the approximately two-times (~2×) safety margin may need to be improved before clinical implementation of this technique. In contrast, the safety margin for damage to stimulation thresholds in electrical stimulation is greater than fifty times (50×) in most peripheral nerves.

Other experiments report the upper limit for safe laser-stimulation repetition rate occurs near five (5) pulses per second and that the maximum duration for constant low-repetition-rate stimulation (two (2) pulses per second) is about four (4) minutes with adequate tissue hydration (Wells et al. 2005). It should be pointed out that the scenario above is specific to stimulation of the rat sciatic nerve (a peripheral nerve) and eliciting a visible motor twitch in the down-stream muscles. In other work, stimulation thresholds that are nearly two orders of magnitude lower have been reported while stimulating the spiral ganglion cells in the gerbil cochlea (Izzo, Richter et al., "Laser Stimulation of the Auditory Nerve," Lasers in Surgery and Medicine, Wiley-Liss, Inc, 2006; Izzo, Suh et al., "Selectivity of neural stimulation in the auditory system: an comparison of optic and electric stimuli," Journal of Biomedical Optics, 12(2), 021008 (March/April 2007); Izzo, Walsh et al., "Optical Parameter Variability In Laser Stimulation: a study of pulse duration, repetition rate, and wavelength," IEEE Trans. Biomed. Eng., 2007 June; 54(6 Pt 1):1108-14). In those experiments it was also shown that continuous stimulation at 300 Hz for up to six hours did not result in reduction in CNAP signals from the stimulated cells. Another experiment on gerbil nerves was reported by Teudt et al. who exposed the gerbil facial nerve to 250-microsecond pulses of 2.12-micron-wavelength radiation from a Ho:YAG laser via a 600-micron-diameter optical fiber at a repetition rate of 2 Hz with radiant exposures of between 0.71 J/cm² and 1.77 J/cm² to trigger compound muscle action potentials (CmAPs) (Teudt et al., "Optical Stimulation of the Facial Nerve: A New Monitoring Technique?", *The Laryngoscope* VOL: 117(9); p. 1641-7/200'709/, Lippencott Williams and Wilkins, 2007). Histology by Teudt et al. 2007 revealed tissue damage at radiant exposures of 2.2 J/cm², but no apparent damage at radiant exposures of 2.0 J/cm².

Increases in nerve-tissue temperature during laser stimulation may result in nerve-tissue damage. FIGS. 4A-4D show graphs of steady-state maximum temperature increase in nerve tissue from Ho:YAG laser stimulation. (Graph 401 of FIG. 4A: Temperature rise from 0.45 J/cm² radiant exposure pulses at 2-Hz stimulation frequency. Graph 402 of FIG. 4B: Temperature rise from 0.65 J/cm² radiant exposures at 2-Hz stimulation frequency. Graph 403 of FIG. 4C: Temperature rise from 0.41 J/cm² threshold radiant exposures at 5-Hz stimulation frequency. Graph 404 of FIG. 4D: Temperature rise from 0.63 J/cm² threshold radiant exposures at 5-Hz stimulation frequency.) The resultant heat load in tissue (measured via IR thermography) during low-frequency stimulation (graph 401 of FIG. 4A) has adequate time to diffuse out of the irradiated zone via conduction and other heat-transfer mechanisms. However, as indicated in graph 403 of FIG. 4C and graph 404 of FIG. 4D showing higher-frequency stimulation, temperature superposition will begin to occur at repetition rates greater than about 4 to 5 Hz, as the tissue requires slightly greater than 200 msec (milliseconds) to return to baseline temperature, since the thermal diffusion-time constant is ~90 msec under these conditions. At repetition rates greater than 5 Hz tissue-temperature changes will become additive with each ensuing laser pulse, and resulting tissue damage may begin to occur with prolonged constant stimulation. These data also indicate that amount of temperature rise and the time to reach a steady-state temperature are dependent on the radiant exposure level. At lower radiant exposures the rise in temperature is smaller and reaches a steady-state temperature in a shorter time. What is needed is a means to reduce the radiant exposure levels required for reliable IRNS, which would greatly reduce the heat load (thus reducing the potential for tissue damage) and significantly advance the implementation of IRNS technology in highly precise neurostimulation devices.

U.S. Pat. No. 7,225,028 issued to Della Santina et al. on May 29, 2007, and titled "Dual Cochlear/Vestibular Stimulator with Control Signals Derived from Motion and Speech Signals," is incorporated herein by reference. Della Santina et al. describe a system for treating patients affected both by hearing loss and by balance disorders related to vestibular hypofunction and/or malfunction, which includes sensors of sound and head movement, processing circuitry, a power source, and an implantable electrical stimulator capable of stimulating areas of the cochlea and areas of the vestibular system.

U.S. Patent Application Publication No. US 2007/0261127 A1 filed Jul. 24, 2006 by Edward S. Boyden and Karl Deisseroth, titled "LIGHT-ACTIVATED CATION CHANNEL AND USES THEREOF"; U.S. Patent Application Publication No. US 2007/0054319 A1 filed Jul. 24, 2006 by Edward S. Boyden and Karl Deisseroth, titled "LIGHT-ACTIVATED CATION CHANNEL AND USES THEREOF"; and U.S. Patent Application Publication No. US 2007/0053996 A1 filed Jul. 24, 2006 by Edward S. Boyden and Karl Deisseroth, titled "LIGHT-ACTIVATED CATION CHANNEL AND USES THEREOF," are all incorporated herein by reference. These describe compositions and methods for light-activated cation channel proteins and their uses within cell membranes and subcellular regions. They describe proteins, nucleic acids, vectors and methods for genetically targeted expression of light-activated cation channels to specific cells or defined cell populations. In particular the description provides millisecond-timescale temporal control of cation channels using moderate light intensities in cells, cell lines, transgenic animals, and humans. The optically generated electrical spikes in nerve cells and other excitable cells are useful for driving neuronal networks, drug screening, and therapy.

U.S. Pat. No. 6,456,866, which issued to Tyler et al. on Sep. 24, 2002, titled "Flat interface nerve electrode and a method for use," is incorporated herein by reference. Tyler et al. describe a flat interface nerve electrode (FINE) and a method for its use. The electrode provides a plurality of conductive elements embedded in a non-conductive cuff structure, which acts to gently and non-evasively redefine the geometry of a nerve through the application of a force so as to apply pressure to a nerve in a defined range. The cuff has an opening, which is elongated relative to the diameter of the nerve to which it is applied. Preferably, the cuff is constructed from an elastic bio-compatible material having top and bottom beam members configured to define a nerve opening. The cuff is open at one side and has a connection at the other side which results in a spring force being applied through the surfaces of the nerve opening to the subject nerve. During implantation the open sides of the cuff are closed so as to capture the nerve in the cuff. As the nerve is reshaped, specific nerve axons become more easily addressed through the epineurium by the embedded conductive elements.

U.S. Pat. No. 6,748,275, which issued to Lattner et al. on Jun. 8, 2004, and titled "Vestibular Stimulation System and Method," is incorporated herein by reference. Lattner et al. describe an apparatus and method in which the portions of the labyrinth associated with the labyrinthine sense and/or the nerves associated therewith are stimulated to perform at least one of the following functions: augment or control a patient's respiratory function, open the patient's airway, induce sleep, and/or counteract vertigo.

U.S. Pat. No. 7,004,645, which issued to Lemoff et al. on Feb. 28, 2006, and titled "VCSEL array configuration for a parallel WDM transmitter," is incorporated herein by reference. Lemoff et al. describe VCSEL array configurations. WDM is wavelength-division multiplexing. Transmitters that use several wavelengths of VCSELs are built up out of multiple die (e.g., ones having two-dimensional single-wavelength monolithic VCSEL arrays) to avoid the difficulty of manufacturing monolithic arrays of VCSELs with different optical wavelengths. VCSEL configurations are laid out to insure that VCSELs of different wavelengths that destined for the same waveguide are close together.

U.S. Pat. No. 7,116,886, which issued to Colgan et al. on Oct. 3, 2006, and titled "Devices and methods for side-coupling optical fibers to optoelectronic components," is incorporated herein by reference. Colgan et al. describe optical devices and methods for mounting optical fibers and for side-coupling light between optical fibers and VCSEL arrays using a modified silicon V-groove, or silicon V-groove array, wherein V-grooves, which are designed for precisely aligning/spacing optical fibers, are "recessed" below the surface of the silicon. Optical fibers can be recessed below the surface of the silicon substrate such that a precisely controlled portion of the cladding layer extending above the silicon surface can be removed (lapped). With the cladding layer removed, the separation between the fiber core(s) and optoelectronic device(s) can be reduced resulting in improved optical coupling when the optical fiber silicon array is connected to, e.g., a VCSEL array.

U.S. Pat. No. 7,031,363, which issued to Biard et al. on Apr. 18, 2006, and titled "Long wavelength VCSEL device processing," is incorporated herein by reference. Biard et al. describe a process for making a laser structure such as a vertical-cavity surface-emitting laser (VCSEL). The VCSEL designs described include those applicable to the 1200 to 1800 nm wavelength range.

U.S. Pat. No. 6,546,291, which issued to Merfeld et al. on Apr. 8, 2003, titled "Balance Prosthesis," is incorporated herein by reference. Merfeld et al. describe a wearable balance prosthesis that provides information indicative of a wearer's spatial orientation. The balance prosthesis includes a motion-sensing system to be worn by the wearer and a signal processor in communication with the motion-sensing system. The signal processor provides an orientation signal to an encoder. The encoder generates a feedback signal on the basis of the estimate of the spatial orientation provides that signal to a stimulator coupled to the wearer's nervous system.

U.S. Pat. No. 6,171,239, which issued to Humphrey on Jan. 9, 2001 titled "Systems, methods, and devices for controlling external devices by signals derived directly from the nervous system," is incorporated herein by reference. Humphrey describes a system to control prostheses and other devices with signals received by sensors implanted directly in the brain or other parts of the nervous system of a subject/patient and transmitted to an external receiver. The system has sensors in the form of bundles of small, insulated, flexible wires, configured in a parallel or twisted array, which are used to receive multicellular signals from small clusters of neurons. A new "calibration/adaptation" system is developed, in which the neural signals are cross-correlated with the parameters of a set of standardized or model movements as the subject/patient attempts to emulate the model movements, and on the basis of the correlations the neural signals that are best suited for control of the corresponding movement or movement parameter of the external device are selected. Periodic use of this calibration system compensates for or adapts to uncontrolled changes in neural signal parameters over time, and therefore results in re-selection of the optimal neural channels for better device control. Artificial neural nets are used for mapping the selected neural signals onto appropriate movements or control parameters of the external device.

Effective, specific and precise stimulation of selected nerves remains a problem. Improved apparatus and methods are needed to diagnose and/or treat various problems in animals (including humans).

SUMMARY OF THE INVENTION

The present invention provides apparatus and methods some or all of which may be combined in various embodiments for stimulating animal tissue (for example to trigger a nerve action potential signal in nerves of a human patient) by application of both electrical and optical signals for treatment and diagnosis purposes. In some embodiments, the application of an electrical signal before or simultaneously (or, in some embodiments, after) the application of an optical signal allows the use of a lower amount of optical power or energy than would otherwise be needed if an optical signal alone were used for the same purpose and effectiveness. The application of the electrical signal may precondition the nerve tissue (electrically "priming" the excitable tissue making it more susceptible to stimulation and in particular optical stimulation (sodium and potassium channels are voltage sensitive, such that the probability of a channel opening or being open increases with increased voltage differential from the outside to inside of the cell; upon channel opening, positively charged ions (sodium) move from the extracellular to intracellular space, thus affecting the probability of open for neighboring channels; in some embodiments, the present invention adjusts the voltage increase the probability that a channel is open)) such that a lower-power optical signal can be used to trigger the desired NAP with substantially the same selectivity as seen with the stand-alone optical stimulation that otherwise would take a higher-power optical signal, were the electric signal not applied. In some embodiments, the hybrid combination of electrical and optical stimulation overcomes limitations of each modality, significantly reducing IRNS-threshold levels (order of magnitude) while retaining the highly precise stimulation of discrete axonal populations, thus achieving high spatial selectivity for nerve stimulation with clinically viable safety and efficacy thresholds. This also reduces the optical power requirements for laser devices that mediate the stimulation of neural tissues, thus making implantable laser-based neuroprostheses and neurostimulators more practical for human use or allows more channels using the same power budget (i.e., the power budget being, e.g., the amount of power used in an implantable device).

BRIEF DESCRIPTION OF THE DRAWINGS

FIG. 7A is a perspective schematic view and block diagram of a hybrid-electrical-and-optical system 700 for highly selective nerve stimulation according to some embodiments of the invention.

FIG. 7B is an enlarged perspective schematic view and block diagram of a portion of the hybrid-electrical-and-optical system 700 of FIG. 7A.

FIG. 11($a$) is a graph 1101 of triggered responses as a function of optical energy and electrical stimulation.

FIG. 11($b$) is a graph 1102 of triggered responses as a function of optical energy and delay between the application of electrical stimulation and the optical-stimulation pulse.

FIG. 12($a$) is a plot 1201 of the average of 20 consecutive recordings of CMAPs from electrodes placed in the biceps femoris.

FIG. 12($b$) is a plot 1202 of the average of 20 consecutive recordings of CMAPs from electrodes placed in the gastrocnemius.

FIG. 13($b$) is a photomicrograph of a hybrid-stimulation experimental setup 1302 showing the positioning of glass-pipette electrodes and a 100 μm optical fiber.

FIG. 15($a$) is a plot 1501 of the size of the ROE when a 1.78 $J/cm^2$ optical stimulus was applied.

FIG. 15($b$) is a plot 1502 of the size of the ROE when a 4.71 $J/cm^2$ optical stimulus was applied.

FIG. 15($c$) is a table 1503 summarizing the data associated with the experiments that produced FIG. 15($a$) and FIG. 15($b$).

FIG. 16($b$) is a plot 1602 illustrating the location of the ROE for a second nerve.

FIG. 16($c$) is a plot 1603 illustrating the location of the ROE for a third nerve.

FIG. 16($d$) is a plot 1604 illustrating the location of the ROE for a fourth nerve.

FIG. 17($b$) is a plot 1702 of threshold current (μA) versus time (minutes) with measurements made every two minutes.

FIG. 17($c$) is a plot 1703 of threshold current (μA) versus time (minutes) with measurements made every two minutes.

FIG. 17($d$) is a plot 1704 of threshold current (μA) versus time (minutes) with measurements made every two minutes.

FIG. 18($b$) is a plot 1802 of threshold electrical current (μA) (solid line) and hybrid optical threshold (mJ/pulse) (dotted line) versus time (minutes).

FIG. 19 is a table 1901 summarizing the window of radiant exposures outside of which hybrid stimulation is not possible for some embodiments.

DETAILED DESCRIPTION OF THE INVENTION

Although the following detailed description contains many specifics for the purpose of illustration, a person of ordinary skill in the art will appreciate that many variations and alterations to the following details are within the scope of the invention. Accordingly, the following preferred embodiments of the invention are set forth without any loss of generality to, and without imposing limitations upon the claimed invention. Further, in the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention.

The leading digit(s) of reference numbers appearing in the Figures generally corresponds to the Figure number in which that component is first introduced, such that the same reference number is used throughout to refer to an identical component which appears in multiple Figures. Signals and connections may be referred to by the same reference number or label, and the actual meaning will be clear from its use in the context of the description.

Figure 1A:
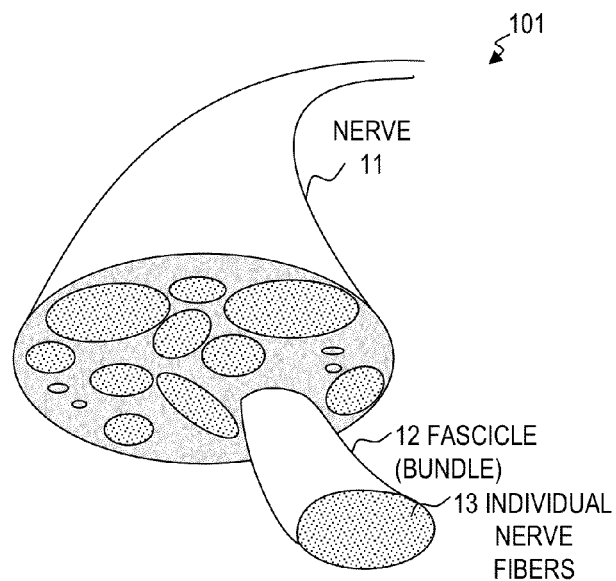
FIG. 1A is a schematic diagram 101 of a nerve 11.
Figure 1B:
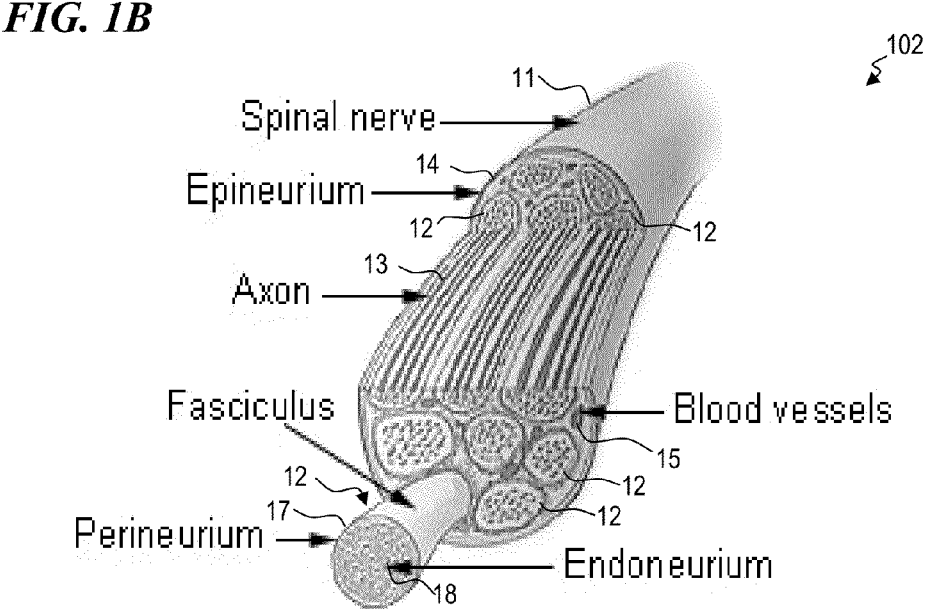
FIG. 1B is a schematic diagram 102 of a nerve 11.
Figure 2A:
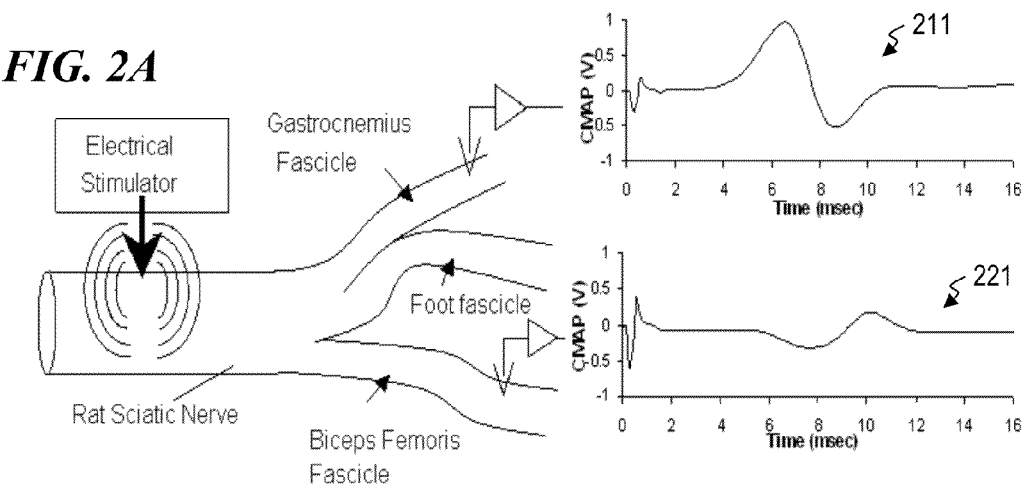
FIG. 2A includes a diagram 201 and graphs 211 and 221 showing different spatial specificities in the sciatic nerve when using electrical nerve stimulation.
Figure 2B:
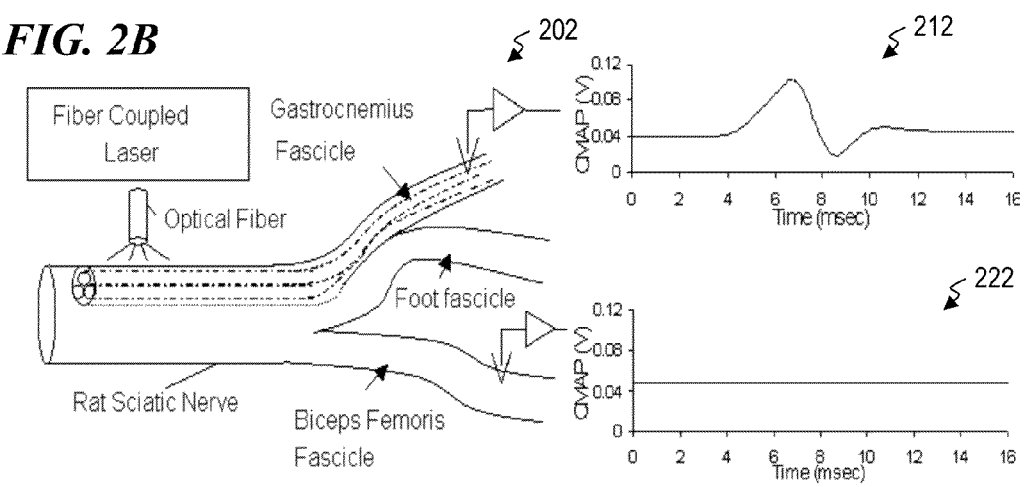
FIG. 2B includes a diagram 202 and graphs 212 and 222 showing different spatial specificities in the sciatic nerve, of electrical nerve stimulation and optical nerve stimulation.
Figure 3:
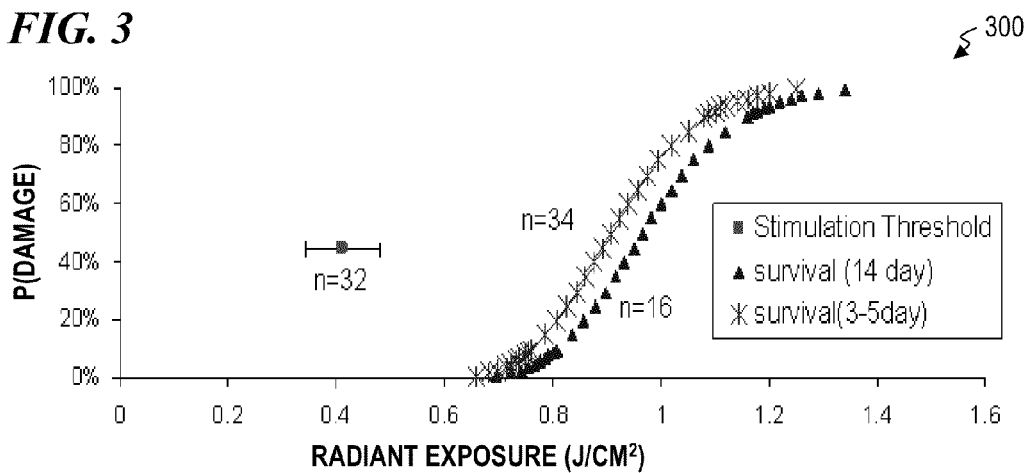
FIG. 3 is a graph 300 of the probability of damage in the rat sciatic nerve as a function of optical radiant exposure ($J/cm^2$).
Figure 4:
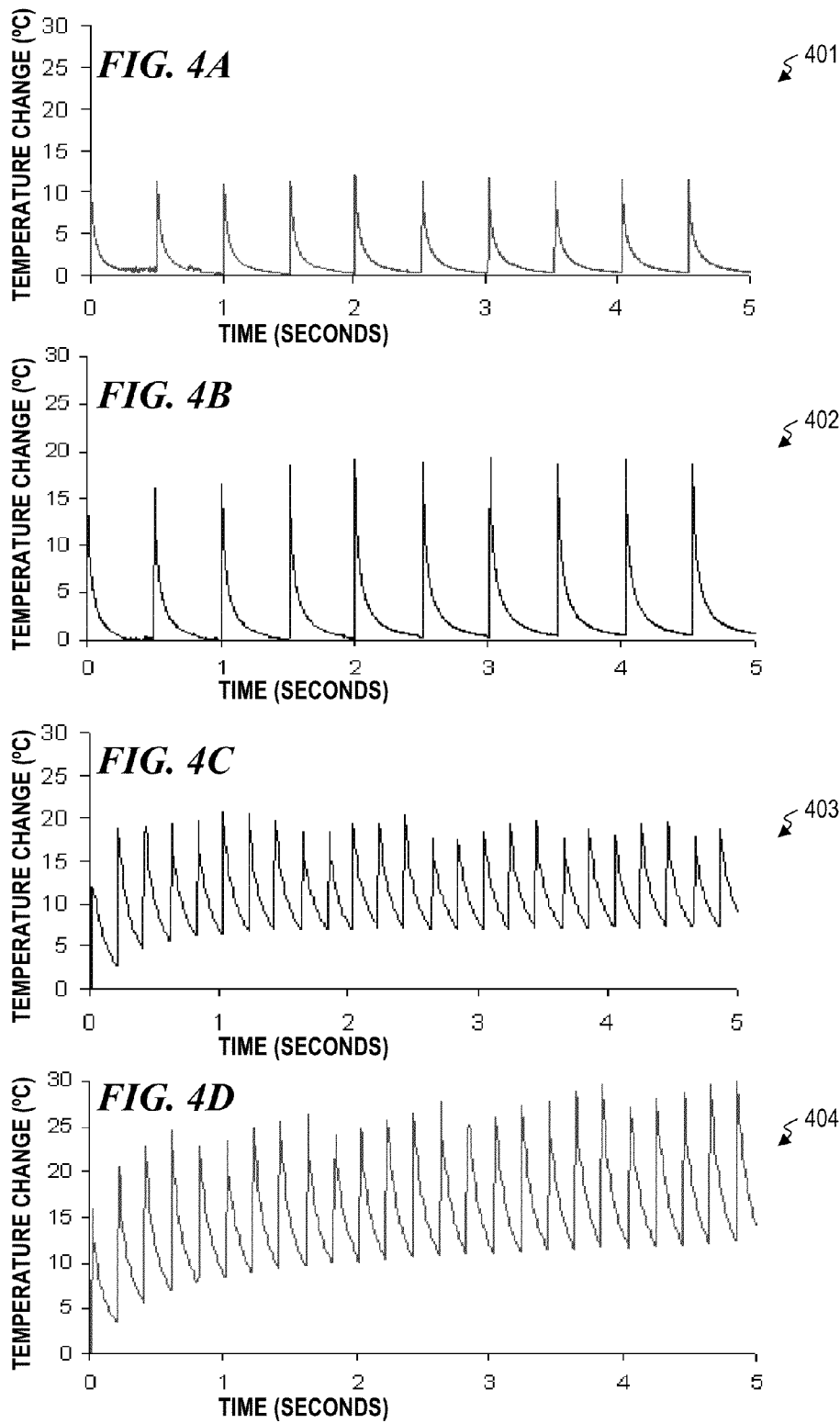
FIG. 4A is a graph 401 of steady-state maximum temperature increase in nerve tissue from pulsed Ho:YAG laser stimulation.
FIG. 4B is a graph 402 of steady-state maximum temperature increase in nerve tissue from pulsed Ho:YAG laser stimulation.
FIG. 4C is a graph 403 of steady-state maximum temperature increase in nerve tissue from pulsed Ho:YAG laser stimulation.
FIG. 4D is a graph 404 of steady-state maximum temperature increase in nerve tissue from pulsed Ho:YAG laser stimulation.
Figure 5:
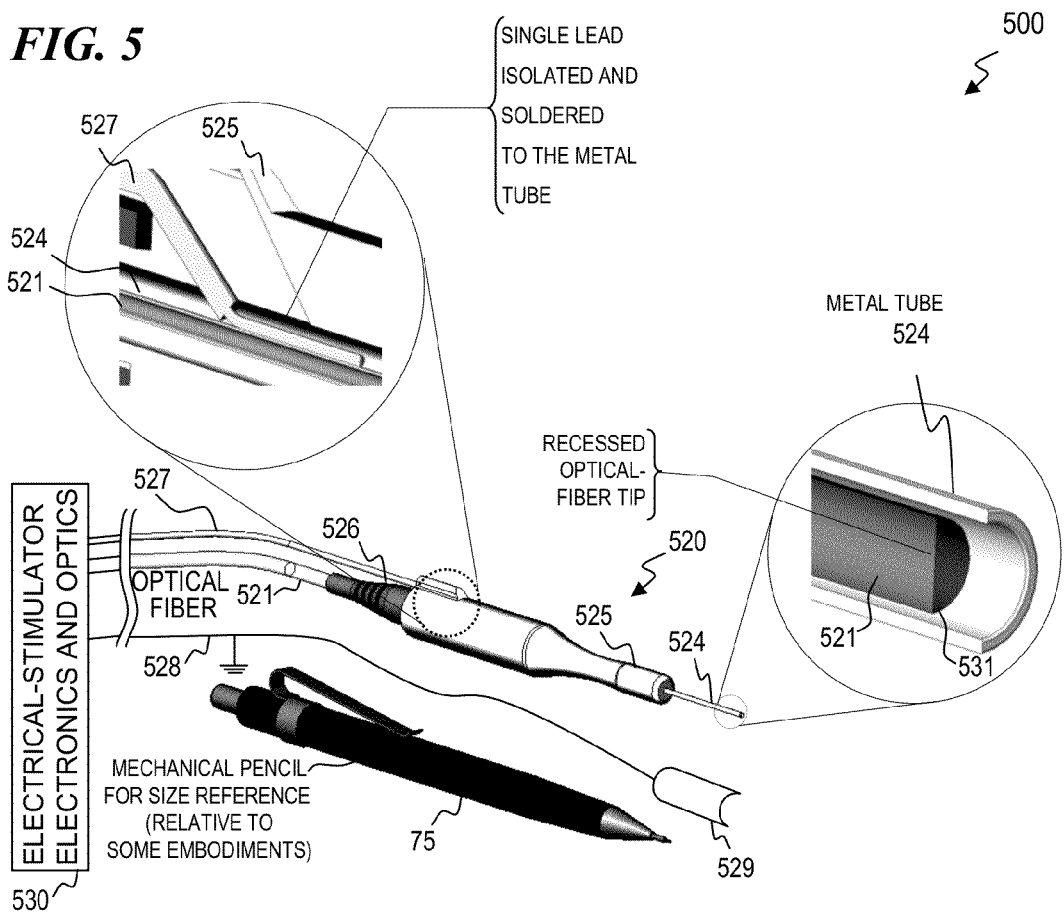
FIG. 5 is a perspective view, partially in cross section, of a system 500 having a hybrid-electrical-and-optical probe 520 developed to test for nerve stimulation thresholds according to some embodiments of the invention.

FIG. 5 is a perspective view of a system 500 having a hybrid-electrical-and-optical probe 520 developed to test for nerve-stimulation thresholds according to some embodiments of the invention. In some embodiments, such as shown in FIG. 5, the electrical-optical (EO) probe 520 uses a metal tube 524 (or other suitable electrical conductor) with an optical fiber 521 and its fiber optic end 531 located within the tube (e.g., in some embodiments, the optical fiber is located in an axial direction in the center of the tube). In some embodiments, the metal tube 524 is made from a biocompatible material such as, for example, titanium or stainless steel or other compatible metals or other electrical conductors. In some embodiments, the fiber optic end 531 of optical fiber 521 is stripped to just the cladding and is bonded in to the center of the tube 524. In some embodiments, the range in fiber-core diameters used for the optical stimulator is from 200 µm to 600 µm (microns), with the fiber cladding, in some embodiments, being about 10% larger than the core. In some embodiments, the inner diameter of the tube is designed to accommodate the 660 µm (the core-plus-cladding diameter of an optical fiber 521 that has a 600-µm-diameter core) which would be the largest of the fiber cladding diameters for such fibers, in some embodiments. In some embodiments, the tip 531 of the fiber optic 521 is recessed within the tube 524 in order to provide a consistent distance between the fiber and the nerve 97 (see FIG. 8) that is to be stimulated. In some embodiments, conductor 524 includes metal that is plated or sputtered onto optical fiber 521 and then the tip 531 of optical fiber 521 is selectively etched away in order to recess the tip within conductor 524. In some embodiments, an external non-electrically conductive insulator 525, such as silicone (or other suitable polymer, ceramic, glass or other electrical insulator), is applied to the outside of the metal electrode 524 (e.g., acting as a handle and/or limiting the location and amount of conductor 524 that is exposed to the tissue of the patient) to allow for the user to place the probe 520 on the nerve 97 or nerve bundle 98 (see FIG. 8) without interfering with the delivery of the electrical stimulation. In some embodiments, an electrical-ground wire 528 and electrically conductive electrode 529 are provided (wherein, in some embodiments, electrode 529 is placed on the patient) in order to provide a ground reference for the electrical signal applied to electrical-conductor tip 524.

As an alternative or in addition to the combined probe 520 that is shown, other embodiments use two or more independent probes, including one probe that is an electrical probe held or placed on the patient's tissue near the nerve-stimulation/activation site, and another probe that is just an optical-fiber probe that is held or placed on or near nerve at the activation site. These separate electrical and optical probes are placed and/or held independently and thus provide to the user additional flexibility in where and how the probes are placed at various distances from each other and from the nerve-stimulation site. In some embodiments, these implementations are used to determine optimal or improved probe configurations and spacing parameters to use for fabricating hybrid probes that are manufactured to implement the optical spacing parameters but could potentially be applied in clinical settings as well. In some embodiments, the hybrid probe is configured such that the spacing or placement of the optical fiber delivery end relative to the electrode is adjustable by the medical professional who is operating the hybrid probe, in order to be able to manipulate, adjust, optimize and set the relative spacing and/or directions that the ends are pointing (e.g., the relative pitch and yaw of the vectors defining the relationship of the respective ends).

In some embodiments, in order to demonstrate lower infrared stimulation thresholds with combined electrical and optical stimulation, an integrated electrical and optical (EO) stimulation system is assembled. A useful feature for the EO system is a combined electrical and optical probe 520. In some embodiments, the design for the electrode includes a mono-polar conductive tube 524. In other embodiments, multi-polar electrode is used, and it includes additional wires or other conductor structures attached to the electrode. In some embodiments, the optical fiber 531 used to deliver infrared stimulation light is connected to and passes through the tube electrode 520 such that its end 521 is slightly recessed within the end of metal tube 524, as shown in FIG. 5. In some embodiments, a silicone coat or handle 525 is applied (and/or molded or otherwise applied) to the exterior of the tube electrode 520 to provide an insulated grip. In order to prevent fiber damage, in some embodiments, a standard fiber-optic strain-relief boot and jacket 526 is used to protect the fiber 531. In some embodiments, the signal-electrode wire 527 is run in a separate cable from the electrical-stimulator electronics 530 to the probe 520. In some embodiments, the ground-electrode wire 528 is run in a separate cable from the remote electrical-stimulator electronics and optical source controller 530 (e.g., the power and control that generates the electrical and laser signal(s)) to the probe 520, while in other embodiments, the optical fiber 521, signal-electrode wire 527, and ground-electrode wire 528 are housed in a single cable that extends from controller 530 to probe 520. In some embodiments, in order to provide a consistent optical energy delivered to the tissue, the fiber is recessed within the tube approximately 1 mm away from the nerve 97 (see FIG. 8). In other embodiments, the distance by which the fiber is recessed is more than 2 mm, or by about 2 mm, 1.6 mm, 1.4 mm, 1.2 mm, 0.8 mm, 0.6 mm, 0.4 mm, 0.2 mm, 100 microns, or 0 mm (i.e., when the recess is said to be 0 mm, the end of the fiber is flush with the end of the tube or cannula). In other embodiments, the fiber tip extends from and beyond the end of the cannula or tube, for example, in some embodiments, by a non-zero amount of no more than 100 microns (0.1 mm), 0.2 mm, 0.4 mm, 0.6 mm, 0.8 mm, 1 mm, 1.2 mm, 1.4 mm, 1.6 mm, or 2 mm or more. In some embodiments that use a metallized coating on the optical fiber for the electrical conductor, the optical fiber extends as a bare optical fiber beyond the end of the metallization by a non-zero amount of no more than 100 microns (0.1 mm), 0.2 mm, 0.4 mm, 0.6 mm, 0.8 mm, 1 mm, 1.2 mm, 1.4 mm, 1.6 mm, or 2 mm or more. If the fiber core diameter is 400 microns, the fluence delivered to the nerve is 2.5 J/cm$^2$ with 4 W of peak power over 1 msec (one millisecond), assuming a flat-top profile. (In some embodiments, this peak power is calculated with a Gaussian profile, while in other embodiments, a flat profile is used for the calculation; in some such embodiments, the same calculation method is used that was used for other calculations, such as previously published papers by Vanderbilt University researchers that measure the optical fluence needed for triggering a NAP in the sciatic rat nerve, in order to compare the fluence calculation in the present invention with those papers.) The typical stimulation threshold for the sciatic rat nerve was determined to be about 1 to 2 J/cm$^2$.

Figure 6A:
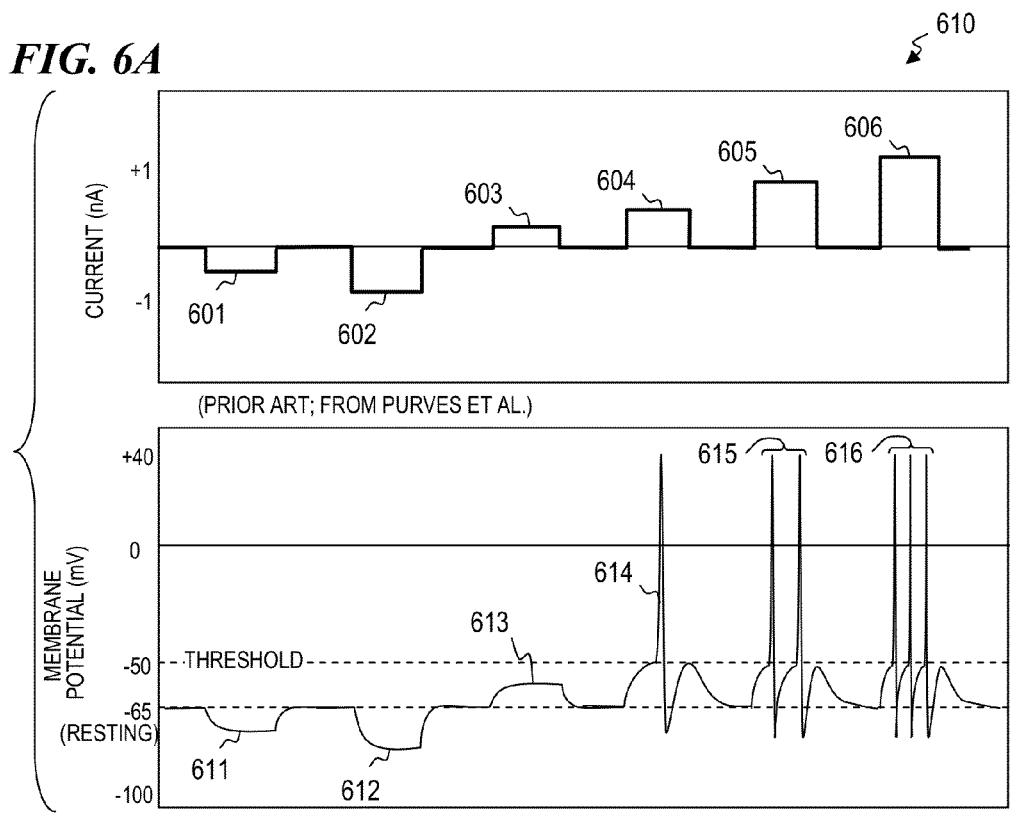
FIG. 6A is a schematic prior-art graph 610 of an electrical-only pulse set for nerve stimulation according to some embodiments of the prior art.

FIG. 6A is a schematic prior-art graph 610 (adapted from Dale Purves et al., Neuroscience, 3$^{rd}$ ed. page 31) of an electrical-only pulse set for nerve stimulation according to some embodiments of the prior art. Regarding electrical-only stimulation, in some embodiments, a resting nerve has a voltage of about −65 milliVolts (mV) (see Dale Purves et al., Neuroscience, 3$^{rd}$ ed. page 31) to about −75 mV (called the resting potential or polarized voltage), and a CNAP or NAP has an electrical-voltage-change trigger threshold of about +15 mV to about +40 mV above the resting-nerve potential (i.e., of the voltage at the nerve must be "depolarized" by changing its voltage to between about −55 mV and about −30 mV). Failed initiations (e.g., 611, 612, and 613) caused by a lower-than-threshold voltage change or current injected into the cell (e.g., 601 and 602 which hyperpolarize the cell, and 613 which depolarizes the cell but not enough to trigger a NAP) will allow the nerve to return to its resting potential of about −65 to −80 mV in less than about 1 millisecond (ms). A depolarizing electrical signal 603 that is below threshold will cause a depolarized response 613 that does not trigger a NAP. A depolarizing electrical signal 604 that is at or slightly above threshold will cause a depolarized response 614 that does trigger a NAP, because if a sufficient electrical voltage or current is applied (e.g., signal 604), the nerve-stimulation signal will trigger a nerve action potential 614, and once triggered, the NAP typically enters a rising phase that takes the voltage to between about +40 mV and about +50 mV in about 1 msec, and the voltage then drops to between about −40 mV and about −90 mV in about 1 msec. If the stimulation voltage pulse is much higher than the threshold voltage change or current injection (e.g., stimulation signal pulses 605 or 606), the NAP will be triggered more quickly (perhaps 1 msec) or a plurality of NAPs will be triggered (e.g., 615 or 616 if the triggering pulse remains active for a sufficient length of time) than if a slowly-rising minimum threshold voltage change is applied (which could take up to about 10 msec or more to trigger the NAP).

Figure 6B:
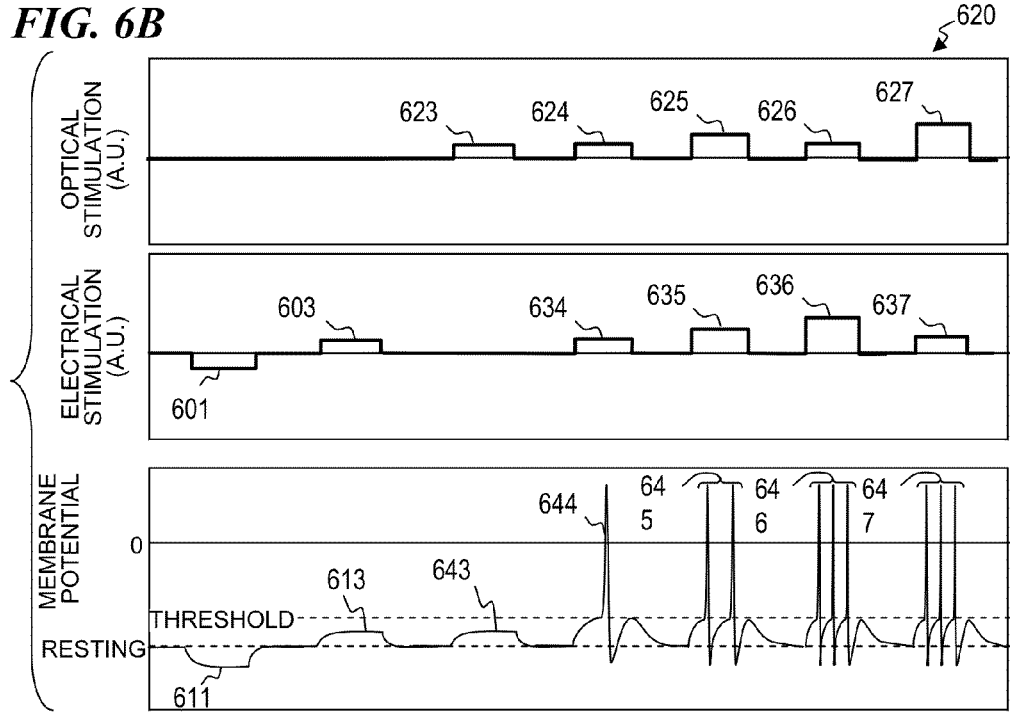
FIG. 6B is a schematic graph 620 of a hybrid-electrical-and-optical pulse set for nerve stimulation according to some embodiments of the invention.

FIG. 6B is a schematic graph 620 of a hybrid-electrical-and-optical pulse set for nerve stimulation according to some embodiments of the invention. As described above for FIG. 6A, a hyperpolarizing electrical signal 601 will cause a hyperpolarized response 611 that does not trigger a NAP. A depolarizing electrical signal 603 that is below threshold will cause a slightly depolarized response 613 that does not trigger a NAP. An optical signal 623 that is below threshold will also cause a depolarized response 643 (similar to the response 613 to a sub-threshold electrical signal 603) that also does not trigger a NAP. However, depolarizing electrical signal 634 that if delivered alone would be below threshold delivered substantially simultaneously along with an optical signal 624 that if delivered alone would be below threshold will, when both are delivered together in time, cause a depolarized response that does trigger a NAP 644. A larger and/or longer depolarizing electrical signal 635 (e.g., one that if delivered alone would be at threshold) along with a larger and/or longer optical signal 625 (e.g., one that if delivered alone would be at threshold) will cause two or more depolarized responses that each trigger a NAP 645 (e.g., the two NAPs 645 shown here). In some embodiments, a larger and/or longer depolarizing electrical signal 636 (e.g., one that if delivered alone would be above threshold) along with a below-threshold optical signal 626 (e.g., one that if delivered alone would be below threshold) will cause two or more depolarized responses that each trigger a NAP 646 (e.g., the three NAPs 646 shown here). In some embodiments, a below-threshold depolarizing electrical signal 637 (e.g., one that if delivered alone would be below threshold) along with an above-threshold optical signal 627 (e.g., one that if delivered alone would be above threshold) will cause two or more depolarized responses that each trigger a NAP 647 (e.g., the three NAPs 647 shown here).

In some embodiments of the present invention that uses both electrical and optical signals for stimulation, the electrical signal is pulsed. In some embodiments, the pulsed electrical signal is applied simultaneously with an optical pulse of substantially the same duration. In other embodiments, the electrical pulse can be longer or shorter than the optical pulse.

In some embodiments, the electrical pulse is applied at a point in time starting before the optical pulse. In some such embodiments, the electrical pulse continues for the duration of the optical pulse. In other embodiments, the electrical pulse ends before or as the optical pulse starts. In other embodiments, the electrical pulse ends as or after the optical pulse ends. In some embodiments, the main electrical pulse is of such long duration and is applied sufficiently early relative to the optical pulse as to essentially act as a DC electrical-preconditioning voltage. In some embodiments, a DC electrical bias is applied before the main electrical pulse is applied.

In other embodiments, the optical pulse is applied starting before the electrical pulse. In some such embodiments, the optical pulse continues for the duration of the electrical pulse. In other embodiments, the optical pulse ends before or as the electrical pulse starts. In other embodiments, the optical pulse ends as or after the electrical pulse ends. In some embodiments, the main optical pulse is of such long duration and is applied sufficiently early relative to the electrical pulse as to essentially act as a DC optical preconditioning voltage. In some embodiments, a DC optical bias is applied before the main optical pulse is applied.

In some embodiments of the present invention, the stimulus electrical pulse and/or electrical DC bias are limited to a value that is generally lower than required (i.e., lower than the minimum threshold voltage change) for electrical-only triggering of a nerve action potential. The nerve would then return to its resting potential after such a failed electrical stimulation. That is, the electrical signal applied would not trigger a NAP if the optical signal is not also applied. In other embodiments, the electrical signal applied by the present invention would be sufficient to usually trigger the NAP, but would or occasionally could take too long or occasionally would and occasionally would not trigger a NAP if used alone, but when applied with the optical signal of the present invention provides a more precise timing and/or reliable triggering of the NAP signal. In other embodiments, the electrical signal is applied to speed up the recovery time for the later triggering of another NAP (a nerve typically requires a certain amount of time to reset or recover after one NAP occurs, and the electrical signal is applied in such a manner as not to trigger the next NAP but to shorten the time needed between NAPs by assisting ion transport across the nerve cell membrane).

In some embodiments, the optical signal includes a "DC" optical component (i.e., a long pulse or essentially constant background amount of light applied before the main optical pulse(s)). In some embodiments, the "DC" optical component also reduces the power that would otherwise be required to trigger the desired NAP.

In some embodiments, the optical pulse and/or "DC" optical component are limited to a power and/or energy value that is generally lower than that required for optical-only triggering of a nerve action potential. That is, the optical signal would not trigger a NAP if the electrical signal is not applied. However, when applied simultaneously or at least close enough in time the combination of the relatively small electrical and optical stimulation signals (that is, each being smaller than is normally required to trigger the NAP) is sufficient to trigger a NAP.

In conventional electrical stimulation even the smallest electrical probe will apply the electrical signal to a relatively large number of nerves and thus using only electrical stimulation it is difficult to trigger a NAP in only one particular nerve or just a few nerves. On the other hand, the location of the delivery of optical stimulation can be quite precise by using optical fibers and focussing optics, but requires relatively large amounts of optical power. One benefit of the present invention, using substantially simultaneous relatively small electrical and optical stimulation signals, is that the risk of optical damage to the cell is reduced, since lower optical power is required, while the precision delivery of the stimulation by the optical signal still allows a NAP in a particular nerve to be triggered while avoiding also triggering NAPs in surrounding nerves.

In some embodiments, the electrical stimulation can be applied external to the skin of the patient, such as is done with transcutaneous electrical nerve stimulation (TENS) devices. In some embodiments, such a device is used, but the electrical signal is reduced to a level that does not trigger a NAP. An optical signal is simultaneously (or, as discussed above, substantially simultaneously) applied to the desired tissue to be stimulated. In some such embodiments, the optical signal is delivered using an implanted optical fiber. In other embodiments, the optical signal is applied from outside the body and through the skin of the patient.

FIG. 7A is a perspective schematic view and block diagram of a hybrid-electrical-and-optical system 700 for highly selective nerve stimulation according to some embodiments of the invention. FIG. 7B is an enlarged perspective schematic view and block diagram of a portion of the hybrid-electrical-and-optical system 700 of FIG. 7A. In some embodiments, hybrid-electrical-and-optical system 700 includes a nerve-interface unit 720 that is clamped onto or around a nerve 11. In some embodiments, nerve-interface unit 720 includes a plurality of fine-pitched electrodes (such as have been used in FINE-type electrodes described above). In some embodiments, nerve-interface unit 720 is configured to snap together with an opening having a height that is smaller than its width to slightly compress the nerve 11. In some embodiments, the electrode portion of nerve-interface unit 720 is constructed in a manner similar to U.S. Pat. No. 6,456,866 to Tyler et al. (described above), but has many more electrodes and also includes a plurality of lasers (such as VCSELs) in the nerve-interface unit 720, or is connected by a plurality of optical fibers to a plurality of externally located lasers.

In some embodiments, nerve-interface unit 720 includes a first plurality of fine-pitched electrodes 723 on one side (e.g., the upper-front side) and a second plurality of fine-pitched electrodes 724 on an opposite side across the nerve 11, configured to generate one or more narrow stripes of electric field 788 transverse to the nerve 11 (e.g., by applying a voltage between one of the upper front electrodes 723 and one of the lower front electrodes 724, as shown in FIG. 7B).

In some embodiments, nerve-interface unit 720 includes a first plurality of fine-pitched electrodes 723 on one side (e.g., the upper-front side) (and/or a second plurality of fine-pitched electrodes 724 on one side (e.g., the lower-front side)) and a third plurality of fine-pitched electrodes 725 on an opposite side (e.g., the upper-back side) (and/or a second plurality of fine-pitched electrodes 726 on an opposite side (e.g., the lower-back side)) further up the nerve 11, configured to generate one or more narrow stripes of electric field 787 longitudinally along the nerve 11 (e.g., by applying a voltage between one of the upper front electrodes 723 and one of the upper back electrodes 725, as shown in FIG. 7A). In some embodiments, by providing a plurality of such finely pitched electrodes on opposite sides of nerve 11 as well as spaced longitudinally along the nerve 11, the direction across and along the nerve can be precisely controlled. In some embodiments, electrical-pulse control device 712 (under the control of system controller 711) drives electrical signals along conductors 722 to drive the electrodes 723, 724, 725, and/or 726 for a portion of the nerve stimulation (the electrical modality of the two-modality protocol).

In addition, in some embodiments, nerve-interface unit 720 includes a first plurality of fine-pitched optical emitters 732 on one side (e.g., the lower middle) of unit 720 as shown in FIG. 7B. In some embodiments, optical emitters 732 include ends of a plurality of optical fibers (used to carry signals 731, which in this case are optical signals traveling to the probe, wherein the optical signals have been generated in controller 713) that are coupled to laser emitters (e.g., in some embodiments, VCSELs that are each coupled to one or more of the plurality of optical fibers) in optical controller 713 at one end and that emit light within unit 720 directed toward a particular nerve axon (sub-fascicular stimulation) or fascicle (whole-fascicle stimulation). In some such embodiments, only one optical fiber is driven in order to evoke a NAP in a particular fiber at a time, while in other embodiments, a plurality of fibers can be driven to evoke a broader response (e.g., triggering NAPs in separate axons).

In other embodiments, signals 731 are electrical signals from optical controller 713 that drive one or more of the plurality of light emitters (e.g., in some embodiments, vertical-cavity surface-emitting lasers (VCSELs) 732) that are mounted to unit 720, such as shown in FIG. 7B. Note that signals 731, in some embodiments, are optical signals carried by optical fibers from lasers in controller 713 to fiber-end emitters in probe 720 (as shown in FIG. 7A), while in other embodiments, signals 831 are electrical signals from optical controller 713 that carry electricity drive one or more of the plurality of light emitters (e.g., in some embodiments, (VCSELs), as shown in FIG. 7B). In some such embodiments, only one VCSEL 732 is driven in order emit a light pulse 789 (e.g., a light pulse that would be sub-threshold but for the applied electric field 788 as shown in FIG. 7B, or in the case of FIG. 7A, the longitudinal electric field 787) to evoke a NAP in a particular nerve fiber at a given time, while in other embodiments, a plurality of VCSELs can be driven simultaneously or in close temporal proximity to evoke a broader response. In the situation where it is desired to evoke simultaneous NAPs in a plurality of different fibers, one or more of the plurality of possible pairs or subsets of electrodes (e.g., a selected one of the electrodes 723) might be connected to an electrical ground and simultaneously a non-zero sub-threshold signal voltage is applied to one of the electrodes 724 (which generates a transverse voltage across a subset of the nerve 11), or one of the electrodes 725 (which generates a longitudinal voltage along a length of a subset of the nerve 11), or one of the electrodes 726 (which generates a transverse and longitudinal voltage across and along a length of a subset of the nerve 11), or one of the other electrodes 723 (which generates a side-to-side (somewhat transverse) voltage across the top of a subset of the nerve 11), is/are driven with a sub-threshold voltage pulse to precharge the various nerves to be stimulated and two or more optical emitters are driven to generate spatially separated optical pulses to trigger the desired subset of nerves to obtain the desired simultaneous NAPs. In the situation where it is desired to evoke a sequence of NAPs in a plurality of different nerve fibers, one or more of the plurality of possible pairs or subsets of electrodes is/are driven with one or a sequence of sub-threshold voltage pulses to precharge the various nerves to be stimulated in the sequence desired and two or more optical emitters are driven in a sequence to generate temporally and/or spatially separated optical pulses to trigger the desired subset of nerves to obtain the desired sequence of NAPs.

By selectively applying a sub-threshold voltage pulse from one of the electrodes (723, 724, 725, or 726) to another of the electrodes (723, 724, 725, or 726) to generate an electrical field, and then selectively applying a narrow-spot optical pulse, the present invention provides precise control to trigger a sub-fascicular NAP.

In some embodiments, the electrical signal is applied between a first electrode and a second electrode that are located directly across from one another in probe 720 (e.g., such as shown in FIG. 7A, from the electrode 723 that is located fifth-most from the left-hand side of the front top row, to the electrode 724 that is located fifth-most from the left-hand side of the front bottom row) to generate electric field 788 of FIG. 7A. In some embodiments, the electrical signal is applied between a first electrode and a third electrode that are located axially across from one another in probe 720 (e.g., from the electrode 723 that is located third-most from the left-hand side of the top row, to the electrode 725 that is located third-most from the left-hand side of the back top row) to generate electric field 787 of FIG. 7A. Note that in some embodiments, only one of the two electrical fields shown in FIG. 7A would be applied at any one time.

In other embodiments, the electrical signal is applied between a first electrode and a second electrode that are located not only across but diagonally across from one another in probe 720 (e.g., from the electrode 723 that is located second-most from the left-hand side of the front top row, to the electrode 724 that is located fifth-most from the left-hand side of the front bottom row, or from the electrode 725 that is located second-most from the left-hand side of the back top row, to the electrode 726 that is located fifth-most from the left-hand side of the back bottom row). In some embodiments, the electrical signal is applied between a first electrode and a third electrode that are located not only axially but diagonally transverse as well as axially across from one another in probe 720 (e.g., from the electrode 723 that is located second-most from the left-hand side of the top row, to the electrode 725 that is located seventh-most from the left-hand side of the back top row or to the electrode 726 that is located ninth-most from the left-hand side of the back bottom row). Note that in some embodiments, the electric field can be applied from any one electrode to any other electrode in probe 720, in order to enhance selectivity and apply the electric field to the smallest amount of tissue possible with a given probe. In yet other embodiments, the electrode is applied from a plurality of electrode to a plurality of other electrodes (e.g., from the electrodes 723 that are located second-most, third-most and fourth-most from the left-hand side of the front top row, to the electrodes 724 that are located third-most, fourth-most and fifth-most from the left-hand side of the front bottom row) in order to provide a more uniform electric field across the spot of tissue to be optically stimulated with a laser pulse of a given spot size and penetration depth.

In some embodiments, the optical emitters are located in both the top and bottom of probe 720, and their respective optical energy or power are limited in order to provide greater selectivity (i.e., the top-side optical emitters would be driven with an optical signal having a limited penetration depth in order to trigger responses only in the top portion of the nerve 11, and the bottom-side optical emitters would be driven with an optical signal having a limited penetration depth in order to trigger responses only in the bottom portion of the nerve 11). In some embodiments, both the optical signal and the electrical signal are limited in power and area in order to further enhance the selectivity of the portion of the nerve 11 that is triggered to have a NAP.

In essence, the probe 720 of FIG. 7A includes two-dimensional array (e.g., two rows of a Cartesian grid) of electrodes is provided on both opposing inner surfaces of probe 720 (e.g., the two rows on the top inner surface: electrodes 723 and electrodes 725 shown in FIG. 7A and two rows on bottom inner surface: electrodes 724 and electrodes 726 shown in FIG. 7A). In some such embodiments, the electrical signal is applied between one or more selected top electrodes and one or more selected bottom electrodes (in some embodiments, these can be directly across from one another, while in other embodiments, there is a transverse and/or longitudinal (axial) diagonal component between the selected electrodes to which the electrical field is applied. In other embodiments, one or more additional rows are provided on the top inner surface and the bottom inner surface so that a grid of electrodes is provided on the entire top inner surface between the edge where electrodes 723 and the edge where electrodes 725 are shown in FIG. 7A and across the entire bottom inner surface between the edge where electrodes 724 and the edge where electrodes 726 are shown in FIG. 7A.

In other embodiments, probe 720 of FIG. 7A includes two-dimensional array (e.g., two or more rows of a Cartesian grid) of electrodes is provided on one surface of probe 720 (e.g., the electrodes 723 and the electrodes 725 shown in FIG. 7A), while a single planar electrode is placed on the opposite inner surface (e.g., across the entire bottom inner surface between the edge where electrodes 724 and the edge where electrodes 726 are shown in FIG. 7A), and the electrical signal is applied from one or more of the top electrodes and the single bottom electrode.

In some embodiments, the combination of electrodes needed to provide the electrical field needed for triggering a NAP in a particular nerve is empirically determined by trying different combinations of electrodes as pairs until the desired nerve response is evoked, and similarly the optical emitter that best evokes the desired nerve response is empirically determined by trying different combinations of optical emitters and electrodes. In some embodiments, one or more pairs of the electrodes (723, 724, 725, or 726) are also or alternatively used to measure the resulting NAP generated by the electrical and optical stimulation. In some embodiments, once the desired nerve response and/or sensed NAP is detected as a result of the stimulation, the empirically determined combination of electrodes and optical emitters that evoke that desired response is stored in system controller 711.

Figure 7C:
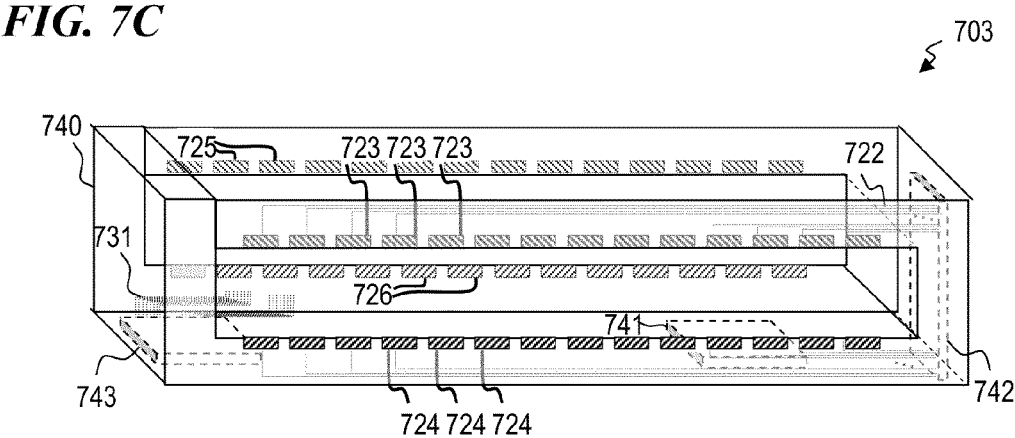
FIG. 7C is a perspective schematic view and block diagram of a hybrid-electrical-and-optical system 703 having one or more embedded electronic and/or optical chips according to some embodiments of the invention.

In some embodiments, one or more of the circuits for controller 711, electrical stimulator 712 and/or optical stimulator 713 are implemented in electronic chips that are mounted within nerve-interface unit 720 as shown in FIG. 7C.

FIG. 7C is a perspective schematic view and block diagram of a hybrid-electrical-and-optical system 703 having one or more embedded electronic and/or optical chips according to some embodiments of the invention. In some embodiments, system 703 is much the same as system 700 described above, except that nerve-interface unit 740 includes a plurality of integrated-circuit (IC) chips (corresponding to nerve-interface unit 720 described above), some or all of the circuitry of controller 711 is implemented in one or more IC chips 741, and/or some or all of the circuitry of electric-pulse generator 712 is implemented in one or more IC chips 742, and/or some or all of the circuitry of optical-pulse controller and/or generator 713 is implemented in one or more IC chips 743. In some embodiments, two or more of chips 741, 742, and 743 are merged into a single integrated-circuit chip. In some embodiments, a battery (not shown) is also embedded in nerve-interface unit 740. In other embodiments, the battery and/or some of the circuitry is implemented in a separate implanted controller unit. In some embodiments, the system controller 711 (in chip 741) is wirelessly reprogrammable (e.g., by radio waves, laser light, or other suitable communications channels), in order to customize its functionality.

In a given fascicle, there are typically fifteen (15) times as many sensory-nerve pathways (sending signals to the brain) as motor-nerve pathways (sending signals from the brain to the muscles). In some embodiments, the present invention provides a prosthesis having a plurality of sensors that generate signals based on measured environmental factors, and these signals are converted to electrical signals 722 and optical signals 731 to trigger NAPS in the appropriate sensory-nerve pathways to convey this information to the patient. In some embodiments, the array of electrodes (723, 724, 725, and 726) are used to detect particular motor-nerve signals that are then converted to signals to control actuators and motors in the prosthesis, such as shown in FIG. 10B and described below. In some embodiments, one or more chips are provided in nerve-interface unit 740 that each provide a plurality of VCSELs 732, each of which can be individually controlled to emit the required optical pulses 789 (as shown in FIG. 7B).

In some embodiments, the plurality of electrodes includes a first subset (electrodes 723 and electrodes 724) that are located along a first perimeter (e.g., the front-side perimeter) of a nerve-interface unit 720 that surrounds the nerve 11 of a human patient 99. In some embodiments, the plurality of electrodes further includes a second subset (electrodes 725 and electrodes 726) that are located along a second perimeter (e.g., the back-side perimeter) of the nerve-interface unit that is longitudinally spaced (e.g., by the longitudinal thickness of nerve-interface unit 720) from the first perimeter. In some embodiments, the center-to-center spacings of the electrodes are in a range of between 50 microns and about 1000 microns (0.05 to 1.0 millimeters).

In some embodiments, the plurality of optical emitters includes a first subset (optical emitters 732) that are located along a first perimeter (e.g., the bottom half of an inside perimeter) of nerve-interface unit 720 that surrounds the nerve 11 of a human patient 99. In some embodiments, the plurality of optical emitters further includes a second subset (not shown here) that are located along a second perimeter (e.g., along the top half of the inside perimeter opposite the bottom inside perimeter) of the nerve-interface unit.

Evidence seems to show that the superposition of the two modalities (i.e., the electrical stimulation and the optical stimulation) is not a simple linear superposition. In some embodiments, optimization of pulse durations, synchronized timing of the two pulse modalities, spatial distribution of the electrical field relative to the laser-induced thermal field, as well as other variables, are addressed empirically. In some embodiments, this optimization significantly reduces the IRNS threshold requirements with a substantially smaller percentage of the electrical stimulus threshold. In some such embodiments, this optimization accelerates the clinical implementation of neuroprostheses with highly precise neural interfaces.

Figure 8:
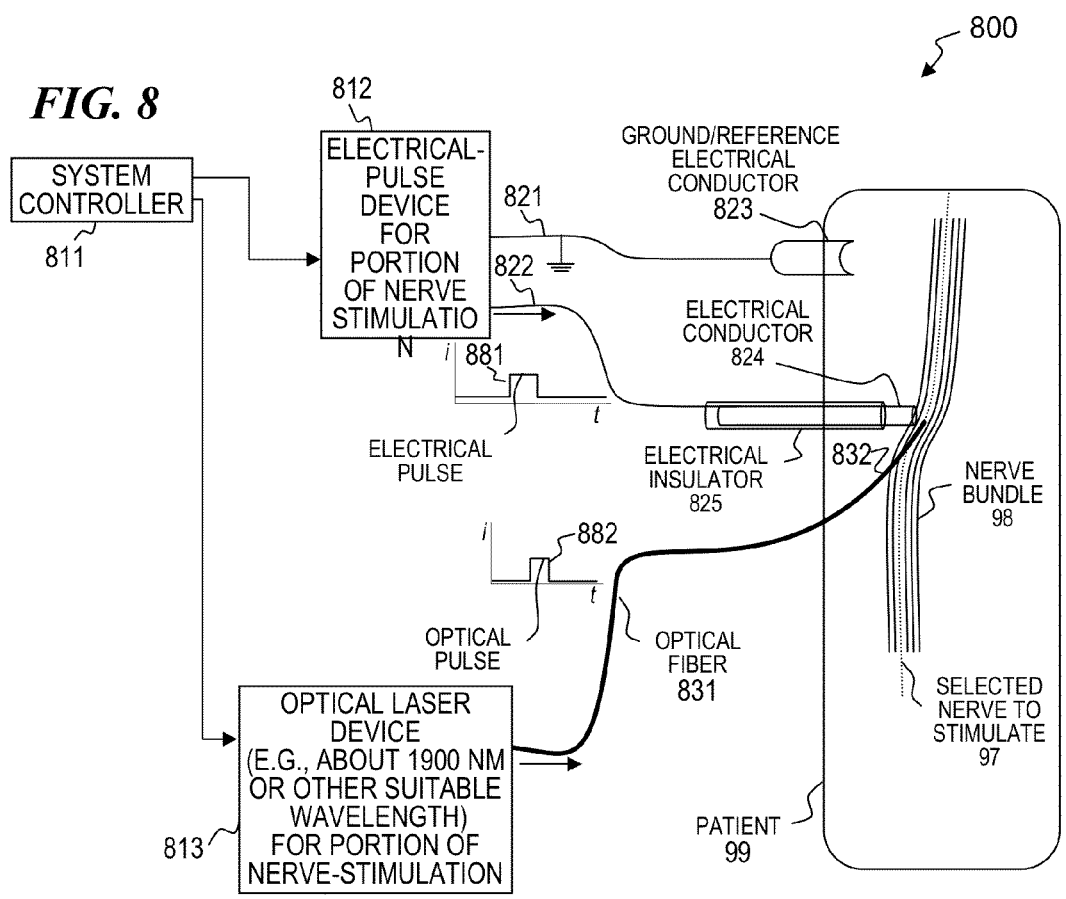
FIG. 8 is a perspective schematic view and block diagram of a hybrid-electrical-and-optical system 800 for nerve stimulation according to some embodiments of the invention.

FIG. 8 is a perspective view and block diagram of a hybrid-electrical-and-optical system 800 for nerve stimulation according to some embodiments of the invention. In some embodiments, the electrical signal is applied using one delivery probe 824 while the optical signal is applied using a separate or substantially separate delivery probe 832 (i.e., using two or more separate probes or probe ends). In some embodiments, a system controller 811 controls the timing and other characteristics of the electrical signal and the optical signal (such as portrayed in insert graphs showing hypothetical plots of intensity (i) as a function of time (t) for an electrical-pulse signal 881 and for an optical-pulse signal 882). In some embodiments, such as shown in FIG. 8, one or both of the electrical delivery probe 824 and the optical delivery probe 832 are invasive (e.g., fully implanted) and/or deliver the electrical signal and the optical signal internal to the body of the patient 99—in some embodiments, delivering the signals to a particular selected set of nerve pathways 97 that is the set of nerve pathways to be stimulated within nerve bundle 98. In some embodiments, the selected set of nerve pathways 97 is a small subset (e.g., in some embodiments, less than 5%; less than 10%, less than 15%, less than 20%, or less than 25%, less than 30%, less than 40%, or less than 50%) of the nerve pathways within a given fascicle or nerve bundle 98, while in other embodiments, selected set of nerve pathways 97 includes substantially all of the nerve pathways within the given fascicle 98. In some other embodiments, one or both of the electrical-signal generator 812 and the optical signal generator 813 are located external to the body of the patient. In some other embodiments, one or both of the electrical signal generator and its associated electrical probe(s) and the optical signal generator and its associated optical probe(s) are implanted and/or located internal to the body of the patient. In some embodiments, electrical-signal generator 812 is connected by wire 821 to ground/return probe 823 and electrical-signal generator 812 is connected by wire 822 to electrical-signal probe 824. In some embodiments, the electrical probe 824 is at least partially covered with a dielectric/electrical-insulator material 825. In some embodiments, an optical cable 831 includes one or more optical fibers to deliver light to optical probe 832.

Figure 9:
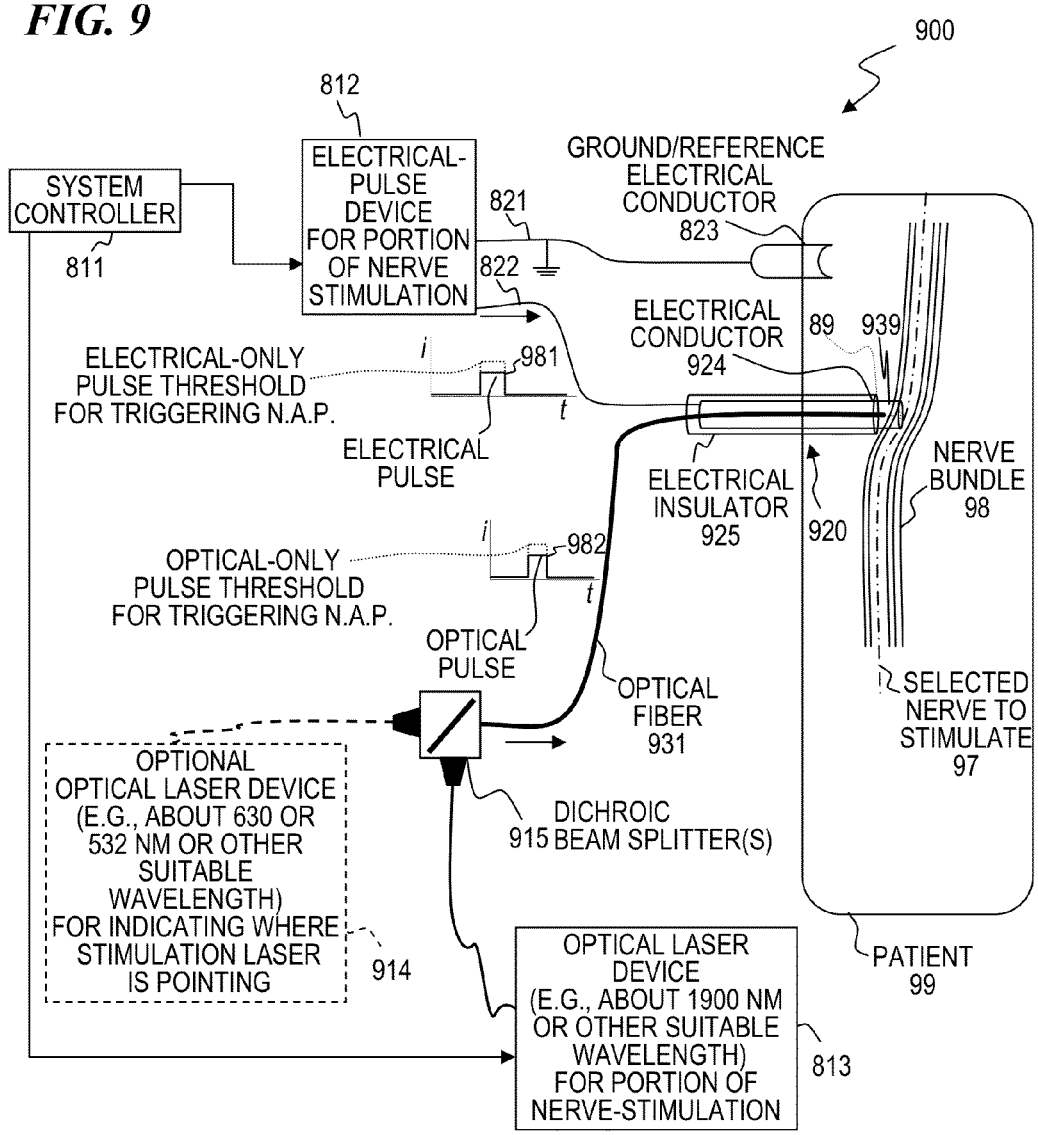
FIG. 9 is a perspective view and block diagram of a hybrid-electrical-and-optical system 900 for nerve stimulation according to some embodiments of the invention.

FIG. 9 is a perspective view and block diagram of a hybrid-electrical-and-optical system 900 for nerve stimulation according to some embodiments of the invention. In some embodiments, the optical signal and the electrical signal are both delivered through the same probe 420, such as one of those described in U.S. patent application Ser. No. 12/018, 185 filed Jan. 22, 2008, titled "HYBRID OPTICAL-ELECTRICAL PROBES," by the inventors of the present invention (which issues as U.S. Pat. No. 7,883,536 on Feb 8, 2011). For example, some embodiments use an optical fiber 931 embedded in a hollow electrically conductive pipe or cannula 924 such as one made of stainless steel or other bio-compatible metal or other electrical conductor. In some embodiments, the optical fiber 931 or its signal-carrying core terminates short of the end of the hollow electrical conductor 924. In some embodiments, most or all of the length of the outside of the electrical conductor is coated with a bio-compatible insulator 925 (such as a conformal polymer coating) that leaves an exposed electrically conductive tip 924 used to apply the electrical signal to the patient 99's tissue next to or in the particular selected nerve 97 to be stimulated (i.e., either the outside or the inside of the hollow conductive tip 924 provide a conductive surface that applies a voltage to the surrounding tissue).

In other embodiments, the electrical-signal conductor 924 is formed by plating, sputtering, evaporating, and/or otherwise depositing a metal or other conductor onto an optical fiber 931. In some such embodiments, most or all of the length of the outside of the conductor is coated with a bio-compatible insulator (such as a conformal polymer coating) that leaves an exposed conductive tip used to apply the electrical signal to the patient 99's tissue next to or in the nerve to be stimulated 97. In some embodiments, a visible light laser device 914 (e.g., one that emits red light at 630-nm wavelength or green light at 532-nm wavelength or other suitable visible light (400-to-700-nm) wavelength) is used to provide a visible indicator light that is combined (e.g., using a dichroic mirror or other combiner 915) with the infrared (IR) stimulation light from emitter 813, in order that the visible light provides visual feedback to the operator showing where the IR signal 89 will be delivered. This is particularly useful in embodiments where a focussing optic 939 at the end of the optical fiber causes the nerve-stimulation signal light 89 (in some embodiments, along with a co-propagating visible indicator light) to be projected a short distance from the end of probe 920. In some embodiments, a plurality of different IR wavelengths are used (e.g., combined into a single signal) in order to customize (i.e., control and/or change) the penetration depth of the stimulation signal light 89.

One component useful to make the system more functional, in some embodiments, is a probe (such as probe 520 or probe 920) that integrates both the electrical and optical (generating infrared optical signals for nerve stimulation and/or visible optical signals for indicating where the infrared is or will be pointing) stimulators. Some embodiments provide such an EO probe that can be used in the EO system. In other embodiments, two or more probes are used to deliver the electrical and optical signals to the site where stimulation is desired. Insert graphs 981 and 982 in FIG. 9 show hypothetical plots of intensity (i) as a function of time (t) for an electrical-pulse signal 981 that alone is sub-threshold (somewhat less than a signal sufficient) for initiating an NAP, and for an optical-pulse signal 982 that alone is sub-threshold for initiating an NAP.

Figure 10A:
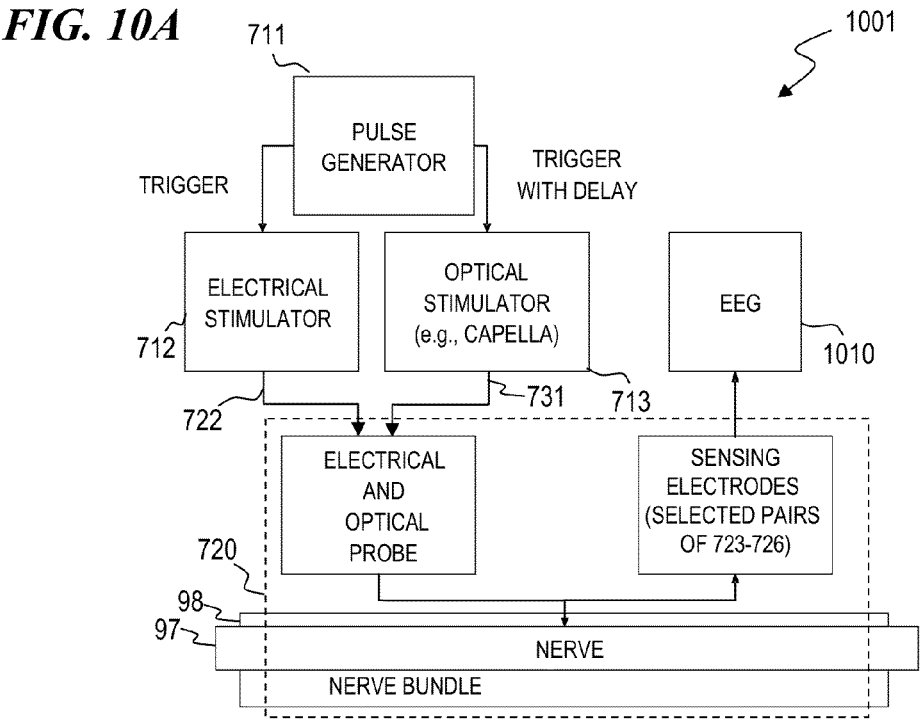
FIG. 10A is a system schematic of the electrical optical hybrid stimulator 1001 according to some embodiments of the invention.
Figure 10B:
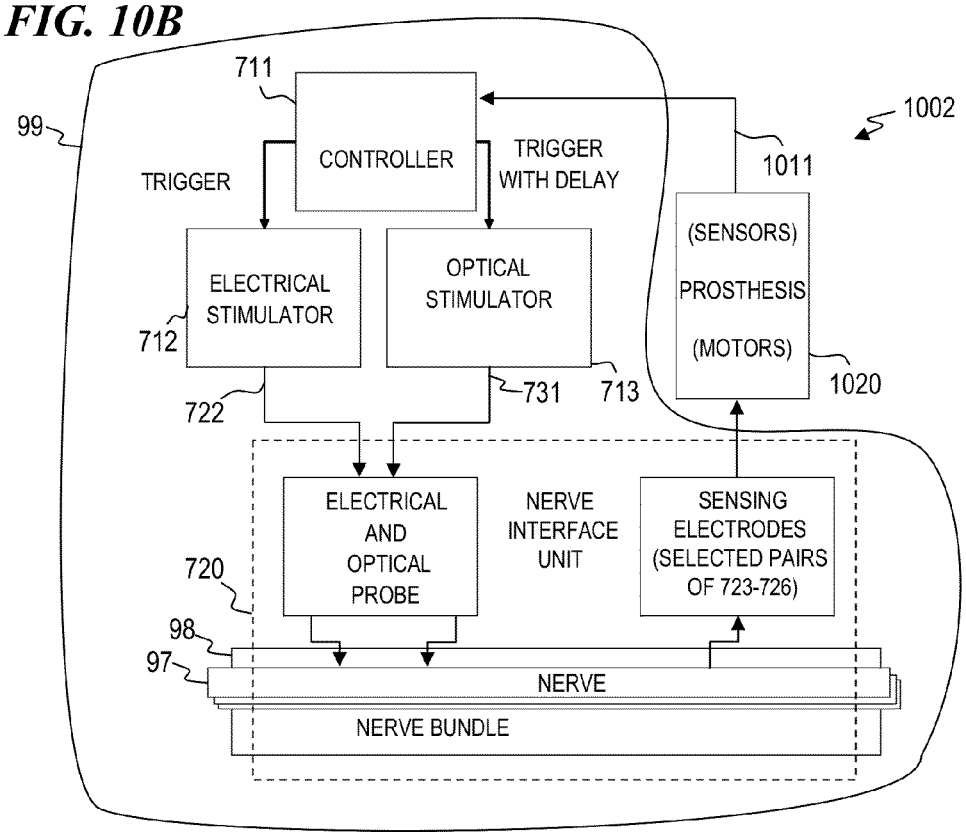
FIG. 10B is a system schematic of the electrical optical hybrid stimulator and prosthesis system 1002 according to some embodiments of the invention.

FIG. 10A is a system schematic of the electrical-optical-hybrid stimulator 1001 according to some embodiments. In some embodiments, an EEG (electroencephalograph) system 1010 is used to record electrical activity of areas of the brain and/or other nerve signals. Other aspects and referenced elements of FIG. 10A are as described above for FIG. 7A, FIG. 7B, FIG. 8 and FIG. 9. In some embodiments, the sensing electrode is formed from two or more of the electrodes of the fine-pitched electrode array of the electrodes 723, 724, 725, and 726.

FIG. 10B is a system schematic of the electrical-optical-hybrid stimulator and prosthesis system 1002 according to some embodiments of the invention. In some embodiments, prosthesis system 1002 includes the electrical-optical-hybrid stimulator 700 as described above for FIG. 7A and FIG. 7B, as well as an interface that is connected to prosthesis 1020. In some embodiments, sensed signals from electrodes 723, 724, 725, and/or 726 (i.e., sensed motor-nerve signals) are used to control actuators and/or motors in prosthesis 1020 (e.g., in some embodiments, an artificial or "bionic" arm or leg, wherein the motors control the various rotations, extensions, opening, closing and other motor functions of the arm being replaced), while sensors in the prosthesis 1020 generate signals 1011 based on measurements of the environment (e.g., the weight, texture, temperature, moistness, or other attributes of something being touched or grasped), and these sensed signals are used by controller 711 to generate the appropriate electrical and optical signals to trigger NAPs in the various different sensory nerves 97 in order to convey the sensed information as feedback to the brain of the patient 99 connected to the prosthesis system 1002. In some embodiments, most of system 1002 is implanted within patient 99.

In some embodiments, the probe is connected to both an optical stimulator such as the Capella™ model R1850 infrared optical-signal nerve stimulator (available from Lockheed Martin Aculight Corporation, 22121 20th Avenue S.E., Bothell, Wash. 98021 USA) and an electrical nerve stimulator such as an S88 Grass electrical stimulator (available from Astro-Med Inc., Grass Technologies Product Group, 600 East Greenwich Avenue, West Warwick, R.I. 02893 USA) in order to provide both types of stimulus. In addition to the two stimulators, a pulse generator is used to trigger each stimulator with a single input trigger in some embodiments. In some embodiments the pulse generator also has the ability to initiate the electrical stimulation first and then trigger the optical stimulation.

FIG. 11(*a*) and FIG. 11(*b*) show the results of combining optical stimulation with electrical stimulation. FIG. 11(*a*) is a graph 1101 of optical energy (the vertical axis as a % of threshold) required to reach stimulation threshold (to trigger a response) as a function of sub-threshold electrical stimulus (the horizontal axis as a % of threshold of electrical stimulation needed to trigger a response); and FIG. 11(*b*) is a graph 1102 of optical energy (the vertical axis as a % of threshold) required to reach stimulation threshold as a function of the time delay between a pulse of electrical stimulation (set at a level of 90% of threshold) and the pulse of optical stimulation.

FIG. 11(*a*) demonstrates the effects of combining electrical and optical stimulation. Data points reflect the amount of optical energy (% INS threshold) required to reach the stimulation threshold when applied concurrently with an electrical stimulus (% electrical stimulation threshold). The best-fit line models the data incorporating the known endpoints where 100% of either modality alone is required to reach the stimulation threshold. Interestingly, the data do not fit a linear relationship. Rather, in some embodiments, the required optical energy can be predicted by a logarithmic relationship:

$$O=0.22 \ln(1-E)+1, \qquad \text{(Equation 1)}$$

with $R^2=0.56$, where O is the optical energy (% INS threshold), and E is the magnitude of the electrical stimulus (% electrical stimulation threshold). The data in FIG. 11(*a*) and FIG. 11(*b*) show significant variance that can be attributed to inter- and intra-animal variability; limitations of the experimental setup—in particular, the spatial localization of the stimulation electrodes and fiber optic; and the fact that near the electrical-stimulation threshold (the steep part of the curve), minor fluctuations in electrical stimulation may result in significant changes in optical energy required. Equation 1 above is one example relationship derived from a particular set of animal experiments. The other parameters described throughout this specification and its Figures are also exemplary of various experiments performed by the inventors. In other embodiments, the fundamental combination of electrical and optical stimulation could vary in results based on the tissue type and on the way in which each of the stimuli are delivered (e.g., the position and shape of each electrode, the probe position and optics used to deliver the light pattern and the like), and thus in those embodiments, the Equation 1 is modified (e.g., based on empirical measurements and parameter variations) or empirically derived based on the tissue type, location and on the individual patient who is being stimulated.

If the electrical stimulus is applied at 95% of the electric threshold, then the optical threshold will be reduced by a factor of nearly 3 according to Equation 1. For 80% or 90% of threshold, the optical threshold is reduced by 1.54-fold and 2.03-fold, respectively. This reduction in optical threshold significantly increases the window for safe INS, as less energy is required to stimulate, thereby reducing the heat load in the tissue. If the ratio of damage threshold to stimulation threshold for INS alone is assumed to be 2:1, as reported by Wells et al. (see reference 6), the inventors can predict that applying an electrical stimulus at 90% of electrical stimulation with INS will increase this ratio to 4.05:1. For electrical stimuli at 80% and 95%, the ratio is predicted to be approximately 3.10:1 and 5.87:1, respectively. Threshold radiant exposures for INS alone averaged 1.69 plus-or-minus 0.30 $J/cm^2$. Combined with a sub-threshold electrical stimulus, radiant exposures were reduced to 1.49 plus-or-minus 0.22 $J/cm^2$ at 60% of electrical threshold and 0.60 plus-or-minus 0.29 $J/cm^2$ at 95% of electrical threshold. While the INS threshold radiant exposures reported here (using a 400-μm-diameter fiber) are higher than those previously published for the rat sciatic nerve (and above the published radiant exposures for thermal damage) that were obtained using a 600-μm-diameter fiber (see reference 6), this can be accounted for by the known fiber-diameter dependence of thermal distributions as well as known morphological changes over the length of the nerve. In addition, there are several subtle differences in the laser parameters and endpoint definition between the current and previously reported results. Thus, a direct comparison between these absolute values should be made with caution. No visible indication of thermal damage was present at the radiant exposures used in the current study.

FIG. 11(b) demonstrates the effects of delaying the optical stimulus relative to the electrical stimulus. In some embodiments, the results indicate that the greatest benefit (effectiveness in stimulating a nerve-action-potential (NAP) response) is achieved when the electrical and optical pulses are delivered simultaneously. In some embodiments, for delays (between the end of the electrical pulse and delivering the optical pulse) up to 1 msec, the radiant exposure (the amount of energy in the optical pulse) necessary for stimulation appears to increase linearly. In some embodiments, for delay times greater than one millisecond (>1 msec), combining the modalities (i.e., combining the optical stimulus with the electrical stimulus) provides minimal benefits because, in some of those embodiments, 100% of the optical threshold (the threshold amount of optical energy needed if only optical energy is used) is needed to achieve stimulation of the NAP response.

In some embodiments, the optical pulse and the electrical pulse are delivered such that they overlap in time; e.g., in some embodiments, the optical pulse is about 1-2 msec, and an electrical pulse having a duration of about 10-50 microseconds is applied while the optical pulse is being delivered.

In some other embodiments, the optical stimulus is delivered prior to the delivery of the electrical stimulus. In some embodiments, the electrical stimulus is delivered after a non-zero delay of up to 1 msec after the end of the optical stimulus. In some embodiments, the electrical stimulus is delivered about 1 msec after the end of the delivery of the optical stimulus. In some embodiments, the electrical stimulus is delivered after a delay of more than 1 msec and no more than about 2 msec after the end of the delivery of the optical stimulus. In some embodiments, the electrical stimulus is delivered after a delay of more than 2 msec and no more than about 3 msec after the end of the delivery of the optical stimulus. In some embodiments, the electrical stimulus is delivered after a delay of more than 3 msec and no more than about 4 msec after the end of the delivery of the optical stimulus. In some embodiments, the electrical stimulus is delivered after a delay of more than 4 msec and no more than about 5 msec after the end of the delivery of the optical stimulus. In some embodiments, the electrical stimulus is delivered after a delay of more than 5 msec after the end of the delivery of the optical stimulus.

In some preferred embodiments, the optical pulse is about 1-2 msec, the optical pulse ends and there is a delay of about 1 msec or so, then an electrical pulse having a duration of about 10-50 microseconds is applied.

In some embodiments, the optical pulse and the electrical pulse are applied as a temporally sequential pair, wherein the optical pulse is applied alone first, then after a non-zero delay the electrical pulse is applied alone, wherein the duration of the optical pulse is non-zero but no more than 0.1 msec, wherein the duration (as a full-width half-maximum (FWHM) measurement of the time of the leading-edge half maximum value of the optical pulse and the time of the falling-edge half maximum value of the optical pulse) of the optical pulse is in a range of 0.1 msec to 0.2 msec inclusive, of 0.2 msec to 0.4 msec inclusive, of 0.4 msec to 1 msec inclusive, of 1 msec to 2 msec inclusive, of 2 msec to 4 msec inclusive, or of 4 msec to 10 msec inclusive (i.e., non-zero up to 0.1 msec, or subranges of the range 0.1 msec to 10 msec); the delay (as a measurement between the time of the falling-edge half maximum value of the optical pulse and the time of the leading-edge half maximum value of the electrical pulse) between the end of the optical pulse and the start of the electrical pulse is in a range of 0.001 msec to 0.01 inclusive, a range of 0.01 msec to 0.02 msec inclusive, a range of 0.02 msec to 0.04 msec inclusive, a range of 0.04 msec to 0.1 msec inclusive, 0.1 msec to 0.2 msec inclusive, of 0.2 msec to 0.4 msec inclusive, of 0.4 msec to 1 msec inclusive, of 1 msec to 2 msec inclusive, of 2 msec to 4 msec inclusive, or of 4 msec to 10 msec inclusive (i.e., subranges of the range 0.001 msec to 10 msec); and the duration (as an FWHM measurement) of the electrical pulse is in a range of 0.005 msec to 0.01 msec, of 0.01 msec to 0.02 msec, of 0.02 msec to 0.04 msec, of 0.04 msec to 0.08 msec, of 0.08 msec to 0.1 msec, or of 0.1 msec to 0.2 msec (i.e., subranges of the range 0.005 msec to 0.20 msec).

In some embodiments, the start of the electrical stimulus is before and separated in time from the start of the optical stimulus by a period of time suitable to optimize the desired stimulation. In some such embodiments, the electrical stimulation is kept "on" substantially constantly or at least until the optical stimulation is applied. In some embodiments, the time period between the start of the delivery of the electrical stimulus and the start of the delivery of the optical stimulus that follows the start of the electrical stimulation is about 0.01 msec. In some embodiments, the time period between the start of the delivery of the electrical stimulus and the start of the delivery of the optical stimulus that follows the start of the electrical stimulation is 5 msec±10%.

In other embodiments, the start of the delivery of the electrical stimulus is between 0.01 msec and 0.02 msec inclusive after the start of the delivery of the optical stimulus. In some embodiments, the start of the delivery of the electrical stimulus is between 0.02 msec and 0.05 msec inclusive after the start of the delivery of the optical stimulus. In some embodiments, the start of the delivery of the electrical stimulus is between 0.05 msec and 0.1 msec inclusive after the start of the delivery of the optical stimulus.

In some embodiments, the start of the delivery of the electrical stimulus is between 0.1 msec and 0.2 msec inclusive the start of after the delivery of the optical stimulus. In some embodiments, the start of the delivery of the electrical stimulus is between 0.2 msec and 0.5 msec inclusive after the start of the delivery of the optical stimulus. In some embodiments, the start of the delivery of the electrical stimulus is between 0.5 msec and 1 msec inclusive after the start of the delivery of the optical stimulus.

In some embodiments, the start of the delivery of the electrical stimulus is between 1 msec and 2 msec inclusive after the start of the delivery of the optical stimulus. In some embodiments, the start of the delivery of the electrical stimulus is between 2 msec and 5 msec inclusive after the start of the delivery of the optical stimulus. In some embodiments, the start of the delivery of the electrical stimulus is between 5 msec and 10 msec inclusive after the start of the delivery of the optical stimulus.

In some embodiments, the time period between the delivery of the electrical stimulus and the delivery of the optical stimulus is between 10 msec and 15 msec inclusive. In some embodiments, the time period between the delivery of the electrical stimulus and the delivery of the optical stimulus is between 15 msec and 20 msec inclusive. In some embodiments, the time period between the delivery of the electrical stimulus and the start of the delivery of the optical stimulus is between 20 msec and 25 msec inclusive. In some embodiments, the time period between the delivery of the electrical stimulus and the delivery of the optical stimulus is between 25 msec and 30 msec inclusive. In some embodiments, the time period between the start of the delivery of the electrical stimulus and the start of the delivery of the optical stimulus is between 30 msec and 50 msec inclusive. In some embodiments, the time period between the start of the delivery of the electrical stimulus and the start of the delivery of the optical stimulus is between 50 msec and 100 msec inclusive. In some embodiments, the time period between the start of the delivery of the electrical stimulus and the start of the delivery of the optical stimulus is between 100 msec and 200 msec inclusive. In some embodiments, the time period between the start of the delivery of the electrical stimulus and the start of the delivery of the optical stimulus is between 200 msec and 300 msec inclusive. In some embodiments, the time period between the start of the delivery of the electrical stimulus and the start of the delivery of the optical stimulus is between 300 msec and 500 msec inclusive.

In some embodiments, the time period between the start of the delivery of the electrical stimulus and the start of the delivery of the optical stimulus is 10 msec±10%. In some embodiments, the time period between the start of the delivery of the electrical stimulus and the start of the delivery of the optical stimulus is 20 msec±10%. In some embodiments, the time period between the start of the delivery of the electrical stimulus and the start of the delivery of the optical stimulus is 30 msec±10%. In some embodiments, the time period between the start of the delivery of the electrical stimulus and the start of the delivery of the optical stimulus is 40 msec±10%. In some embodiments, the time period between the start of the delivery of the electrical stimulus and the start of the delivery of the optical stimulus is 50 msec±10%. In some embodiments, the time period between the start of the delivery of the electrical stimulus and the start of the delivery of the optical stimulus is 100 msec±10%. In some embodiments, the time period between the start of the delivery of the electrical stimulus and the start of the delivery of the optical stimulus is 150 msec±10%. In some embodiments, the time period between the start of the delivery of the electrical stimulus and the start of the delivery of the optical stimulus is 200 msec±10%. In some embodiments, the time period between the start of the delivery of the electrical stimulus and the start of the delivery of the optical stimulus is 250 msec±10%. In some embodiments, the time period between the start of the delivery of the electrical stimulus and start of the delivery of the optical stimulus is 300 msec±10%. In some embodiments, the time period between the start of the delivery of the electrical stimulus and the start of the delivery of the optical stimulus is 400 msec±10%. In some embodiments, the time period between the start of the delivery of the electrical stimulus and the start of the delivery of the optical stimulus is 500 msec±10%. In some embodiments, the time period between the start of the delivery of the electrical stimulus and the start of the delivery of the optical stimulus is greater than 550 msec.

FIG. 12(a) and FIG. 12(b) show that spatial selectivity is maintained with combined optical and electrical stimulation. FIG. 12(a) is a plot 1201 of the average of 20 consecutive recordings of CMAPs from electrodes placed in biceps femoris; and FIG. 12(b) is a plot of the same recordings as FIG. 12(a), but for electrodes placed in gastrocnemius. FIG. 12(a) and FIG. 12(b) illustrate that the spatial selectivity of INS is preserved in this combined stimulation modality. Note how the stimulated CMAP is present in only one muscle group.

New data of the inventors demonstrates that a preferred embodiment of the method may be optimized when the optical pulse is delivered at least as much as 30 milliseconds before the electrical pulse in some cases and when the optical pulse is delivered at least as much as 30 milliseconds after the electrical pulse. This new data includes the experimentation described below.

Nerve Fiber Recruitment in the Context of Hybrid Neural Stimulation

Recently, for some embodiments, hybrid neural stimulation combining optical and electrical techniques was shown to provide spatially selective activation of nerve fibers with optical radiant exposures up to a factor of three (3) less than for infrared nerve stimulation (INS) alone (see reference 1). The mitigated risk of thermally-induced damage and reduced pulse energies make hybrid nerve stimulation attractive for biomedical applications requiring spatial selectivity, but where laser power constraints and tissue damage are primary concerns. Some embodiments use a full parametric study to determine the combination(s) of electrical current and optical energy for optimally reducing optical-pulse energies and tissue-damage risk.

In demonstrating feasibility of hybrid stimulation in the rat sciatic nerve, the inventors' results showed a large variability in the reduction of optical pulse energies (see reference 1). In these experiments, the electrical threshold was set at a chosen sub-threshold current and the additional optical radiant exposure ($J/cm^2$) simultaneously applied was determined as a percent of the optical threshold radiant exposure. The results indicated that the reduction of optical radiant exposures by hybrid stimulation varied by as much as a factor of ten (10). In some embodiments, the source of this variability must be identified and controlled for the further development and ultimate application of hybrid neural stimulation.

The inventors investigated how the spatial component of nerve fiber recruitment contributes to the overall reliability and repeatability of hybrid stimulation. There are two aspects of the spatial component of which the inventors addressed: 1) The relative locations of the optical and electrical stimuli and 2) the strength of the optical stimulus as a function of the location. The mechanism of INS was shown to involve a thermal gradient (see reference 2). Thus, it is assumed that the thermal gradient and the electrical current path, in some embodiments, overlap spatially. However, what is not known is where this overlap should occur. The activating function, which describes the transmembrane potentials leading to the electrical activation of a neuron, results in neurons closest to the cathode being activated first (see references 3, 4). Experimentally, stimulation threshold current is shown to increase with increasing distance from the cathode (see reference 5). Given that the electrical stimulus preferentially targets neurons nearest the cathode, the inventors hypothesize that hybrid stimulation will exhibit the lowest optical pulse energies when the optical stimulus is located along the electrical current path and adjacent to the cathode. Like electrical stimulation, increasing INS radiant exposures results in recruitment of additional nerve fibers. Therefore, the inventors expect that for a given sub-threshold electrical stimulus, an increase in the sub-threshold optical stimulus will yield an increase in the size of the region of excitability for hybrid stimulation.

METHODS: In some embodiments, experiments were performed using Aplysia californica weighing 200-300 g (Marinus Scientific, Long Beach, Calif.), which were maintained in an aerated aquarium containing circulating artificial seawater (ASW) (Instant Ocean; Aquarium Systems, Mentor, Ohio) kept at 16-17° C. The animals were fed dried seaweed every 1-3 days.

Aplysia were anesthetized with an injection of MgCl2 (50% of body weight) prior to dissection. Once anesthetized, animals were dissected and the buccal ganglia were removed and pinned in a recording dish and immersed in Aplysia saline (i.e., 460 mM NaCl, 10 mM KCl, 22 mM $MgCl_2$, 33 mM $MgSO_4$, 10 mM $CaCl_2$, 10 mM glucose, 10 mM HEPES (4-(2-hydroxyethyl)-1-piperazineethanesulfonic acid)), pH 7.6). For each experiment, the nerve of interest was anchored in place by pinning the protective sheath around the nerve to the Sylgard base (Dow Corning, Midland, Mich.) of the recording dish. Once securely pinned, the nerve to be investigated was suctioned into a nerve recording electrode to monitor the response to stimulation. Nerve suction recording electrodes were made by hand-pulling polyethylene tubing over a flame to the desired thickness. Recording electrodes were suction-filled with Aplysia saline prior to suctioning of the nerve. Nerve signals were amplified and band-pass filtered (300-500 Hz) using an AC-coupled differential amplifier (model 1700; A-M Systems), digitized (Axon Digidata 1440A; Molecular Devices, Sunnyvale, Calif.) and recorded (Axograph X; Axograph Scientific).

Extracellular stimulating electrodes were made from thin-wall boroscilicate capillary glass (catalogue #615000; A-M Systems, Everett, Wash.) pulled to resistances of about 0.2 MS2 (PC-10; Narishige). Electrodes were capillary filled with Aplysia saline. Electrical currents were supplied by a bipolar stimulus isolator (A365R; WPI). For optical stimulation, a tunable pulsed diode laser source (Capella; Lockheed-Martin-Aculight, Bothell, Wash.) provided pulses of infrared light (in some embodiments, having a wavelength $\lambda$=1.875 µm) through a flat-polished 100 µm optical fiber (Ocean Optics, Dunedin, Fla.).

Two glass pipettes were positioned in contact with the nerve, one on each side of the nerve, to provide bipolar stimulation with a transverse current path. Pipettes were positioned such that their angle of approach to the nerve was as shallow as was allowed by the edge of the recording dish. The optical fiber was introduced vertically, approximately perpendicular to the nerve. All nerve stimulation was coordinated through computer software (Axograph X). Electrical and optical pulse durations were 100 microseconds (100 µsec) and 3 milliseconds (3 msec), respectively. For hybrid stimulation, the pulses were synchronized such that they ended simultaneously. Nerve recordings were triggered and acquired for 10 msec prior to stimulation through 150 msec post stimulation.

To investigate the spatial component of axonal recruitment, the optical fiber was translated across the nerve between the stimulating pipettes using a micromanipulator. A CMOS color USB camera and accompanying software (catalogue #59-367; Edmund Optics, Barrington, N.J.) were used to acquire a movie of the position of the optical fiber. An LED was triggered by the computer software to flash during the recordings for documenting the position of the optical fiber at the time of stimulation.

All movie files and data were analyzed with custom software (Matlab r2010b; Mathworks, Natick, Mass.).

RESULTS: A 100 µm optical fiber was translated transversely across the buccal nerves of Aplysia californica to determine how the spatial relationship between the optical and electrical stimuli may contribute to the variability of previously demonstrated hybrid stimulation data (see reference 1). When translating the optical fiber back and forth across the nerve, it was determined that, in some embodiments, there exists a finite region where hybrid stimulation is possible (see, for example, FIG. 14). There was variation in the size and shape of evoked responses between animals, nerves as well as different locations within a single nerve, suggesting that multiple axons were recruited over the course of the experiments.

After identifying the existence of a finite region of excitability (ROE) for some embodiments, the inventors investigated how the strength of the optical stimulus altered its size. With electrical stimulation at 90% of threshold, the inventors compared ROE size for optical stimuli of 0.14 and 0.37 mJ/pulse. A total of 30 measurements were acquired from 7 nerves from 7 animals. The results showed that, in some embodiments, the ROE was reduced in size approximately a factor of 2 by reducing the optical stimulus from 0.37 mJ/pulse to 0.14 mJ/pulse.

Figure 16A:
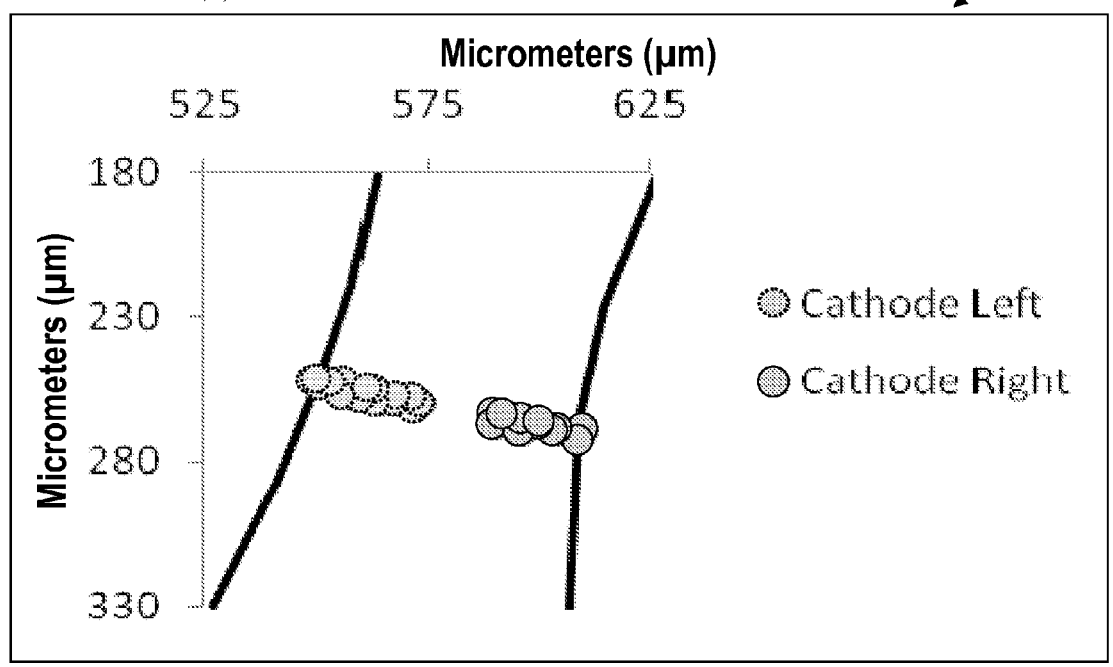
FIG. 16($a$) is a plot 1601 illustrating the location of the ROE for a first nerve.
Figure 16B:
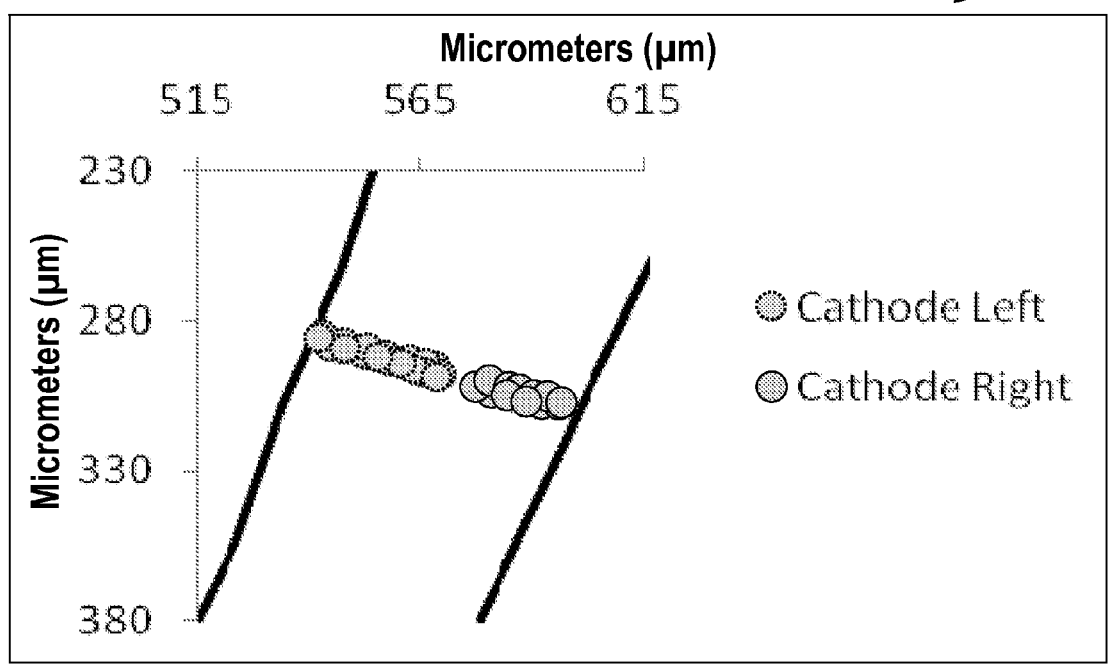
Figure 16C:
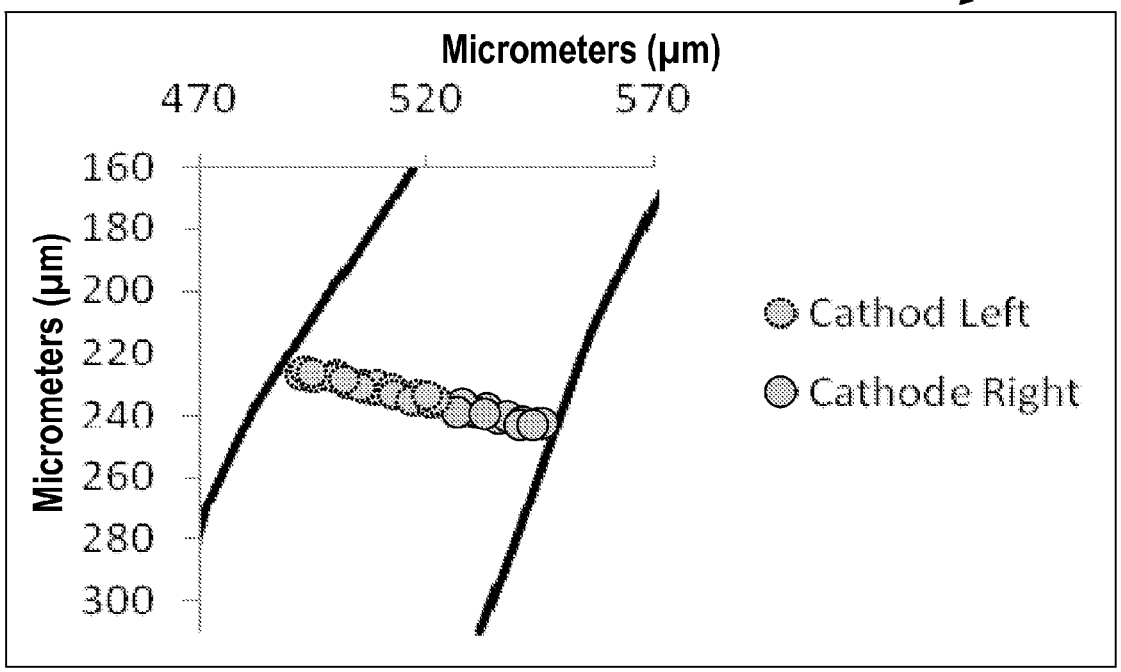
Figure 16D:
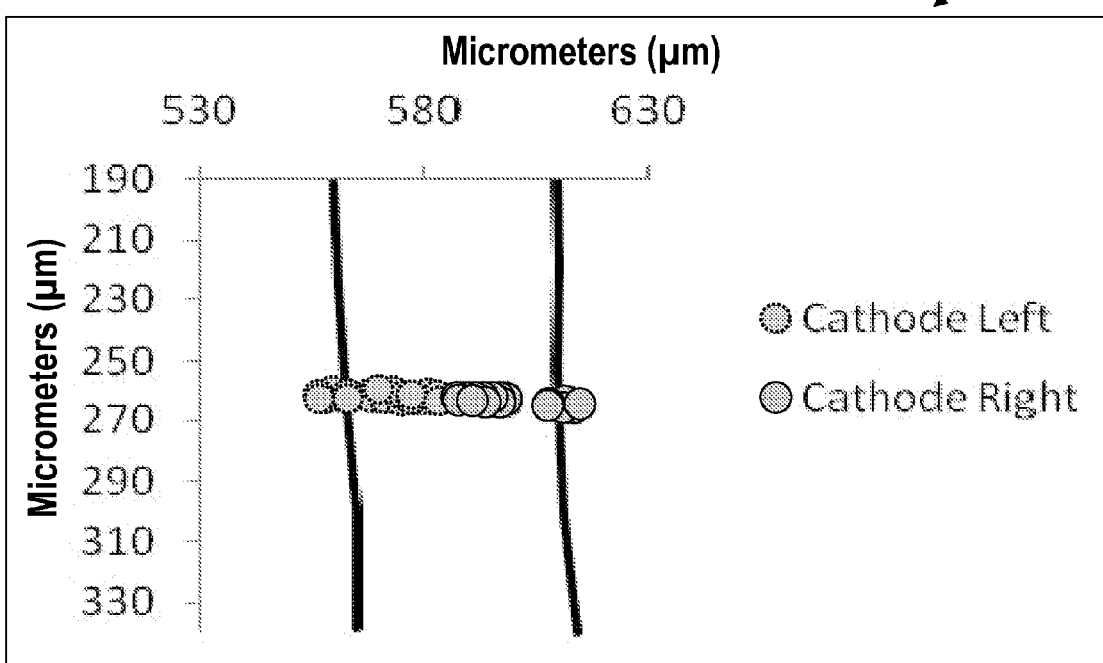
Figure 17A:
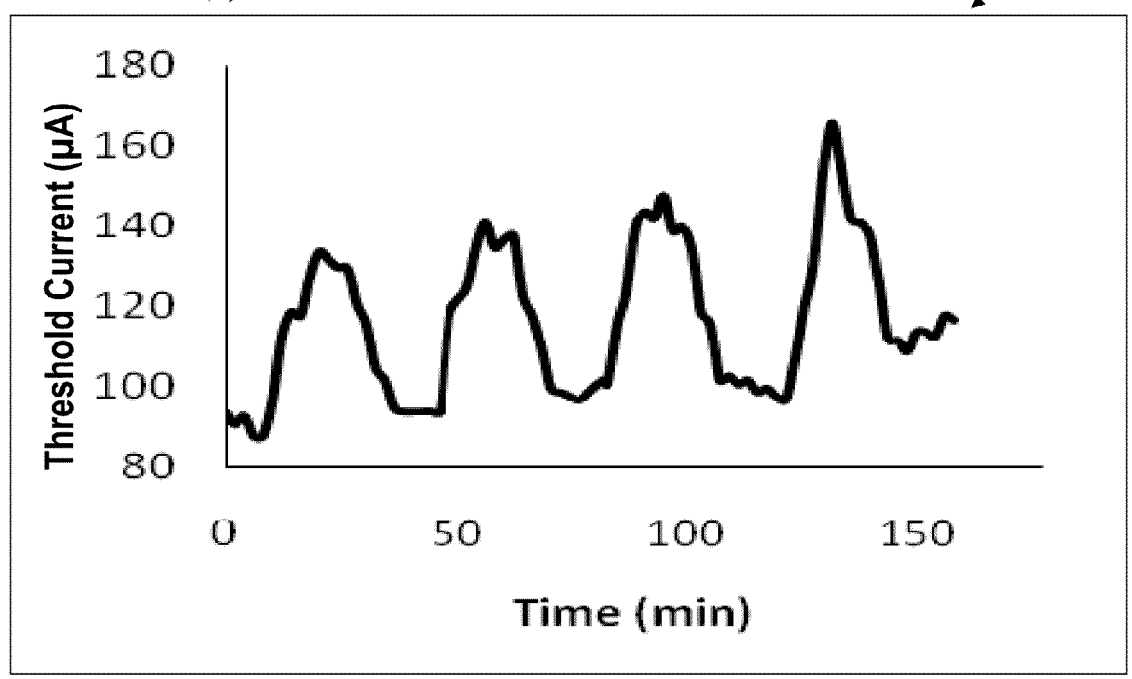
FIG. 17($a$) is a plot 1701 of threshold current (μA) versus time (minutes) with measurements made every two minutes.
Figure 17B:
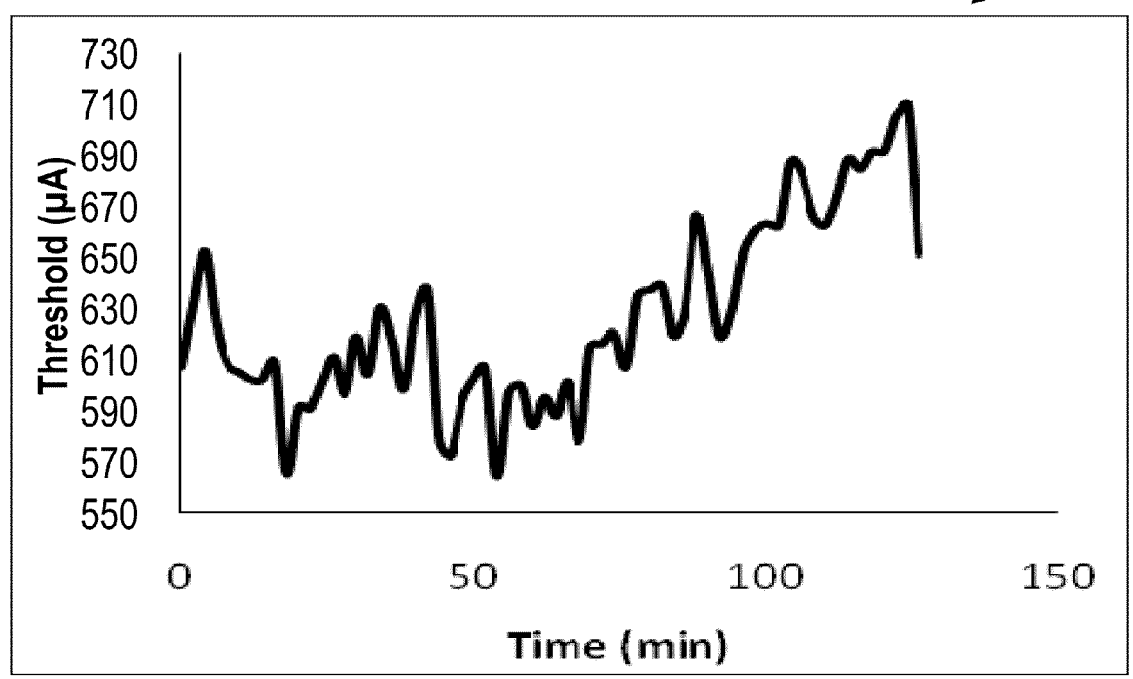
Figure 17C:
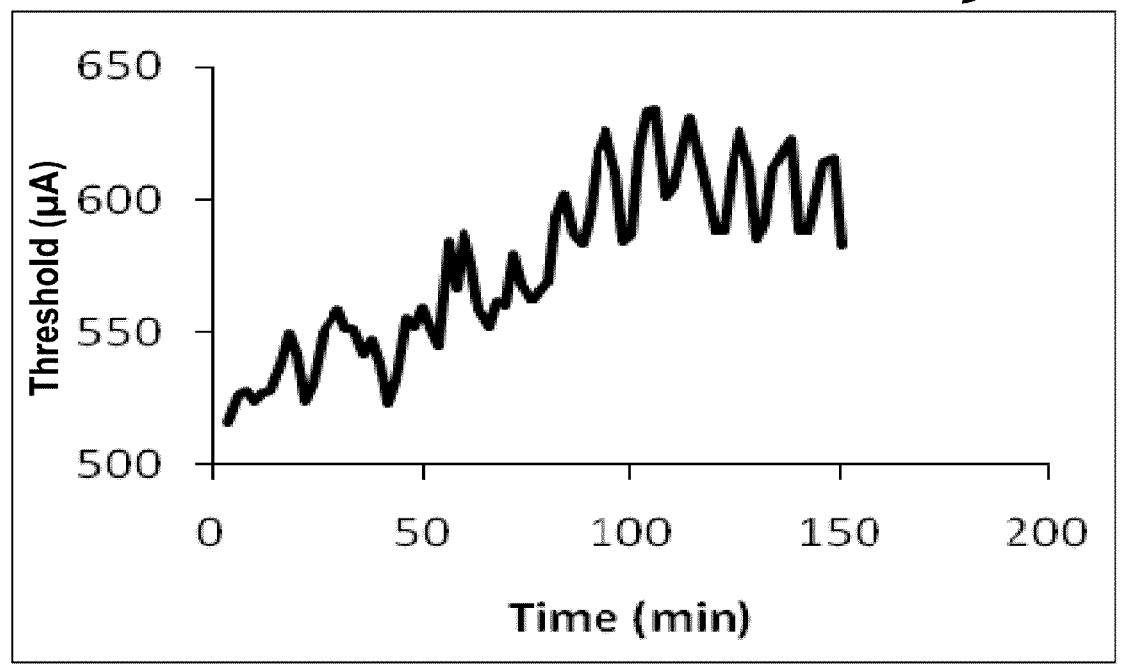
Figure 17D:
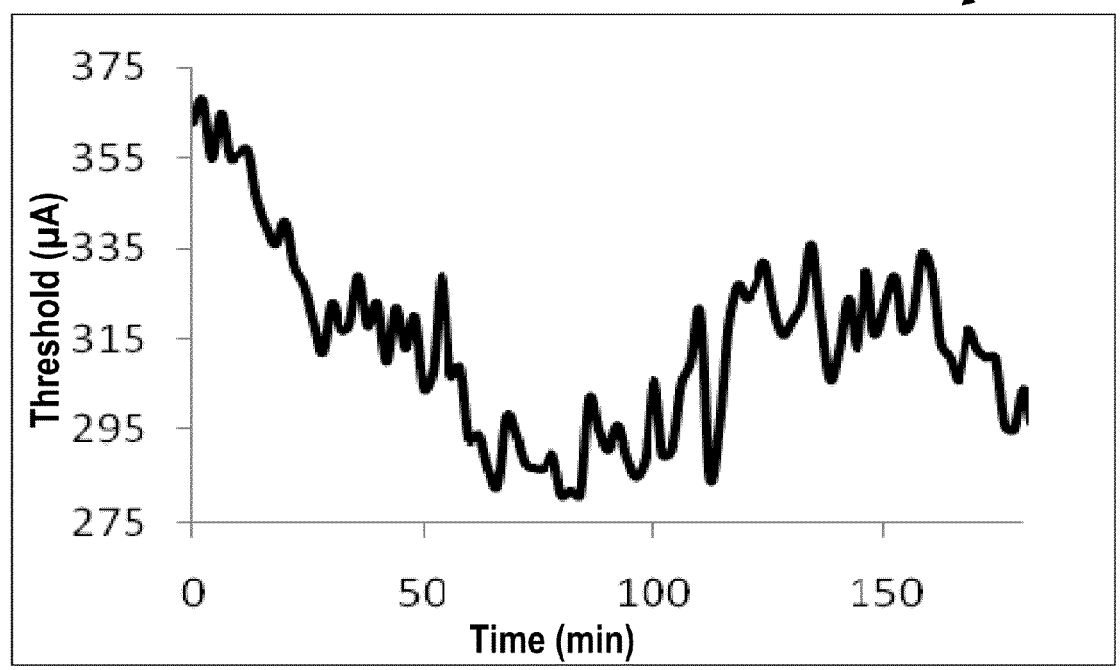

In the course of demonstrating the existence of a finite region of excitability for some embodiments, it was observed that the location of the ROE was always adjacent to the cathode of the bipolar electrical stimulus for these embodiments. The inventors then hypothesized that within a single nerve, the location of the ROE could be steered by changing the polarity of the electrical stimulus. To test this hypothesis, the electrical stimulation threshold was determined for a chosen polarity and subsequently reduced to 90% of threshold. A constant optical stimulus (0.37 mJ/pulse) was then applied with the electrical stimulus, while the optical fiber was translated back and forth across the nerve. Then, the process was repeated for the opposite polarity. This experiment was repeated across a total of 4 nerves from 3 different animals yielding 8 polarity pairs. The results clearly demonstrated that for a given electrode arrangement, two unique ROEs may, in some embodiments, be achieved by simply switching the direction of the current path (see FIGS. 16(a), (b), (c), and (d)).

DISCUSSION: The initial demonstration of hybrid neural stimulation showed that this modality holds great promise; however, initially there was only minimal understanding as to its mechanism or how to reliably employ its benefits (see reference 1). In an effort to better understand—and gain improved control over—hybrid stimulation, the inventors have investigated how the spatial relationship of the two modalities contributes to the ability (or inability) to activate neural tissue. Specifically, the inventors have examined the size and location of the region of excitability for hybrid stimulation. The inventors' experiments have led to three important conclusions about the how the spatial configuration contributed to hybrid stimulation.

Conclusion #1: The inventors' experiments show that, for some embodiments, there exists a finite spatial region of excitability along the nerve diameter where hybrid stimulation will occur for a given electrode/fiber configuration. Here the inventors have found that a limited ROE does exist for each nerve the inventors investigated. It should be noted that the ROE is along the line directly between the two stimulating pipettes and is defined to include any hybrid stimulation within that region. In most cases, only one action potential was observed as a result of hybrid stimulation. However, in a few of the experiments the inventors observed a second stimulated response that was, in some cases, bounded by a smaller ROE. These results imply that while hybrid stimulation is selective, strict spatial precision may not be required to achieve selectivity (see reference 1). While in many cases the ROE bounds were strictly defined, in some instances there was a small transition from no stimulation to full excitation. The inventors expect that positioning the optical fiber at the bounding edge of the ROE may contribute to variability in a parametric evaluation or other systematic investigation due to the potential for inconsistent firing.

Conclusion #2: For some embodiments, the size of the spatial region of excitability for hybrid stimulation is determined by the strength (the amount of energy) of the optical component. After demonstrating the existence of a finite ROE, the inventors proceeded to determine if the size of the ROE was fixed or if a narrower/broader ROE could be achieved. By combining a sub-threshold electrical stimulus (90% of threshold) with two different optical pulse energies (0.14 and 0.37 mJ/pulse) the inventors determined that the size of the ROE scales with the optical stimulus in some embodiments.

This characteristic of hybrid stimulation is likely a main contributor to observed variability in earlier data. For instance, suppose one were trying to determine how the sub-threshold electrical stimulus affects the additional optical energy required for stimulation as in (see reference 1). It is possible that, if the optical fiber were not positioned consistently from one nerve to the next, that pulse energies for the optical component of hybrid stimulation will vary. In fact, FIG. 15(a) and FIG. 15(b) show that in the same nerve, for some embodiments, there are locations of the optical fiber where 0.37 mJ/pulse will stimulate but 0.14 mJ/pulse will not. For other fiber locations, either 0.37 mJ/pulse or 0.14 mJ/pulse will stimulate a nerve-action potential response. However, if the experimenter does not take into account the fact that the optical fiber should be placed consistently, the stimulation thresholds may vary wildly from animal to animal.

Our results are not indicative of the maximum or minimum size of the ROE. As the optical fiber used for these experiments was on par with the diameter of the buccal nerves, it may be possible to achieve a significantly smaller ROE using a smaller diameter optical fiber. However, due to laser constraints, the inventors were unable to generate sufficient optical energies from a smaller-than-100-micron diameter (<100-μm diameter) optical fiber.

Conclusion #3: For some embodiments, the location of the region of excitability is determined by the polarity of the electrical stimulus. Thus, in some embodiments, the location of the region of excitability may be steered by altering the electrical current path. While identifying the presence of a finite ROE, it was observed that, for some embodiments, the location of the ROE was always located adjacent to the cathode. By changing the polarity of the electrical stimulus to reverse the current path, the inventors were able to shift the ROE to the side of the nerve adjacent to the "new" cathode. This result is important for future design considerations as the inventors seek to develop a hybrid neural stimulation implant. By reversing the polarity, the inventors effectively have the ability to choose which region is excited between two electrical contacts.

REFERENCES

1. A. R. Duke, J. M. Cayce, J. D. Malphrus, P. Konrad, A. Mahadevan-Jansen and E. D. Jansen, "Combined optical and electrical stimulation of neural tissue in vivo," Journal of Biomedical Optics 14(6), 060501-060503 (2009);
2. J. Wells, C. Kao, P. Konrad, T. Milner, J. Kim, A. Mahadevan-Jansen and E. D. Jansen, "Biophysical mechanisms of transient optical stimulation of peripheral nerve," Biophysical Journal 93(7), 2567-2580 (2007);
3. J. Holsheimer, "Principles of neurostimulation," Pain Research and Clinical Management 15(17-36 (2003);
4. F. Rattay, "Analysis of models for external stimulation of axons," IEEE Trans Biomed Eng 33(10), 974-977 (1986); and
5. J. B. Ranck, Jr., "Which elements are excited in electrical stimulation of mammalian central nervous system: a review," Brain Res 98(3), 417-440 (1975), each of which is incorporated herein by reference in its entirety.

Hybrid stimulation is a novel nerve stimulation paradigm combining optical and electrical stimulation into a single nerve stimulation modality. In some embodiments, the goal of this technology is to take advantage of the desirable features of each modality while mitigating their limitations. Feasibility of hybrid stimulation was recently demonstrated in the rat sciatic nerve. While combining optical stimulation with a sub-threshold electrical stimulus was shown to reduce threshold radiant exposures ($J/cm^2$) by as much as three-fold, in some embodiments, a noticeable amount of variability was present in the data.

For the successful optimization and application of hybrid stimulation, the sources of the variability should be identified so that they may be controlled. In this work the inventors have investigated two potential sources of variability in the successful application of hybrid stimulation: 1) Spatial, and 2) Temporal.

METHODS: The buccal ganglion of *Aplysia californica* were dissected and pinned to a Sylgard dish bathed in *Aplysia* saline. Nerve response were recorded using a polyethylene suction electrode filled with *Aplysia* saline. Nerve signals were amplified (1000×), band-pass filtered (300-500 Hz), digitized and recorded. Extracellular stimulating electrodes were made from thin-wall borosilicate capillary glass pulled to resistances of about 0.2 MΩ and filled with *Aplysia* saline. For optical stimulation, a tunable pulsed diode laser source provided pulses of infrared light through either a 100- or 200-μm-diameter fiber. Glass pipettes were positioned in contact with the nerve, one on each side of the nerve, to provide bipolar stimulation with a transverse current path. Pipettes were positioned such that their angle of approach to the nerve was as shallow as was allowed by the edge of the recording dish.

The optical fiber was introduced vertically to the nerve and was positioned just off of the nerve's protective sheath. Electrical and optical pulses were 100 μsec and 3 msec, respectively and were synchronized by software such that they ended simultaneously.

Figure 13A:
FIG. 13($a$) is a photomicrograph of a hybrid-stimulation experimental setup 1301 showing the positioning of glass-pipette electrodes and a 200 μm optical fiber.

FIG. 13(a) is a photomicrograph of a hybrid-stimulation experimental setup 1301 showing the positioning of glass-pipette electrodes and a 200-micron (200-μm) optical fiber.

Figure 13B:
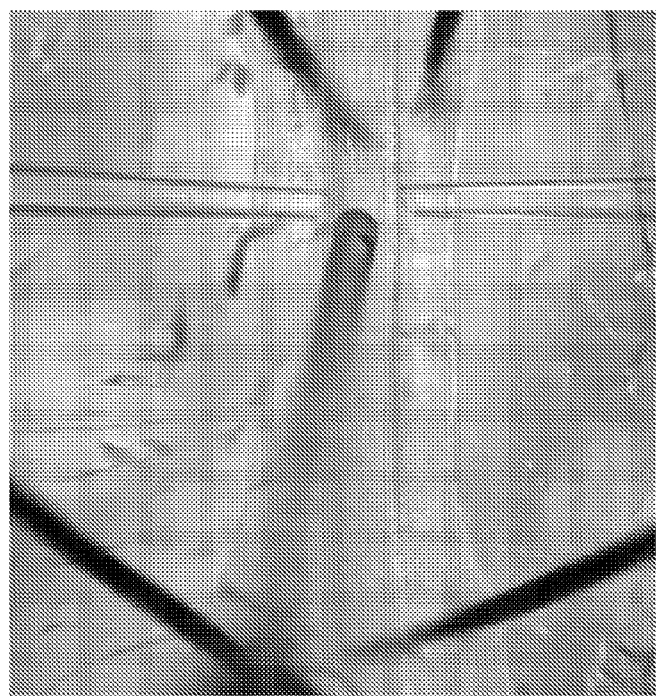

FIG. 13(b) is a photomicrograph of a hybrid-stimulation experimental setup 1302 showing the positioning of glass-pipette electrodes and a 100-μm optical fiber.

To investigate the spatial source of variability, the optical fiber was translated across the nerve between the stimulating pipettes using a micromanipulator. A video of the fiber's location was recorded. An LED was triggered to flash in the field of view simultaneously with stimulation so that the nerve recordings could be correlated to fiber position.

To investigate the temporal source of variability, threshold currents were measured every 2 min for several hours.

In some embodiments, there are two scenarios where transient threshold currents may affect hybrid stimulation—

Scenario One: The electrical threshold is measured followed by immediate manual changes to the applied current prior to a subsequent hybrid stimulation episode; and Scenario Two: Electrical threshold is measured and the applied current is reduced sub-threshold, but the optical component of the hybrid stimulus is allowed to fluctuate with time.

To investigate how transient threshold currents play a role in Scenario One, every two minutes (2 min) the electrical threshold was found, reduced to 90% and the additional optical energy required for stimulation was immediately determined.

To investigate how transient threshold currents play a role in Scenario Two, every 2 min the electrical threshold was found, reduced to 90% and then 5 pulse trains (5 seconds, 1 Hz) having different pulse energies were consecutively added to the sub-threshold stimulus.

The order of intensity for each of the pulse trains was randomized to account for any effects associated with cumulative stimulation.

Figure 14:
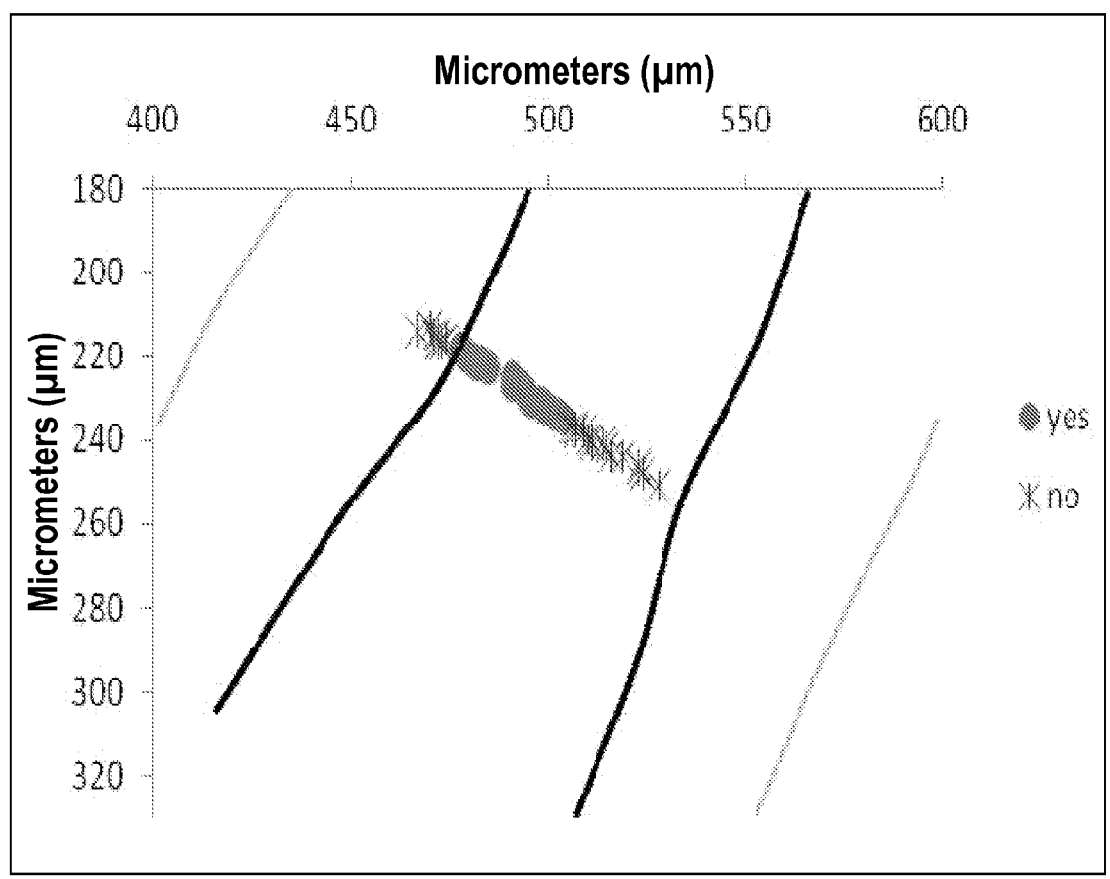
FIG. 14 is a plot 1401 of the finite region of excitability (ROE) where hybrid stimulation was found to occur in some embodiments of the present invention.

(1) Spatial Results (which Repeat the Spatial Conclusions Set Forth Above):

Conclusion #1: For some embodiments, there exists a finite region of excitability (ROE) where hybrid stimulation will occur. FIG. 14 is a plot 1401 of the finite region of excitability (ROE) where hybrid stimulation was found to occur in some embodiments of the present invention.

Conclusion #2: For some embodiments, the size of the ROE is determined by the strength of the optical stimulus. FIG. 15($a$) is a plot 1501 of the size of the ROE when a 1.78 J/cm$^2$ optical stimulus was applied. FIG. 15($b$) is a plot 1502 of the size of the ROE when a 4.71 J/cm$^2$ optical stimulus was applied. FIG. 15($c$) is a table 1503 summarizing the data associated with the experiments that produced FIG. 15($a$) and FIG. 15($b$).

Conclusion #3: For some embodiments, the location of the ROE is determined by the polarity of the electrical stimulus. Thus, in some embodiments, the location of the ROE may be steered by altering the electrical current path. FIG. 16($a$) is a plot 1601 illustrating the location of the ROE for a first nerve. FIG. 16($b$) is a plot 1602 illustrating the location of the ROE for a second nerve. FIG. 16($c$) is a plot 1603 illustrating the location of the ROE for a third nerve. FIG. 16($d$) is a plot 1604 illustrating the location of the ROE for a fourth nerve.

The data for FIGS. 16($a$), ($b$), ($c$), and ($d$) were produced using three (3) animals, and four (4) different nerves (including eight (8) separate polarity pairs).

(2) Temporal Results:

FIG. 17($a$) is a plot 1701 of threshold current (μA) versus time (minutes) with measurements made every two minutes.

FIG. 17($b$) is a plot 1702 of threshold current (μA) versus time (minutes) with measurements made every two minutes.

FIG. 17($c$) is a plot 1703 of threshold current (μA) versus time (minutes) with measurements made every two minutes.

FIG. 17($d$) is a plot 1704 of threshold current (μA) versus time (minutes) with measurements made every two minutes.

Figure 18A:
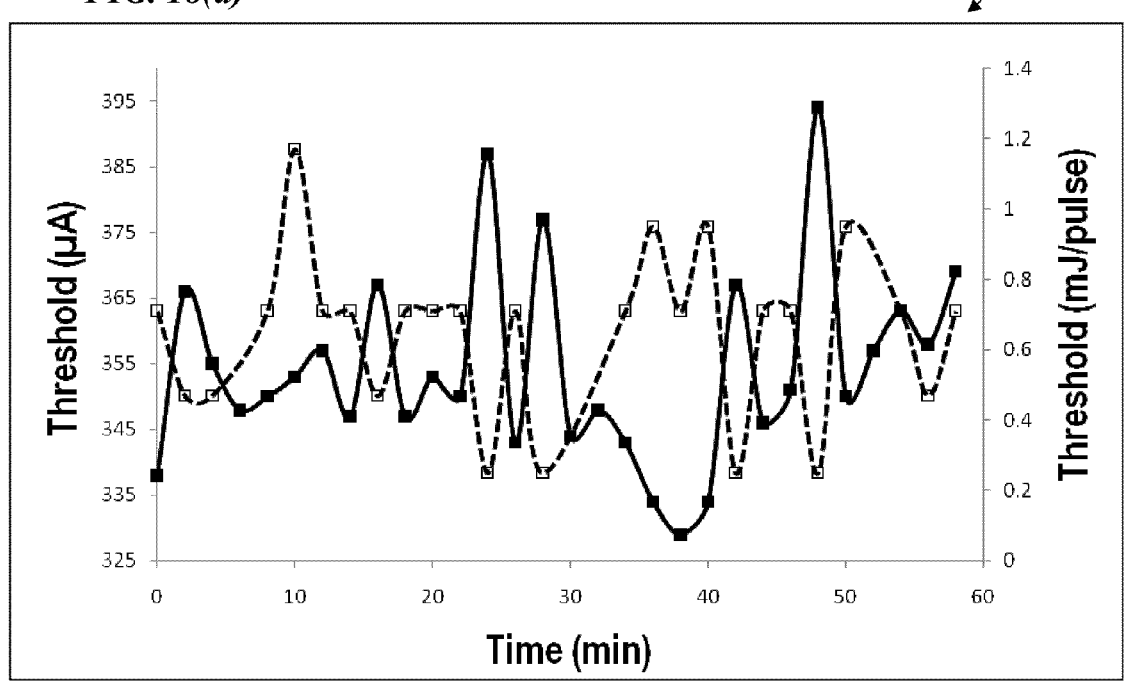
FIG. 18($a$) is a plot 1801 of threshold electrical current (μA) (solid line) and hybrid optical threshold (mJ/pulse) (dotted line) versus time (minutes).
Figure 18B:
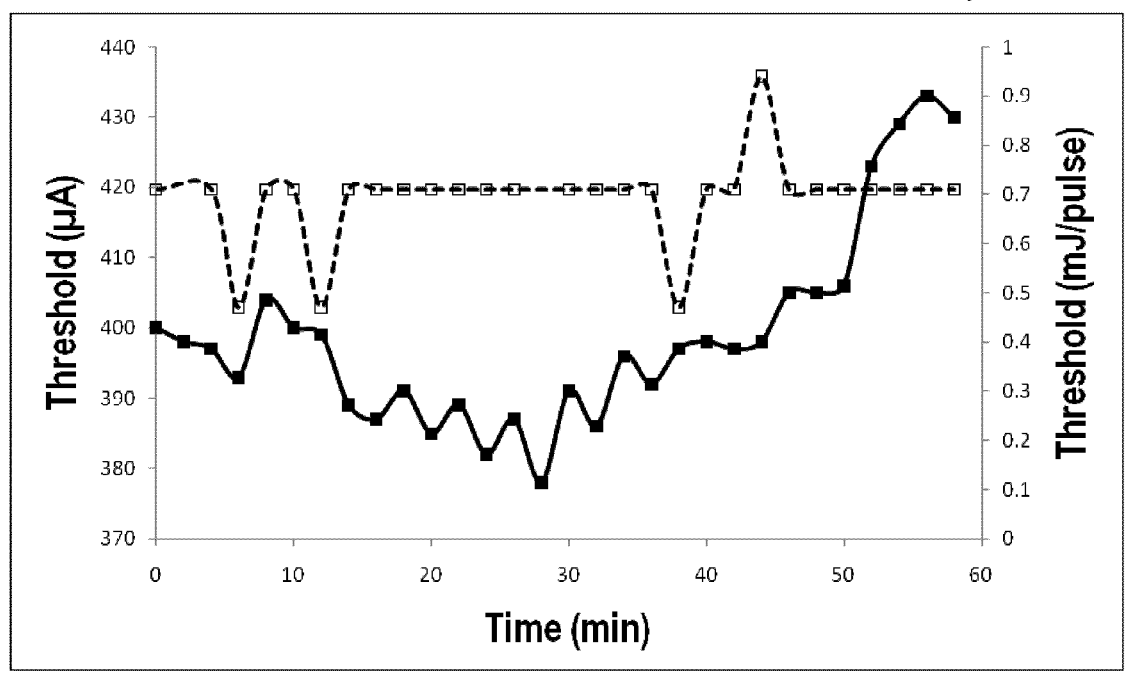

FIG. 18($a$) and FIG. 18($b$) were generated based on the following experimentation: Every 2 min: find electrical threshold; reduce to 90%; and add 5 pulses each of 0.25, 0.47, 0.71, 0.95 and 1.17 mJ/pulse in random order. Pulse energy yielding 5/5 response is said to be the "threshold" amount of energy.

FIG. 18($a$) is a plot 1801 of threshold electrical current (μA) (solid line) and hybrid optical threshold (mJ/pulse) (dotted line) versus time (minutes). The hybrid optical threshold is the additional optical energy per pulse added to the electric current pulse (having a magnitude that is 90% of the threshold electrical current) that is required for stimulation.

FIG. 18($b$) is a plot 1802 of threshold electrical current (μA) (solid line) and hybrid optical threshold (mJ/pulse) (dotted line) versus time (minutes).

In some embodiments, the data obtained are not as clear as anecdotal evidence: When electrical threshold is sharply rising, hybrid/optical threshold also rises (because one would think one is at 90%, but one is steadily falling lower). When electrical threshold is sharply falling, hybrid/optical threshold also rises (because one would think one is at 90%, but one is steadily approaching 100%).

(3) Key Observation

In the course of performing the experiments described above, it was noticed that the combination of electrical and optical stimulation not only operates a stimulation modality, but will also cause inhibition in some embodiments. More specifically:

Conclusion #4: For some embodiments, there is a window of radiant exposures outside of which hybrid stimulation is not possible. To investigate this, the inventors performed an experiment in which the inventors:

Found the electrical stimulation threshold and set the applied electrical current to 90% of threshold;

Increased the optical energy to find where hybrid stimulation starts and stops; and Decreased optical energy back through the same range of pulse energies to check repeatability of stimulation window.

FIG. 19 is a table 1901 summarizing the window of radiant exposures outside of which hybrid stimulation is not possible for some embodiments.

In some embodiments, the present invention provides a method for fine-pitched electrical and optical stimulation that includes generating and applying both a fine-pitched electrical stimulation signal to a portion of a nerve, and a fine-pitched optical stimulation signal to the portion of the nerve in order to trigger a nerve action potential (NAP) in vivo. In some embodiments, the method further includes compressing the nerve in order to space apart certain subportions of the nerve in order to improve selectivity of the applied electrical and optical signals. In some embodiments, the applying of the fine-pitched electrical stimulation includes applying a voltage in a direction that is transverse across the portion of the nerve. In some embodiments, the applying of the fine-pitched electrical stimulation includes applying a voltage in a direction that is longitudinal along the portion of the nerve. In some embodiments, the applying of the fine-pitched electrical stimulation includes applying a voltage in a direction that is both transverse across and longitudinal along the portion of the nerve.

Some embodiments of the method further include detecting a nerve action potential (NAP). In some embodiments, the detection of the NAP is used as feedback control to the generating and applying of the electrical stimulation signal and the optical stimulation signal.

In some embodiments, the fine-pitched electrical signal is applied to a selected subset (e.g., to a pair) selected from a plurality of electrodes that are spaced on a center-to-center distance of about 1000 microns or less. In other embodiments, the center-to-center spacing of the plurality of electrodes is about 500 microns or less. In other embodiments, the center-to-center spacing of the plurality of electrodes is about 300 microns or less. In other embodiments, the center-to-center spacing of the plurality of electrodes is about 200 microns or less. In other embodiments, the center-to-center spacing of the plurality of electrodes is about 100 microns or less. In other embodiments, the center-to-center spacing of the plurality of electrodes is about 50 microns or less. In some embodiments, the plurality of electrodes includes a first subset that is located along a first perimeter of a nerve-interface unit that surrounds the nerve of a human patient. In some embodiments, the plurality of electrodes further includes a second subset that is located along a second perimeter of the nerve-interface unit that is longitudinally spaced from the first perimeter.

In some embodiments, the fine-pitched optical signal is launched from to a selected subset (e.g., from one) selected from a plurality of optical emitters that are spaced on a center-to-center distance of about 1000 microns or less. In some embodiments, the plurality of optical emitters includes a first subset that are spaced apart from one another and located along a first perimeter (e.g., the bottom half of an inside perimeter) of a nerve-interface unit that surrounds the nerve of a human patient. In some embodiments, the plurality of optical emitters further includes a second subset that are located along a second perimeter (e.g., along the top half of the inside perimeter opposite the bottom inside perimeter) of the nerve-interface unit. In other embodiments, the center-to-center spacing of the plurality of optical emitters is about 500 microns or less. In other embodiments, the center-to-center spacing of the plurality of optical emitters is about 300 microns or less. In other embodiments, the center-to-center spacing of the plurality of optical emitters is about 200 microns or less. In other embodiments, the center-to-center spacing of the plurality of optical emitters is about 100 microns or less. In other embodiments, the center-to-center spacing of the plurality of optical emitters is about 75 microns or less. In other embodiments, the center-to-center spacing of the plurality of optical emitters is about 50 microns or less. In other embodiments, the center-to-center spacing of the plurality of optical emitters is about 25 microns or less. In other embodiments, the center-to-center spacing of the plurality of optical emitters is about 10 microns or less.

In some embodiments, the present invention provides an apparatus for fine-pitched electrical and optical stimulation that includes an electrical-signal generator that is coupled to a plurality of spaced-apart electrodes and operable to selectively apply a fine-pitched electrical stimulation signal to a portion of a nerve, and an electrical-signal generator operatively coupled to emit an optical-stimulation signal to the portion of the nerve in order to trigger a nerve action potential (NAP) in vivo. In some embodiments, the apparatus is configured to compress the nerve in order to space apart certain subportions of the nerve in order to improve selectivity of the applied electrical and optical signals. In some embodiments, a subset of the plurality of spaced-apart electrodes is configured to apply a voltage in a direction that is transverse across the portion of the nerve. In some embodiments, a subset of the plurality of spaced-apart electrodes is configured to apply a voltage in a direction that is longitudinal along the portion of the nerve. In some embodiments, a subset of the plurality of spaced-apart electrodes is configured to apply a voltage in a direction that is both transverse across and longitudinal along the portion of the nerve.

Some embodiments of the apparatus further include a nerve action potential (NAP) detector configured to sense a NAP and to output a signal representative of the NAP. In some embodiments, the signal from the detector is coupled to the electrical-signal generator and the optical-signal generator and used as feedback control to the generation and application of the electrical-stimulation signal and the optical-stimulation signal.

In some embodiments, the fine-pitched electrical signal is applied to a selected subset (e.g., to a pair) selected from a plurality of electrodes that are spaced on a center-to-center distance of about 1000 microns or less. In other embodiments, the center-to-center spacing of the plurality of electrodes is about 500 microns or less. In other embodiments, the center-to-center spacing of the plurality of electrodes is about 300 microns or less. In other embodiments, the center-to-center spacing of the plurality of electrodes is about 200 microns or less. In other embodiments, the center-to-center spacing of the plurality of electrodes is about 100 microns or less. In other embodiments, the center-to-center spacing of the plurality of electrodes is about 50 microns or less. In some embodiments, the plurality of electrodes includes a first subset that is located along a first perimeter of a nerve-interface unit that surrounds the nerve of a human patient. In some embodiments, the plurality of electrodes further includes a second subset that is located along a second perimeter of the nerve-interface unit that is longitudinally spaced from the first perimeter.

In some embodiments, the fine-pitched optical signal is launched from to a selected subset (e.g., from one) selected from a plurality of optical emitters that are spaced on a center-to-center distance of about 1000 microns or less. In some embodiments, the plurality of optical emitters includes a first subset that are spaced apart from one another and located along a first perimeter (e.g., the bottom half of an inside perimeter) of a nerve-interface unit that surrounds the nerve of a human patient. In some embodiments, the plurality of optical emitters further includes a second subset that are located along a second perimeter (e.g., along the top half of the inside perimeter opposite the bottom inside perimeter) of the nerve-interface unit. In other embodiments, the center-to-center spacing of the plurality of optical emitters is about 500 microns or less. In other embodiments, the center-to-center spacing of the plurality of optical emitters is about 300 microns or less. In other embodiments, the center-to-center spacing of the plurality of optical emitters is about 200 microns or less. In other embodiments, the center-to-center spacing of the plurality of optical emitters is about 100 microns or less. In other embodiments, the center-to-center spacing of the plurality of optical emitters is about 75 microns or less. In other embodiments, the center-to-center spacing of the plurality of optical emitters is about 50 microns or less. In other embodiments, the center-to-center spacing of the plurality of optical emitters is about 25 microns or less. In other embodiments, the center-to-center spacing of the plurality of optical emitters is about 10 microns or less.

In some embodiments, the apparatus further includes a stimulation-to-nerve mapping software that controls outputting of various electrical and optical signals and detects (e.g., using indications from the patient) to empirically map which signals stimulate which nerve pathways.

In some embodiments, the present invention provides a method that includes applying a combination of both an electrical stimulation signal and an optical stimulation signal to trigger a nerve action potential (NAP) in vivo. In some embodiments, the present invention provides a method that includes generating an electrical stimulation signal and an optical stimulation signal; and applying a combination of both the electrical stimulation signal and the optical stimulation signal to a living animal to trigger a nerve action potential (NAP) in vivo.

In some embodiments, the optical stimulation signal is of a nature such that if applied alone the optical signal has a low probability of triggering a NAP. In some such embodiments, the optical-only probability is no more than 0.5 (i.e., wherein a NAP occurs on no more than 50% of applied optical signals). In some such embodiments, the probability is no more than 0.4 (a NAP occurring on no more than 40% of applied optical signals). In some such embodiments, the probability is no more than 0.3 (a NAP occurring on no more than 30% of applied optical signals). In some such embodiments, the probability is no more than 0.25 (a NAP occurring on no more than 25% of applied optical signals). In some such embodiments, the probability is no more than 0.2 (a NAP occurring on no more than 20% of applied optical signals). In some such embodiments, the probability is no more than 0.15 (a NAP occurring on no more than 15% of applied optical signals). In some such embodiments, the probability is no more than 0.1 (a NAP occurring on no more than 10% of applied optical signals). In some such embodiments, the probability is no more than 0.05 (a NAP occurring on no more than 5% of applied optical signals). In some such embodiments, the probability is no more than 0.01 (a NAP occurring on no more than 1% of applied optical signals).

In some embodiments, the electrical stimulation signal is of a nature such that if applied alone the electrical signal also has a low probability of triggering a NAP. In some such embodiments, the electrical-only probability is no more than 0.5 (a NAP occurring on no more than 50% of applied electrical signals). In some such embodiments, the electrical-only probability is no more than 0.4 (a NAP occurring on no more than 40% of applied electrical signals). In some such embodiments, the electrical-only probability is no more than 0.3 (a NAP occurring on no more than 30% of applied electrical signals). In some such embodiments, the electrical-only probability is no more than 0.25 (a NAP occurring on no more than 25% of applied electrical signals). In some such embodiments, the electrical-only probability is no more than 0.2 (a NAP occurring on no more than 20% of applied electrical signals). In some such embodiments, the electrical-only probability is no more than 0.15 (a NAP occurring on no more than 15% of applied electrical signals). In some such embodiments, the electrical-only probability is no more than 0.1 (a NAP occurring on no more than 10% of applied electrical signals). In some such embodiments, the electrical-only probability is no more than 0.05 (a NAP occurring on no more than 5% of applied electrical signals). In some such embodiments, the electrical-only probability is no more than 0.01 (a NAP occurring on no more than 1% of applied electrical signals).

Some embodiments of the method further include selectively applying a visible indication light signal that indicates a location that the optical stimulation signal is to be applied. Some embodiments of the method further include using a hybrid probe having an optical fiber inserted in an electrically conductive cannula; applying the optical-stimulation signal through the optical fiber; and applying the electrical-stimulation signal through the cannula. Some embodiments of the method further include using a second probe to obtain an electrical signal representative of the triggered NAP. In some embodiments, the hybrid probe further includes an electrode that is electrically separate from the cannula, and the method further includes using the electrode to obtain an electrical response signal representative of the triggered NAP. In some embodiments, the method further includes using the cannula to obtain an electrical response signal representative of the triggered NAP.

In some embodiments of the method, a signal representative of the electrical stimulation signal is subtracted from a signal obtained using the cannula to obtain the electrical response signal representative of the triggered NAP.

Some embodiments of the method further include using a hybrid probe having an optical fiber that has a metallization layer applied to the optical fiber; applying the optical-stimulation signal through the optical fiber; and applying the electrical-stimulation signal through the metallization layer. Some embodiments of the method further include using a second probe to obtain an electrical response signal representative of the triggered NAP. In some embodiments, the hybrid probe further includes an electrode that is electrically separate from the metallization layer, and the method further includes using the electrode to obtain an electrical response signal representative of the triggered NAP. Some embodiments of the method further include using the metallization layer to obtain an electrical response signal representative of the triggered NAP. In some embodiments, the applying of the combination of both the electrical stimulation signal and the optical stimulation signal includes using a plurality of electrodes configured to selectively apply the electrical stimulation signal in a direction that is both transverse and axial to a nerve pathway.

In some embodiments, the present invention provides an apparatus that includes an electrical-stimulation-signal source configured to selectively output an electrical stimulation signal; an optical-stimulation-signal source configured to selectively output an optical stimulation signal; and a controller operatively coupled to the electrical-stimulation-signal source and to the optical-stimulation-signal source and configured to control them to trigger a nerve action potential (NAP) in vivo, in animals, and in particular, animals who are human. In some embodiments of the apparatus, the optical stimulation signal is of a nature such that if applied alone the optical stimulation signal has a low probability to trigger a NAP (wherein the low probability is as described above). In some embodiments of the apparatus, the electrical stimulation signal is of a nature such that if applied alone the electrical stimulation signal has a low probability to trigger a NAP (wherein the low probability is as described above). In some embodiments of the apparatus, the optical stimulation signal is infrared, and the apparatus further includes a visible-indication-light-signal source configured to project visible light to indicate a location that the optical stimulation signal is to be applied.

Some embodiments of the apparatus further include a hybrid probe having an optical fiber inserted in an electrically conductive cannula, wherein the optical-stimulation signal is applied through the optical fiber and the electrical-stimulation signal is applied through the cannula. Some embodiments of the apparatus further include a second probe configured to obtain an electrical signal representative of the triggered NAP. In some embodiments of the apparatus, the hybrid probe further includes an electrode that is electrically separate from the cannula, wherein the electrode is configured to obtain an electrical signal representative of the triggered NAP. In some embodiments of the apparatus, the cannula is used to obtain an electrical signal representative of the triggered NAP.

In some embodiments of the apparatus, the apparatus is configured to subtract a signal representative of the electrical stimulation signal from a signal obtained using the cannula to obtain the electrical signal representative of the triggered NAP.

Some embodiments of the apparatus further include a hybrid probe having an optical fiber that has a metallization layer applied to the optical fiber, wherein the optical-stimulation signal is applied through the optical fiber and the electrical-stimulation signal is applied through the metallization layer. Some such embodiments further include a second probe configured to obtain an electrical signal representative of the triggered NAP. In some embodiments, the hybrid probe further includes an electrode that is electrically separate from the metallization layer, and is configured to obtain an electrical signal representative of the triggered NAP. In some embodiments, the apparatus is configured to use the metallization layer to obtain an electrical signal representative of the triggered NAP. Some embodiments further include a hybrid probe having a plurality of individually selectable optical emitters and a first plurality of individually selectable electrodes and at least one other electrode, wherein the optical-stimulation signal is propagated from one of the plurality of optical emitters and the electrical-stimulation signal is applied between a one or more of the first plurality of individually selectable electrodes and one or more of the at least one other electrode. In some embodiments, the controller is configured to supply signals to the hybrid probe to selectively apply the electrical stimulation signal in a direction that is both transverse and axial to a nerve pathway.

In some embodiments, the present invention provides an apparatus that includes means as described herein and equivalents thereof for generating an electrical stimulation signal and an optical stimulation signal; and means as described herein and equivalents thereof for applying a combination of both the electrical stimulation signal and the optical stimulation signal to a living animal to trigger a nerve action potential (NAP) in vivo. In some embodiments, of the apparatus, the applied optical stimulation signal is of a nature such that if applied alone the optical signal has a low probability to trigger a NAP, the probability being no more than 25%. In some embodiments, of the apparatus, wherein the applied electrical stimulation signal is of a nature such that if applied alone the electrical signal has a low probability to trigger a NAP, the probability being no more than 25%. In some embodiments, of the apparatus, the applied electrical stimulation signal is of a nature such that if applied alone the electrical signal has a low probability to trigger a NAP, the probability being no more than 25%. In some embodiments, the means for applying the combination of both the electrical stimulation signal and the optical stimulation signal includes a plurality of electrodes configured to selectively apply an electrical signal in a direction that is substantially axial to a nerve pathway. In some embodiments, the means for applying the combination of both the electrical stimulation signal and the optical stimulation signal includes a plurality of electrodes configured to selectively apply an electrical signal in a direction that is both transverse and axial to a nerve pathway. In some embodiments, the means for applying the combination of both the electrical stimulation signal and the optical stimulation signal includes a plurality of electrodes configured to selectively apply an electrical signal in a direction that is substantially transverse to a nerve pathway. In some embodiments, the electrical signal is applied from a plurality of the electrodes to a plurality of the electrodes in order to provide a substantially uniform electric field at least across the tissue that is stimulated by the optical signal that is applied concurrently with the electrical signal. In some embodiments, the applied electrical stimulation signal and the optical stimulation signal are applied to at least one tissue of the group consisting of peripheral nerves, central nervous system (CNS) neurons, spinal cord, spinal roots, cranial nerves, nerve endings, and cardiac tissues. In some embodiments, the means for applying the combination of both the electrical stimulation signal and the optical stimulation signal includes a plurality of electrodes configured to selectively apply an electrical signal in a direction that is substantially axial to a nerve pathway. In some embodiments, the means for applying the combination of both the electrical stimulation signal and the optical stimulation signal includes a plurality of electrodes configured to selectively apply an electrical signal in a direction that is both transverse and axial to a nerve pathway.

In some embodiments, the electrical portion of the hybrid probe is optimized or configured to uniformly distribute electrical energy across the optical zone of the target tissue (wherein the optical zone (region of interest) is (the laser-spot size) times (the laser-penetration depth)). This way, the entire area will stay below threshold and maintain a constant level of 'priming' such that the laser energy will reliably elicit a response without the need for excess energy to be applied. In some embodiments, the electrical portion of the hybrid probe deliver monopolar stimulation pulses from a single electrode located proximate the nerve to be stimulated (in some embodiments, the pulse is monophasic, i.e., unidirectional relative to a substantially constant background voltage), while in other embodiments, the electric portion of the probe delivers bipolar stimulation pulses (wherein, in some embodiments, the pulse is monophasic (as described above), while in other embodiments, the pulse is biphasic, i.e., bidirectional relative to a substantially constant background voltage) via a voltage applied between two electrodes (or electrical-contact leads) both located in the region of interest to provide current flow. In the case of two electrodes in the hybrid probe, the probe includes two selectively activated contact probes (two electrodes selected to have a voltage applied between them, these electrodes called cathode and anode) with the optical stimulus delivered to tissue between the two probes. It is thought that there is evidence that stimulation occurs at the cathode, but basically the injected waveforms can be optimized to be more-or-less uniformly distributed electric fields over the area of optical stimulation. In some embodiments, the electrodes that are not selected are not connected (i.e., high-Z or high impedance, wherein substantially no current flows in the non-selected electrodes). Again, in some embodiments, the voltage is applied between a first subset (having more than one electrode in the first subset) of the plurality of electrodes and a second subset (having more than one electrode in the first subset) of the plurality of electrodes, in order to provide a more uniform electric field across the volume (defined by the spot area and tissue-penetration depth of the laser output) of tissue being optical stimulated by the optical-stimulation signal.

In some embodiments, the electrical-and-optical-hybrid stimulations are applied to the following tissues in addition to peripheral nerves: neurons of the central nervous system, spinal cord, spinal roots, cranial nerves, nerve endings, and cardiac tissues.

In some embodiments, a plurality of optical emitters are located in both of two opposing inner surfaces of a hybrid probe, and the optical energy or power supplied by a selected optical emitter is limited in order to provide greater selectivity (i.e., a selected one of the optical emitters on one of the two surfaces is driven with an optical signal having a limited penetration depth in order to trigger responses only in the sub-portion of the nerve located closest to that surface, and alternatively a selected one of the optical emitters on the opposing-inner-side optical emitters is driven with an optical signal having a limited penetration depth in order to trigger responses only in the portion of the nerve closes to that opposing surface of the probe).

In some embodiments, the probe provides one or more arrays of closely spaced electrodes, wherein the electric stimulation signal is selectively applied from one or more of the electrodes to one or more of the other electrodes in the one or more arrays of electrodes.

In some embodiments, both the optical signal and the electrical signal are limited in power and area in order to further enhance the selectivity of the portion of the nerve that is triggered to have a NAP.

In some embodiments, the apparatus further includes a digital-delay generator configured to trigger the optical-stimulation device to apply the pulse of optical energy after a predetermined time delay determined by the digital-delay generator.

In some embodiments, the apparatus further includes a oscilloscope or similar instrument configured to measure an actual delay between the application of the sub-threshold-for-stimulation amount electrical current and the application of the pulse of optical energy, and sense, test and adjustment apparatus configured to sense the effectiveness of various different combinations of applied stimulation parameters and the resulting physiological response. In some embodiments, the stimulation parameters include two or more of the following: magnitudes of optical power (e.g., measured in watts), optical power density or radiant exposure (e.g., measured in watts per $cm^2$ on the tissue being stimulated), optical energy (e.g., measured in milliJoules) of one or more pulses, duration of the optical pulse, temporal shape of the optical pulse, the wavelength(s) of the optical pulse, the amount of ambient light, electrical voltage or current magnitudes, temporal shape of the electrical pulse, time delay between the start of the electrical pulse and the start of the optical pulse, the frequency of pulses, pulse repetition rate of pulses, or time interval between pulses of the stimulation, and other parameters. In some embodiments, the temporal shape of the optical and/or electrical pulses is square or substantially square (see, e.g., electrical signals 601, 603, 634, 635, 636, and 637 of FIG. 6B and optical signals 623, 624, 625, 626, and 627 of FIG. 6B). In other embodiments, the temporal shape of the optical and/or electrical pulses is any other suitable shape (such as ramped, temporally Gaussian, having a plurality of short pulses in a group, sine-wave, or the like) that optimizes the effect of the stimulation. In some embodiments, the resulting physiological response (e.g., a NAP, a muscle twitch or contraction) can be measured by a sensor or similar instrumentation, or a sensation (e.g., a perceived audio sensation, olfactory sensation, visual sensation, touch sensation, sense of balance or vertigo, taste sensation, or the like) can be reported or indicated by the patient, or the operation or function of a prosthesis can be observed or measured, and the measurement, observation, and/or report is, in some embodiments, used to calibrate or control the operation of the stimulation device.

In some embodiments, the present invention provides a system and method for triggering a response in a nerve and for reducing the power requirements of a system for in vivo optical-electrical stimulation of a nerve action potential (NAP) in neuronal tissue of a patient. In some embodiments, the system is implanted in the patient and is battery powered, such that it is desirable to reduce the power requirements for the circuits that deliver the optical and electrical stimulation (to save battery power), and/or to reduce the waste heat generated (to avoid tissue damage to the patient). In some embodiments, the power requirements of the system are reduced by reducing the threshold for optical stimulation (see description of FIG. 11(*a*)). In some embodiments, power efficiency for implantable neuroprostheses is very important because, in some embodiments, an implantable neuroprosthesis generates significant amounts of heat that can lead to damage to the prosthesis. In some embodiments, power efficiency is also important due to the desire to conserve battery life of the prosthesis.

In some embodiments, the system and method of the present invention is used with a plurality of device geometries and in a plurality of clinical applications. For example, in some embodiments, the present invention provides a hand-held probe for neurodiagnostics (see, e.g., FIG. 5) that is applied in a surgical setting such as nerve monitoring applications (facial nerve monitoring during tumor resection), carpel tunnel release, brachial plexus grafts/surgery, peripheral nerve reconstructions, cuff electrode placement, surface brain stimulation, spinal cord stimulation, or the like.

In some embodiments, the system and method of the present invention includes extraneural electrodes. In some embodiments, the extraneural electrodes are implantable, multi-channel neural interfaces that wrap around the surface of peripheral nerves. In some embodiments, the extraneural electrodes include flat interface nerve electrodes (FINE). In some embodiments, the extraneural electrodes include spiral electrodes. In some embodiments, the extraneural electrodes include cuff electrodes. In some embodiments, the extraneural electrodes include any other suitable electrode. In some embodiments, VCSELs or other laser sources are placed in-between the extraneural electrodes (see, e.g., FIG. 7A, FIG. 7B, and FIG. 7C), and in some such embodiments, the electrical stimulation includes monopolar, bipolar, tripolar electrical stimulation or the like.

In some embodiments, the system and method of the present invention includes intraneural or intrafassicular electrodes. In some embodiments, the intraneural electrodes are implantable, multi-channel neural interfaces that penetrate the peripheral nerve surface to bring the electrodes closer to the axons (thus reducing the electrical stimulation threshold). In some embodiments, the system and method of the present invention includes optical waveguides and intraneural (penetrating) electrodes that are configured to perform hybrid stimulation, and in some such embodiments, the electrical stimulation includes monopolar, bipolar, tripolar electrical stimulation or the like. In some embodiments, the optical waveguides include any configuration or tip shape suitable to carry light from outside the nerve to inside the nerve.

In some embodiments, the system and method of the present invention includes surface electrodes for cortical stimulation. In some embodiments, the system and method of the present invention includes penetrating electrodes for cortical stimulation, and/or deep brain stimulation of the thalamus or other deep brain structures. Some such embodiments are used for motor or sensory control, restoring the loss of any sense, treatment of epilepsy, Parkinson's, obesity, depression or other psychiatric disorders.

In some embodiments, the present invention provides a method for triggering a response in a nerve and for increasing a margin of safety for in vivo optical-electrical stimulation of a nerve action potential (NAP) in neuronal tissue of a patient, the method including applying a sub-threshold-for-stimulation amount electrical current through an area of the neuronal tissue; and applying a pulse of optical energy to a subportion of the volume of the neuronal tissue to which the electrical current has been applied in order to stimulate a nerve action potential in one or more neurons of the neuronal tissue.

In some embodiments, the pulse of optical energy has a duration of about 1 msec and is applied prior to the applying of the sub-threshold-for-stimulation amount of electrical current, wherein there is a delay of about 0.01 msec after the pulse of optical energy ends and before the applying of the sub-threshold-for-stimulation amount of electrical current begins, and wherein the applying of the sub-threshold-for-stimulation amount of electrical current has a duration of about 10 msec.

In some embodiments, the pulse of optical energy has a duration of about 1 msec and is applied prior to the applying of the sub-threshold-for-stimulation amount of electrical current, wherein there is a delay of about 0.1 msec after the pulse of optical energy ends and before the applying of the sub-threshold-for-stimulation amount of electrical current begins, and wherein the applying of the sub-threshold-for-stimulation amount of electrical current has a duration of about 10 msec.

In some embodiments, the pulse of optical energy has a duration of about 1 msec and is applied prior to the applying of the sub-threshold-for-stimulation amount of electrical current, wherein there is a delay of about 1 msec after the pulse of optical energy ends and before the applying of the sub-threshold-for-stimulation amount of electrical current begins, and wherein the applying of the sub-threshold-for-stimulation amount of electrical current has a duration of about 10 msec.

In some embodiments, there exists a threshold amount of optical energy needed to stimulate a nerve-action-potential response in the neuronal tissue when no electrical current is applied, and wherein with the application of the amount of electrical current, the optical energy of the optical pulse is less than 90% of the threshold amount of optical energy needed to stimulate a nerve action potential in the neuronal tissue when no electrical current is applied. In some embodiments, there exists a threshold amount of optical energy needed to stimulate a nerve-action-potential response in the neuronal tissue when no electrical current is applied, and wherein with the application of the amount of electrical current, the optical energy of the optical pulse is less than 80% of the threshold amount of optical energy needed to stimulate a nerve action potential in the neuronal tissue when no electrical current is applied. In some embodiments, there exists a threshold amount of optical energy needed to stimulate a nerve-action-potential response in the neuronal tissue when no electrical current is applied, and wherein with the application of the amount of electrical current, the optical energy of the optical pulse is less than 60% of the threshold amount of optical energy needed to stimulate a nerve action potential in the neuronal tissue when no electrical current is applied. In some embodiments, there exists a threshold amount of optical energy needed to stimulate a nerve-action-potential response in the neuronal tissue when no electrical current is applied, and wherein with the application of the amount of electrical current, the optical energy of the optical pulse is less than 40% of the threshold amount of optical energy needed to stimulate a nerve action potential in the neuronal tissue when no electrical current is applied.

In some embodiments, the pulse of optical energy stimulation is applied starting at a time delay of about 1 msec after the start of the electrical pulse having the sub-threshold-for-stimulation amount electrical current. In some embodiments, the pulse of optical energy is applied such that a leading edge half-maximum of the optical pulse occurs at a time delay of about 0.01 msec after a leading edge half-maximum of the sub-threshold-for-stimulation amount electrical current is applied. In some embodiments, the pulse of optical energy is applied such that a leading edge half-maximum of the optical pulse occurs at a time delay of about 1 msec after a leading edge half-maximum of the sub-threshold-for-stimulation amount electrical current is applied. In some embodiments, the pulse of optical energy is applied such that a leading edge half-maximum of the optical pulse occurs between about 1 msec and about 30 msec, inclusive, after a leading edge half-maximum of the sub-threshold-for-stimulation amount electrical current. In some embodiments, the sub-threshold-for-stimulation amount electrical current is applied such that a leading edge half-maximum of the electrical current occurs between about 0.01 msec and about 30 msec, inclusive, after a leading edge half-maximum of the pulse of optical energy.

In some embodiments, the sub-threshold-for-stimulation amount electrical current is applied such that a leading edge half-maximum of the electrical current occurs between about 1 msec and about 30 msec, inclusive, after a leading edge half-maximum of the pulse of optical energy. In some embodiments, the sub-threshold-for-stimulation amount electrical current is applied such that a leading edge half-maximum of the electrical current occurs between about 1 msec and about 10 msec, inclusive, after a leading edge half-maximum of the pulse of optical energy.

In some embodiments, the present invention provides an apparatus for triggering a response in a nerve and for increasing a margin of safety for in vivo optical-electrical stimulation of a nerve action potential (NAP) in neuronal tissue of a patient, the apparatus including means for applying a sub-threshold-for-stimulation amount electrical current through an area of the neuronal tissue; and means for applying a pulse of optical energy to a subportion of the area of the neuronal tissue to which the electrical current has been applied in order to stimulate a nerve action potential in one or more neurons of the neuronal tissue. In some embodiments, there exists a threshold amount of optical energy needed to stimulate a nerve-action-potential response in the neuronal tissue when no electrical current is applied, and wherein with the application of the amount of electrical current, the optical energy of the optical pulse is less than 90% of the threshold amount of optical energy needed to stimulate a nerve action potential in the neuronal tissue when no electrical current is applied. In some embodiments, there exists a threshold amount of optical energy needed to stimulate a nerve-action-potential response in the neuronal tissue when no electrical current is applied, and wherein with the application of the amount of electrical current, the optical energy of the optical pulse is less than 80% of the threshold amount of optical energy needed to stimulate a nerve action potential in the neuronal tissue when no electrical current is applied. In some embodiments, there exists a threshold amount of optical energy needed to stimulate a nerve-action-potential response in the neuronal tissue when no electrical current is applied, and wherein with the application of the amount of electrical current, the optical energy of the optical pulse is less than 60% of the threshold amount of optical energy needed to stimulate a nerve action potential in the neuronal tissue when no electrical current is applied. In some embodiments, there exists a threshold amount of optical energy needed to stimulate a nerve-action-potential response in the neuronal tissue when no electrical current is applied, and wherein with the application of the amount of electrical current, the optical energy of the optical pulse is less than 40% of the threshold amount of optical energy needed to stimulate a nerve action potential in the neuronal tissue when no electrical current is applied. In some embodiments, the apparatus applies the pulse of optical energy stimulation starting at a time delay of about 1 msec after the start of the electrical pulse having the sub-threshold-for-stimulation amount electrical current.

In some embodiments, the present invention provides an apparatus for triggering a response in a nerve and for increasing a margin of safety for in vivo optical stimulation of a nerve action potential (NAP) in neuronal tissue of a patient, the apparatus including an electrical-stimulation circuit that applies a sub-threshold-for-stimulation amount electrical current through an area of the neuronal tissue; and an optical-stimulation device that applies a pulse of optical energy to a subportion of the area of the neuronal tissue to which the electrical current has been applied in order to stimulate a nerve action potential in one or more neurons of the neuronal tissue. In some embodiments, there exists a threshold amount of optical energy needed to stimulate a nerve-action-potential response in the neuronal tissue when no electrical current is applied, and wherein with the application of the amount of electrical current, the optical energy of the optical pulse is less than 90% of the threshold amount of optical energy needed to stimulate a nerve action potential in the neuronal tissue when no electrical current is applied. In some embodiments, there exists a threshold amount of optical energy needed to stimulate a nerve-action-potential response in the neuronal tissue when no electrical current is applied, and wherein with the application of the amount of electrical current, the optical energy of the optical pulse is less than 80% of the threshold amount of optical energy needed to stimulate a nerve action potential in the neuronal tissue when no electrical current is applied. In some embodiments, there exists a threshold amount of optical energy needed to stimulate a nerve-action-potential response in the neuronal tissue when no electrical current is applied, and wherein with the application of the amount of electrical current, the optical energy of the optical pulse is less than 60% of the threshold amount of optical energy needed to stimulate a nerve action potential in the neuronal tissue when no electrical current is applied. In some embodiments, there exists a threshold amount of optical energy needed to stimulate a nerve-action-potential response in the neuronal tissue when no electrical current is applied, and wherein with the application of the amount of electrical current, the optical energy of the optical pulse is less than 40% of the threshold amount of optical energy needed to stimulate a nerve action potential in the neuronal tissue when no electrical current is applied. In some embodiments, the pulse of optical energy stimulation is applied starting at a time delay of about 1 msec after the start of the electrical pulse having the sub-threshold-for-stimulation amount electrical current. In some embodiments, the apparatus further includes a digital-delay generator configured to trigger the optical-stimulation device to apply the pulse of optical energy after a predetermined time delay (from the start of the electrical pulse) determined by the digital-delay generator. In some embodiments, the apparatus further includes a oscilloscope configured to measure an actual delay between the application of the sub-threshold-for-stimulation amount electrical current and the application of the pulse of optical energy.

It is to be understood that the above description is intended to be illustrative, and not restrictive. Although numerous characteristics and advantages of various embodiments as described herein have been set forth in the foregoing description, together with details of the structure and function of various embodiments, many other embodiments and changes to details will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein," respectively. Moreover, the terms "first," "second," and "third," etc., are used merely as labels, and are not intended to impose numerical requirements on their objects.

What is claimed is:

1. A method for triggering a response in a nerve and for in vivo optical-electrical stimulation of a nerve action potential (NAP) in neuronal tissue of a patient, the method comprising:
   applying a sub-threshold-for-stimulation amount electrical current through an area of the neuronal tissue; and
   applying a pulse of optical energy to a subportion of the area of the neuronal tissue to which the electrical current is applied in order to stimulate a nerve action potential in one or more neurons of the neuronal tissue.

2. The method of claim 1, wherein the pulse of optical energy has a duration of about 1 msec and is applied prior to the applying of the sub-threshold-for-stimulation amount of electrical current, wherein there is a delay of about 1 msec after the pulse of optical energy ends and before the applying of the sub-threshold-for-stimulation amount of electrical current begins, and wherein the applying of the sub-threshold-for-stimulation amount of electrical current has a duration of about 10 msec.

3. The method of claim 1, wherein there exists a threshold amount of optical energy needed to stimulate a nerve-action-potential response in the neuronal tissue when no electrical current is applied, and wherein with the application of the amount of electrical current, the optical energy of the optical pulse is less than 90% of the threshold amount of optical energy needed to stimulate a nerve action potential in the neuronal tissue when no electrical current is applied.

4. The method of claim 1, wherein there exists a threshold amount of optical energy needed to stimulate a nerve-action-potential response in the neuronal tissue when no electrical current is applied, and wherein with the application of the amount of electrical current, the optical energy of the optical pulse is less than 80% of the threshold amount of optical energy needed to stimulate a nerve action potential in the neuronal tissue when no electrical current is applied.

5. The method of claim 1, wherein there exists a threshold amount of optical energy needed to stimulate a nerve-action-potential response in the neuronal tissue when no electrical current is applied, and wherein with the application of the amount of electrical current, the optical energy of the optical pulse is less than 60% of the threshold amount of optical energy needed to stimulate a nerve action potential in the neuronal tissue when no electrical current is applied.

6. The method of claim 1, wherein there exists a threshold amount of optical energy needed to stimulate a nerve-action-potential response in the neuronal tissue when no electrical current is applied, and wherein with the application of the amount of electrical current, the optical energy of the optical pulse is less than 40% of the threshold amount of optical energy needed to stimulate a nerve action potential in the neuronal tissue when no electrical current is applied.

7. The method of claim 1, wherein the pulse of optical energy is applied such that a leading edge half-maximum of the optical pulse occurs at a time delay of about 1 msec after a leading edge half-maximum of the sub-threshold-for-stimulation amount electrical current is applied.

8. The method of claim 1, wherein the pulse of optical energy is applied such that a leading edge half-maximum of the optical pulse occurs between about 1 msec and about 30 msec, inclusive, after a leading edge half-maximum of the sub-threshold-for-stimulation amount electrical current.

9. The method of claim 1, wherein the sub-threshold-for-stimulation amount electrical current is applied such that a leading edge half-maximum of the electrical current occurs between about 1 msec and about 30 msec, inclusive, after a leading edge half-maximum the pulse of optical energy.

10. An apparatus for triggering a response in a nerve and for in vivo optical-electrical stimulation of a nerve action potential (NAP) in neuronal tissue of a patient, the apparatus comprising:
    means for applying a sub-threshold-for-stimulation amount electrical current through an area of the neuronal tissue; and
    means for applying a pulse of optical energy to a subportion of the area of the neuronal tissue to which the electrical current is applied in order to stimulate a nerve action potential in one or more neurons of the neuronal tissue.

11. The apparatus of claim 10, wherein there exists a threshold amount of optical energy needed to stimulate a nerve-action-potential response in the neuronal tissue when no electrical current is applied, and wherein with the application of the amount of electrical current, the optical energy of the optical pulse is less than 90% of the threshold amount of optical energy needed to stimulate a nerve action potential in the neuronal tissue when no electrical current is applied.

12. The apparatus of claim 10, wherein there exists a threshold amount of optical energy needed to stimulate a nerve-action-potential response in the neuronal tissue when no electrical current is applied, and wherein with the application of the amount of electrical current, the optical energy of the optical pulse is less than 80% of the threshold amount of optical energy needed to stimulate a nerve action potential in the neuronal tissue when no electrical current is applied.

13. The apparatus of claim 10, wherein there exists a threshold amount of optical energy needed to stimulate a nerve-action-potential response in the neuronal tissue when no electrical current is applied, and wherein with the application of the amount of electrical current, the optical energy of the optical pulse is less than 60% of the threshold amount of optical energy needed to stimulate a nerve action potential in the neuronal tissue when no electrical current is applied.

14. The apparatus of claim 10, wherein there exists a threshold amount of optical energy needed to stimulate a nerve-action-potential response in the neuronal tissue when no electrical current is applied, and wherein with the application of the amount of electrical current, the optical energy of the optical pulse is less than 40% of the threshold amount of optical energy needed to stimulate a nerve action potential in the neuronal tissue when no electrical current is applied.

15. The apparatus of claim 10, wherein the pulse of optical energy stimulation is applied starting at a time delay of about 1 msec after the sub-threshold-for-stimulation amount electrical current pulse is initially applied.

16. An apparatus for triggering a response in a nerve and for in vivo optical stimulation of a nerve action potential (NAP) in neuronal tissue of a patient, the apparatus comprising:
an electrical-stimulation circuit that applies a sub-threshold-for-stimulation amount electrical current through an area of the neuronal tissue; and
an optical-stimulation device that applies a pulse of optical energy to a subportion of the area of the neuronal tissue to which the electrical current is applied in order to stimulate a nerve action potential in one or more neurons of the neuronal tissue.

17. The apparatus of claim 16, wherein there exists a threshold amount of optical energy needed to stimulate a nerve-action-potential response in the neuronal tissue when no electrical current is applied, and wherein with the application of the amount of electrical current, the optical energy of the optical pulse is less than 90% of the threshold amount of optical energy needed to stimulate a nerve action potential in the neuronal tissue when no electrical current is applied.

18. The apparatus of claim 16, wherein there exists a threshold amount of optical energy needed to stimulate a nerve-action-potential response in the neuronal tissue when no electrical current is applied, and wherein with the application of the amount of electrical current, the optical energy of the optical pulse is less than 80% of the threshold amount of optical energy needed to stimulate a nerve action potential in the neuronal tissue when no electrical current is applied.

19. The apparatus of claim 16, wherein there exists a threshold amount of optical energy needed to stimulate a nerve-action-potential response in the neuronal tissue when no electrical current is applied, and wherein with the application of the amount of electrical current, the optical energy of the optical pulse is less than 60% of the threshold amount of optical energy needed to stimulate a nerve action potential in the neuronal tissue when no electrical current is applied.

20. The apparatus of claim 16, wherein there exists a threshold amount of optical energy needed to stimulate a nerve-action-potential response in the neuronal tissue when no electrical current is applied, and wherein with the application of the amount of electrical current, the optical energy of the optical pulse is less than 40% of the threshold amount of optical energy needed to stimulate a nerve action potential in the neuronal tissue when no electrical current is applied.

21. The apparatus of claim 16, wherein the pulse of optical energy stimulation is applied starting at a time delay of about 1 msec after the sub-threshold-for-stimulation amount electrical current pulse is initially applied.

22. The apparatus of claim 16, further comprising a digital-delay generator configured to trigger the optical-stimulation device to apply the pulse of optical energy after a predetermined time delay determined by the digital-delay generator.

23. The apparatus of claim 16, further comprising a oscilloscope configured to measure an actual delay between the application of the sub-threshold-for-stimulation amount electrical current and the application of the pulse of optical energy.

* * * * *